(12) United States Patent
Wang et al.

(10) Patent No.: US 12,077,528 B2
(45) Date of Patent: Sep. 3, 2024

(54) PREPARATION METHOD FOR DEUTERATED MACROCYCLIC COMPOUND

(71) Applicant: Shenzhen TargetRx, Inc., Guangdong (CN)

(72) Inventors: Yihan Wang, Guangdong (CN); Huanyin Li, Guangdong (CN)

(73) Assignee: Shenzhen TargetRx, Inc., Guangdong (CN)

( * ) Notice: Subject to any disclaimer, the term of this patent is extended or adjusted under 35 U.S.C. 154(b) by 665 days.

(21) Appl. No.: 17/297,050

(22) PCT Filed: Nov. 27, 2019

(86) PCT No.: PCT/CN2019/121235
§ 371 (c)(1),
(2) Date: May 26, 2021

(87) PCT Pub. No.: WO2020/108522
PCT Pub. Date: Jun. 4, 2020

(65) Prior Publication Data
US 2022/0024908 A1    Jan. 27, 2022

(30) Foreign Application Priority Data
Nov. 28, 2018 (CN) .......................... 201811432993.4

(51) Int. Cl.
*C07D 413/14* (2006.01)
*C07D 401/12* (2006.01)

(52) U.S. Cl.
CPC ......... *C07D 413/14* (2013.01); *C07D 401/12* (2013.01); *C07B 2200/05* (2013.01); *C07B 2200/07* (2013.01)

(58) Field of Classification Search
CPC .................................................. C07D 413/14
USPC ....................................................... 540/456
See application file for complete search history.

(56) References Cited

U.S. PATENT DOCUMENTS 9,637,500 B2 *  5/2017  Jensen ..................... A61P 35/00
2014/0135339 A1  5/2014  Bailey et al.

FOREIGN PATENT DOCUMENTS

| EP | 3 415 518 A1 | 12/2018 |
| JP | 2015-010091 A | 1/2015 |
| JP | 2015-510879 A | 4/2015 |
| WO | WO 2014/207606 A1 | 12/2014 |
| WO | WO 2017/148325 A1 | 9/2017 |
| WO | WO 2018/137679 A1 | 8/2018 |

OTHER PUBLICATIONS

Chinese Office Action for Application No. 201911179653.X, mailed Sep. 1, 2022.
Japanese Office Action for Application No. 2021-530171, mailed Aug. 2, 2022.
Duan et al., Developing an Asymmetric Transfer Hydrogenation Process for (S)-5-Fluoro-3-methylisobenzofuran-1(3H)-one, a Key Intermediate to Lorlatinib. Org Process Res Dev. Jul. 5, 2017; 21(9): 1340-48.
Qian et al., A novel approach for the synthesis of Crizotinib through the key chiral alcohol intermediate by asymmetric hydrogenation using highly active Ir-Spiro-PAP catalyst. Tetrahedron Letters. Jan. 21, 2014; 55(9): 1528-31.
International Search Report and Written Opinion for Application No. PCT/CN2019/121235, mailed Feb. 26, 2020.
Lochmüller et al., Chromatographic resolution of enantiomers selective review. J Chromatogr. Oct. 22, 1975;113(3):283-302. doi: 10.1016/s0021-9673(00)95302-0.
Partial European Search Report for Application No. 19890106.8, mailed Dec. 21, 2021.
Johnson et al., Discovery of (10R)-7-amino-12-fluoro-2,10,16-trimethyl-15-oxo-10,15,16,17-tetrahydro-2H-8,4-(metheno)pyrazolo[4,3-h][2,5,11]-benzoxadiazacyclotetradecine-3-carbonitrile (PF-06463922), a macrocyclic inhibitor of anaplastic lymphoma kinase (ALK) and c-ros oncogene 1 (ROS1) with preclinical brain exposure and broad-spectrum potency against ALK-resistant mutations. J Med Chem. Jun. 12, 2014;57(11):4720-44. doi: 10.1021/jm500261q. Epub Jun. 3, 2014.
CN201911179653.X, Sep. 1, 2022, Office Action and English translation thereof.
JP2021-530171, Aug. 2, 2022, Office Action and English translation thereof.
EP19890106.8, Dec. 21, 2021, Partial European Search Report.

* cited by examiner

*Primary Examiner* — Niloofar Rahmani
(74) *Attorney, Agent, or Firm* — Wolf, Greenfield & Sacks, P.C.

(57) ABSTRACT

Provided are a compound as represented by formula (D) and a preparation method therefor, where $X_2$ is a halogen, Pg is selected from H and an amino protecting group, such as Cbz, Boc, Fmoc, Alloc, Teoc, methoxycarbonyl or ethoxycarbonyl. Also provided are a synthesized intermediate compound of the formula (D) compound and a preparation method for the intermediate compound.

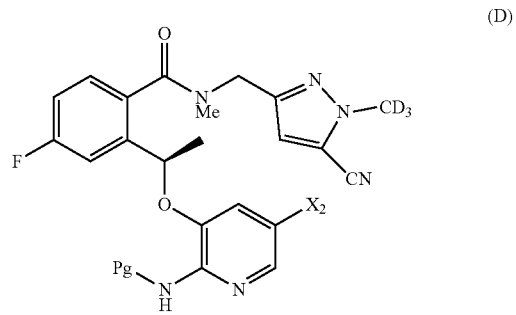

(D)

8 Claims, No Drawings

PREPARATION METHOD FOR DEUTERATED MACROCYCLIC COMPOUND

CROSS-REFERENCE TO RELATED APPLICATIONS

This application is a national application of PCT/CN2019/121235, filed on Nov. 27, 2019, which claims the priority of Chinese Patent Application No. 201811432993.4 filed on Nov. 28, 2018, which applications are incorporated herein in their entirety as a part of the specification.

FIELD OF THE INVENTION

The present disclosure belongs to the technical field of medicine, and especially relates to a preparation method for (10R)-7-amino-12-fluoro-2-(methyl-$d_3$)-10,16-dimethyl-15-oxo-10,15,16,17-tetrahydro-2H-8,4-(metheno)pyrazolo[4,3-h][2,5,11]benzoxadiazacyclotetradecine-3-carbonitrile (the compound of formula (A)), a synthetic intermediate for the compound of formula (A) (the compound of formula (D)) and a preparation method for the compound of formula (D). Also provided in the present disclosure are synthetic intermediates for the compound of formula (D) and a preparation method thereof.

BACKGROUND OF THE INVENTION

The compound of formula (A) is a potent small molecule inhibitor of ALK and ROS1 kinases, which shows activity against wild-type and mutant ALK (anaplastic lymphoma kinase) and wild-type and mutant ROS1 (ROS1 proto-oncogene receptor tyrosine kinase), and has improved pharmacokinetic properties. The properties (including anti-tumor properties) of the compound of formula (A) are pharmacologically mediated by inhibiting tyrosine kinase receptors. The compound of formula (A) is disclosed in International Publication No. WO 2017/148325 A1, which is incorporated herein by reference in its entirety.

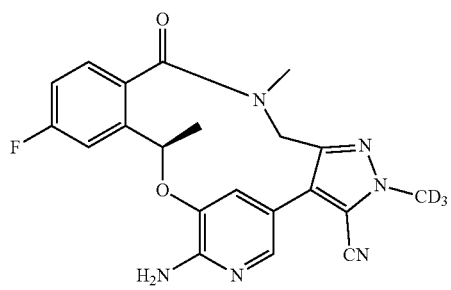

(A)

The compound of formula (A) is a chiral compound. The preparation of chiral drugs not only needs to comply with the principles of synthetic process for common chemical drugs, but also needs to consider the particularity of the chiral drugs: in the preparation of chiral drugs, it is necessary to pay attention to the changes of the chiral centers of the drugs and control the optical purity of the chiral drugs. In the International Publication No. WO 2017/148325 A1, the reaction route of synthesizing the compound of formula (A) is complicated, some purification methods of intermediate used therein are used in laboratories while not applicable in scale-up production, and the final product is obtained by resolution of racemate in a yield not more than 50%. These problems limit the subsequent commercial production of the compound of formula (A) as a potential anticancer drug with good performance.

Therefore, it is necessary to study the optimization of the synthesis process of the compound of formula (A) to provide a guarantee for the industrial production of the compound of formula (A).

SUMMARY OF THE INVENTION

In view of the above technical problems, the present disclosure uses an asymmetric synthesis method to prepare the compound of formula (A), and improves the purification method for intermediate compounds and final products, so that the compound of formula (A) with good stereoselectivity and high optical purity is obtained, making it more favorable to subsequent scale-up production process.

Specifically, the present disclosure relates to a preparation method for the compound of formula (A), a synthetic intermediate for the compound of formula (A), i.e., the compound of formula (D) (including the compound of formula (D-a) and the compound of formula (D-b)), and a preparation method for the compound of formula (D). Also provided in the present disclosure are synthetic intermediates for the compound of formula (D) and a preparation method thereof.

In one aspect, the present disclosure relates to a compound of formula (D).

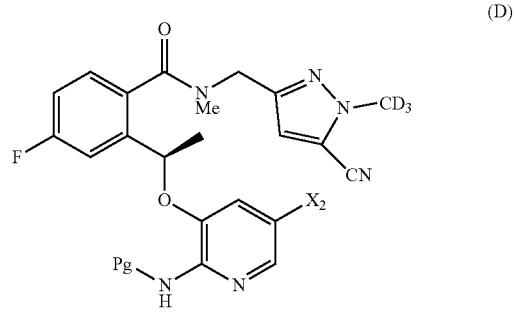

(D)

wherein $X_2$ is halogen, and Pg is selected from H and an amino-protecting group such as Cbz, Boc, Fmoc, Alloc, Teoc, methoxycarbonyl, or ethoxycarbonyl.

In a specific aspect, the compound of formula (D) is a compound of formula (D-a):

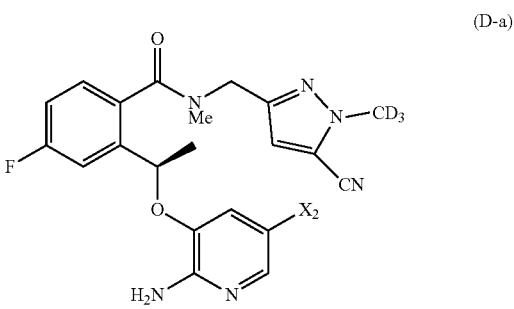

(D-a)

wherein $X_2$ is halogen.

In another specific aspect, the compound of formula (D) is a compound of formula (D-b):

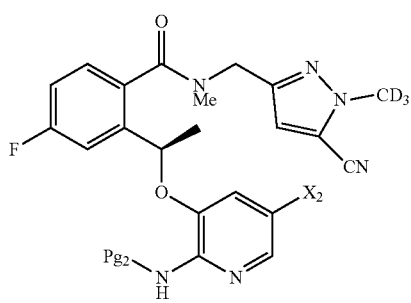

(D-b)

wherein $X_2$ is halogen, and $Pg_2$ is an amino-protecting group such as Cbz, Boc, Fmoc, Alloc, Teoc, methoxycarbonyl, or ethoxycarbonyl.

In another aspect, the present disclosure relates to a method for preparing a compound of formula (D-a), comprising the step of:

reacting a compound of formula (F) with a compound of formula (E-a) to form a compound of formula (D-a):

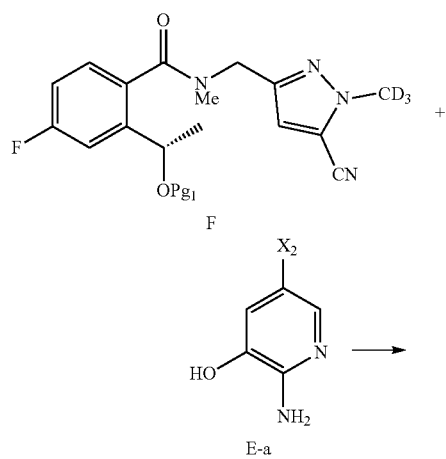

wherein $X_2$ is halogen, and $Pg_1$ is a hydroxy-protecting group such as Ms, Ns, Ts, or Tf.

In another aspect, the present disclosure relates to a method for preparing a compound of formula (F), comprising the step of:

acylating a compound of formula (G) to form a compound of formula (F):

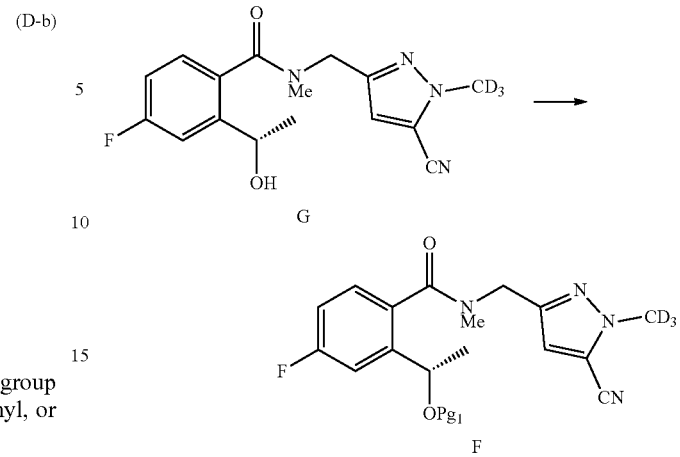

wherein $Pg_1$ is a hydroxy-protecting group such as Ms, Ns, Ts, or Tf.

In another aspect, the present disclosure relates to a method for preparing a compound of formula (C), comprising the step of:

reacting a compound of formula (D-a) with an amino-protecting agent to form a compound of formula (C):

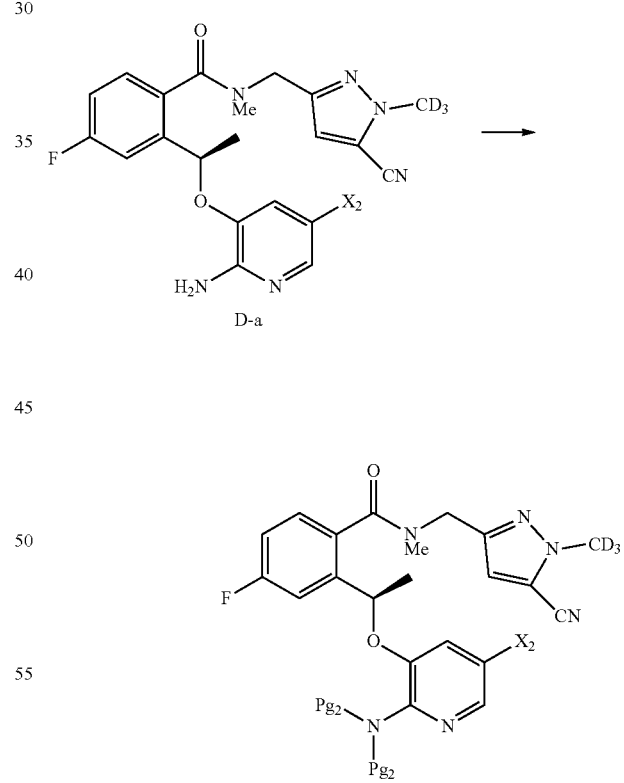

wherein $X_2$ is halogen, and $Pg_2$ is an amino-protecting group such as Cbz, Boc. Fmoc, Alloc, Teoc, methoxycarbonyl, or ethoxycarbonyl.

In another aspect, the present disclosure relates to a compound of formula (F)

(F)

wherein Pg₁ is a hydroxy-protecting group such as Ms, Ns, Ts, or Tf.

In another aspect, the present disclosure relates to a compound of formula (G)

(G)

In another aspect, the present disclosure relates to a compound of formula (C)

(C)

wherein X₂ is halogen, and Pg₂ is an amino-protecting group such as Cbz, Boc, Fmoc, Alloc, Teoc, methoxycarbonyl, or ethoxycarbonyl.

In another aspect, the present disclosure relates to a method for preparing a compound of formula (D-b), comprising the step of:

reacting a compound of formula (G) with a compound of formula (E-b) to form a compound of formula (D-b):

G

+

E-b

→

D-b wherein X₂ is halogen, and Pg₂ is an amino-protecting group such as Cbz, Boc, Fmoc, Alloc, Teoc, methoxycarbonyl, or ethoxycarbonyl.

In another aspect, the present disclosure relates to a method for preparing a compound of formula (E-b):

(E-b)

comprising the step of: reacting a compound of formula (E-b-1) with an amino-protecting agent to form a compound of formula (E-b):

E-b-1 → E-b wherein X₂ is halogen, and Pg₂ is an amino-protecting group such as Cbz, Boc, Fmoc, Alloc, Teoc, methoxycarbonyl, or ethoxycarbonyl.

In another aspect, the present disclosure relates to a method for preparing a compound of formula (C), comprising the step of:

protecting the amino group of the compound of formula (D-b) to form a compound of formula (C):

7

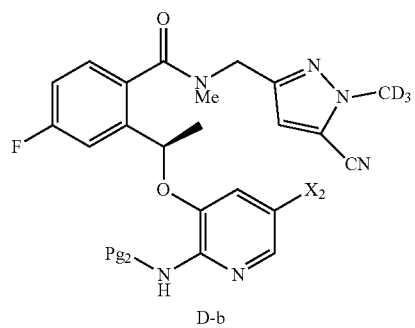

D-b

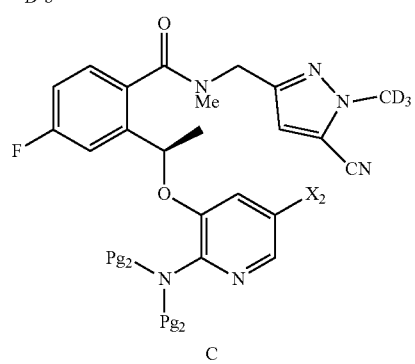

C wherein X₂ is halogen, and Pg₂ is an amino-protecting group such as Cbz. Boc, Fmoc, Alloc, Teoc, methoxycarbonyl, or ethoxycarbonyl.

In another aspect, the present disclosure relates to a compound of formula (E-b):

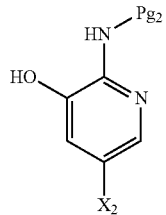
(E-b)

wherein X₂ is halogen, and Pg₂ is an amino-protecting group such as Cbz, Boc, Fmoc, Alloc, Teoc, methoxycarbonyl, or ethoxycarbonyl.

In another aspect, the present disclosure provides the following reaction route 1 for preparing the compound of formula (A):

Reaction route 1

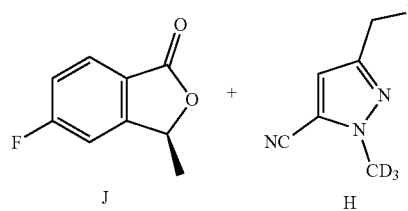

8

-continued

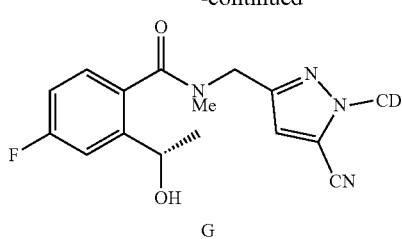

G

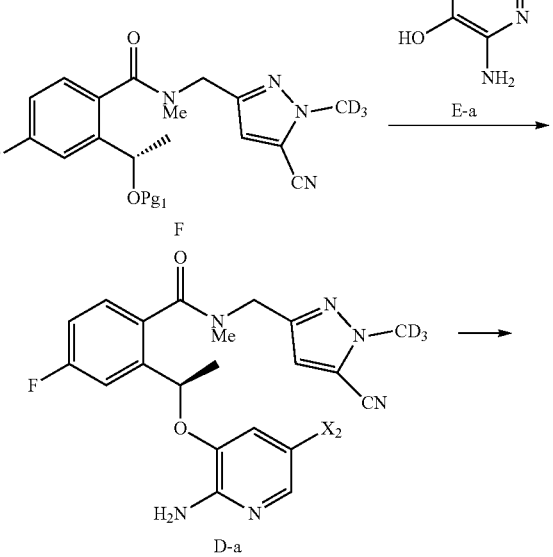

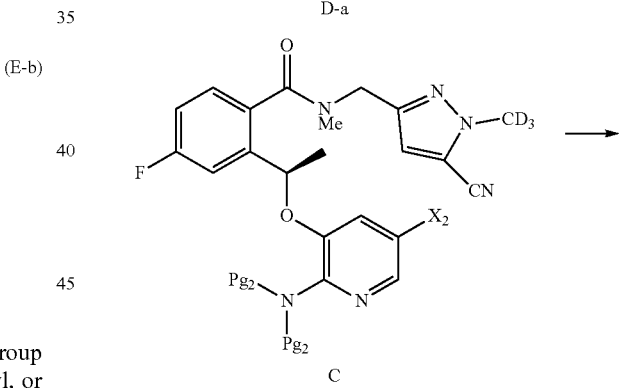

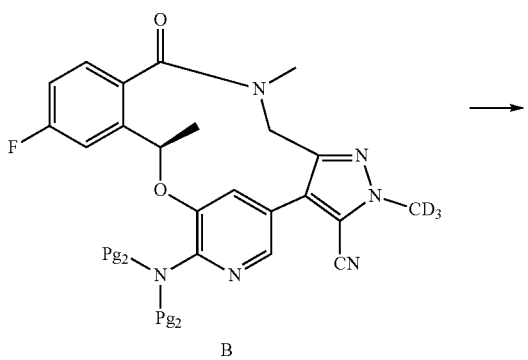

B

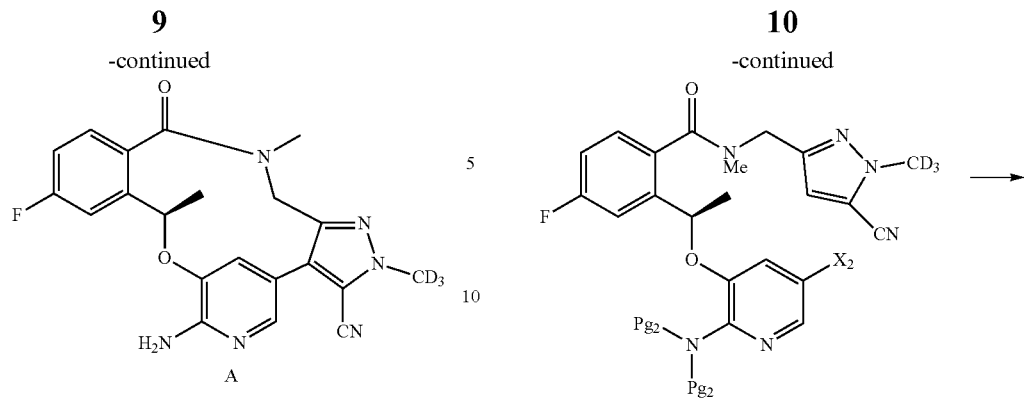
In another aspect, the present disclosure provides the following reaction route 2 for preparing the compound of formula (A):
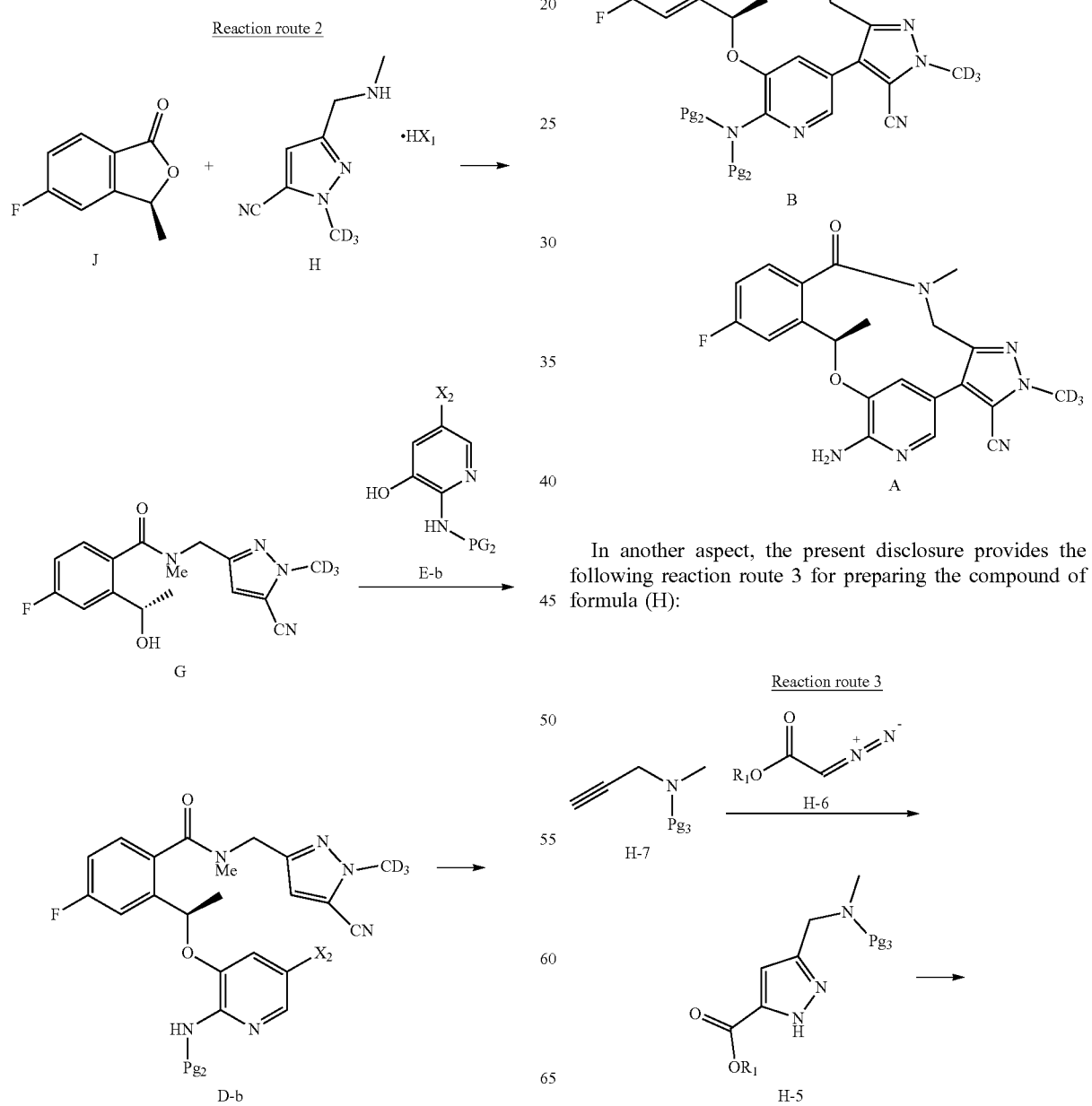
In another aspect, the present disclosure provides the following reaction route 3 for preparing the compound of formula (H):

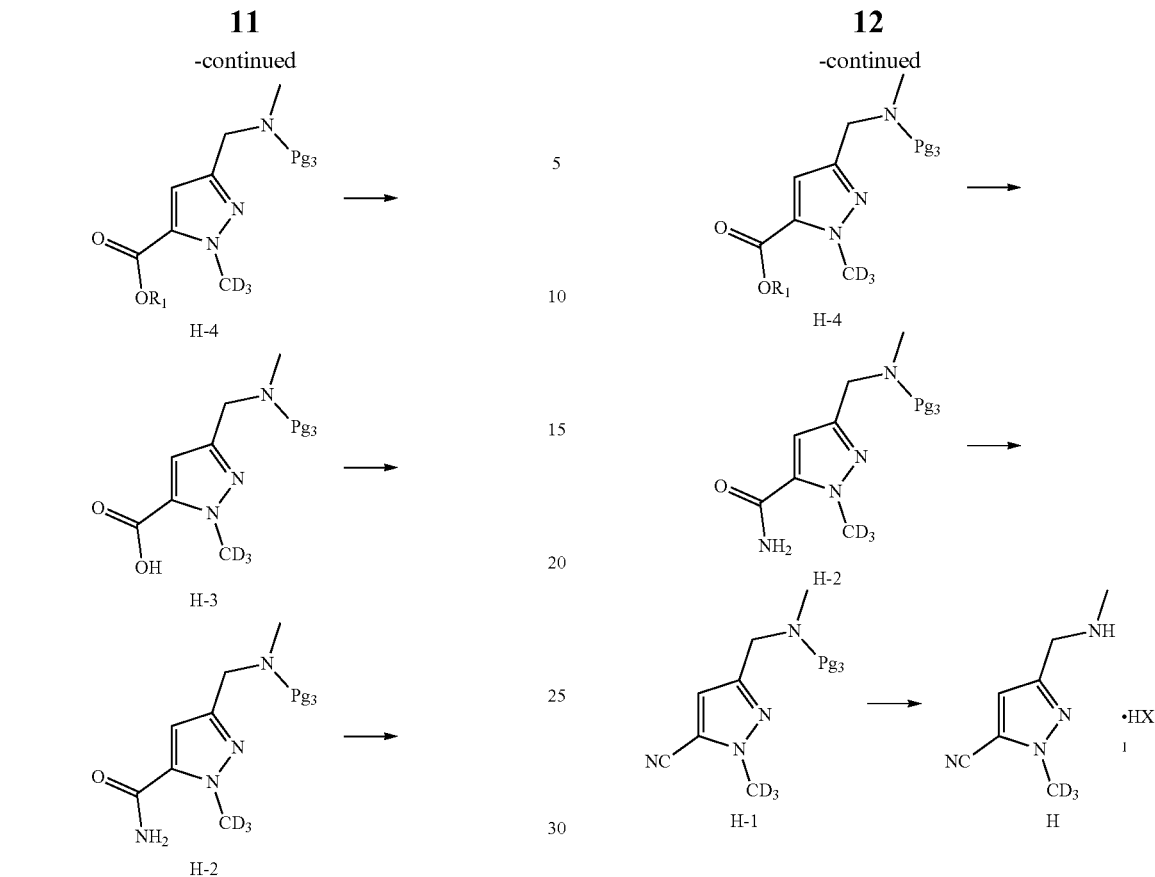

In another aspect, the present disclosure provides the following reaction route 4 for preparing the compound of formula (H):

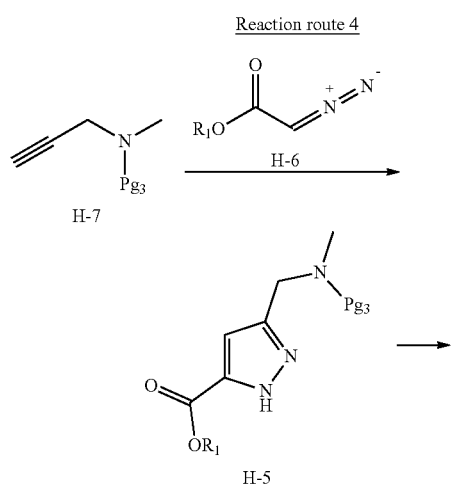

In another aspect, the present disclosure provides the following reaction route 5 for preparing the compound of formula (E-b):

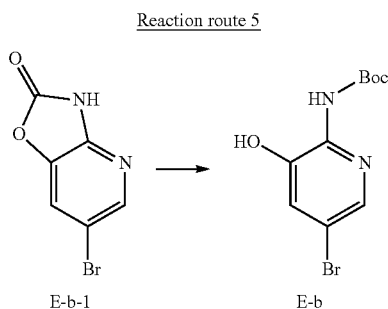 [SMILES: O=c1[nH]c2ncc(Br)cc2o1 ; CC(C)(C)OC(=O)Nc1ncc(Br)cc1O]

In another aspect, the present disclosure provides the following reaction route 6 for preparing the compound of formula (H-5):

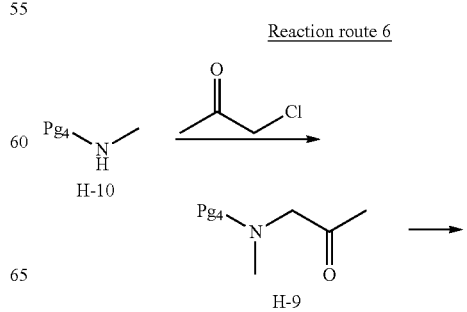

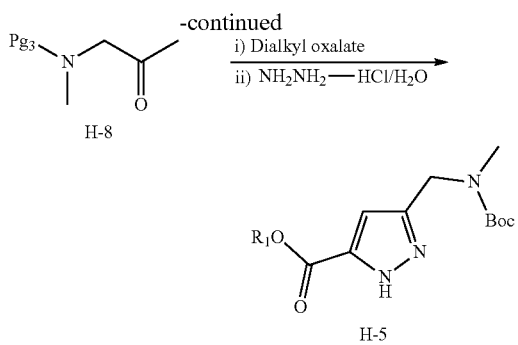

In another aspect, the present disclosure also provides the compound of formula (A) prepared according to the method described herein.

In another aspect, the present disclosure also provides a pharmaceutical composition, comprising the compound of formula (A) prepared as described herein and a pharmaceutically acceptable excipient.

In another aspect, the present disclosure also provides the use of the compound of formula (A) prepared as described herein or a pharmaceutical composition thereof in the manufacturer of a medicament for treating an ALK or ROS1 mediated cancer.

In some embodiments, the cancer is an ALK-mediated cancer. In some embodiments, the cancer is a cancer mediated by mutated ALK. In other embodiments, the cancer is a cancer mediated by ROS1. In other embodiments, the cancer is a cancer mediated by mutated ROS1. In other embodiments, the cancer is selected from lung cancer, bone cancer, pancreatic cancer, skin cancer, head or neck cancer, uterine cancer, ovarian cancer, rectal cancer, gastric cancer, colon cancer, breast cancer, fallopian tube cancer, cervical cancer, Hodgkin's cancer, esophageal cancer, thyroid cancer, adrenal cancer, prostate cancer, chronic or acute leukemia, lymphocytic lymphoma, renal cell carcinoma, or central nervous system tumors and combinations thereof. In other specific embodiments, the cancer is selected from non-small cell lung cancer, squamous cell carcinoma, hormone-refractory prostate cancer, papillary renal cell carcinoma, colorectal cancer, neuroblastoma, anaplastic large cell lymphoma, and lung cancer. In other specific embodiments, the cancer is non-small cell lung cancer. In other specific embodiments, the cancer is non-small cell lung cancer mediated by ALK or ROS1, more specifically, non-small cell lung cancer mediated by genetically altered ALK or genetically altered ROS1.

DETAILED DESCRIPTION OF THE EMBODIMENTS

Definitions and Abbreviations

As used herein, unless otherwise specified, "deuterated" means that one or more hydrogens in a compound or group are replaced by deuterium; "deuterated" may be monosubstituted, disubstituted, polysubstituted or fully substituted with deuteriums. The term "one or more deuterated" is used interchangeably with "deuterated one or more times".

As used herein, unless otherwise specified, the content of the deuterium isotope at the deuterated position is at least greater than the natural content of the deuterium isotope (0.015%), alternatively greater than 30%, yet alternatively greater than 50%, yet alternatively greater than 75%, yet alternatively greater than 95%, and yet alternatively greater than 99%.

As used herein, unless otherwise specified, "non-deuterated compound" refers to a compound containing deuterium in a ratio that is not higher than the natural content of deuterium isotope (0.015%).

As used herein, the term "independently selected from" means that multiple groups are selected from certain substituents respectively, and the groups are not related to each other, for example, "m and n are independently selected from 0 or 1" means that m is selected from 0 or 1, n is selected from 0 or 1, and m and n are not related to each other.

As used herein, the term "compound of the present disclosure" refers to a compound represented by formula (A). The term also includes various crystal forms, pharmaceutically acceptable salts, hydrates or solvates of the compound of formula (A).

As used herein, the term "pharmaceutically acceptable salt" refers to those salts which are, within the scope of sound medical judgment, suitable for use in contact with tissues of humans and lower animals without undue toxicity, irritation, allergies, etc., and are commensurate with a reasonable benefit/risk ratio. Pharmaceutically acceptable salts are well known in the art. For example, the pharmaceutically acceptable salts are described in detail by Berge et al., in J. Pharmaceutical Sciences (1977) 66: 1-19. Pharmaceutically acceptable salts of the compounds disclosed herein include those derived from suitable inorganic and organic acids and inorganic and organic bases. Examples of pharmaceutically acceptable non-toxic acid addition salts are salts formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid. Salts formed by using conventional methods used in the art such as ion exchange are also included. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to a complex in which a compound of the present disclosure coordinates with a solvent molecule in a particular ratio. "Hydrate" refers to a complex formed by coordination of a compound of the present disclosure with water.

Also disclosed herein are isotopically labeled compounds to the extent of the original compounds disclosed herein. Examples of isotopes that can be used in the compounds disclosed herein include hydrogen, carbon, nitrogen, oxygen, phosphorus, sulfur, fluorine, and chlorine isotopes, such as $^2H$, $^3H$, $^{13}C$, $^{14}C$, $^{15}N$, $^{17}O$, $^{18}O$, $^{31}P$, $^{32}P$, $^{35}S$, $^{18}F$, and $^{36}Cl$, respectively. Compounds disclosed herein, or enantiomers, diastereomers, isomers, pharmaceutically acceptable salts or solvates thereof, in which the isotopes as described above or other isotope atoms are contained, are within the scope disclosed herein. Certain isotopically (including radioisotopes such as $^3H$ and $^{14}C$) labeled compounds disclosed herein are useful in the tissue distribution assay of drugs and substrates. Tritium, i.e., $^3H$, and carbon-14, i.e., $^{14}C$, are easier to be prepared and detected and are the first choice for isotopes. Isotopically-labeled compounds can be prepared by conventional methods using the schemes shown in the Examples by replacing the non-isotopic reagents with readily available isotopically labeled reagents.

"Protecting groups" include "amino-protecting groups" and "hydroxy-protecting groups", which are used to prevent certain functional groups (for example, amino and hydroxyl) from undergoing undesired reactions. The selection of suitable protecting groups for specific functional groups as well as suitable conditions for protecting and deprotecting are well known in the art. For example, numerous protecting groups and their introduction and removal are described in T. W. Greene and P. G. M. Wuts, Protecting Groups in Organic Synthesis, Second Edition. Wiley, New York, 1991 and references cited therein.

Abbreviations

Ms: methanesulfonyl
Ns: nitrobenzenesulfonyl
Ts: p-toluenesulfonyl
Tf: trifluoromethanesulfonyl
Cbz: benzyloxycarbonyl
Boc: tert-butoxycarbonyl
Fmoc: fluorenylmethoxycarbonyl
Alloc: allyloxycarbonyl
Teoc: 2-(trimethylsilyl)ethoxycarbonyl
$AlCl_3$: aluminum trichloride
$BF_3$: boron trifluoride
$FeCl_3$: ferric chloride
$ZnCl_2$: zinc chloride
DCM: dichloromethane
DCE: dichloroethane
$CCl_4$: carbon tetrachloride
DIPEA: N,N-diisopropylethylamine
TEA: triethylamine
NMM: N-methylmorpholine
DBU: 1,8-diazabicyclo[5.4.0]undec-7-ene
DMAP: 4-dimethylaminopyridine
DMF: N,N-dimethylformamide
DMA: N,N-dimethylacetamide
DMSO: dimethyl sulfoxide
NMP: N-methylpyrrolidone
$Pd(OAc)_2$: palladium acetate
$Pd(PPh_3)_4$: tetra(triphenylphosphine)palladium
$Pd_2(dba)_3$: tris(dibenzylideneacetone)dipalladium
$PdCl_2$: palladium chloride
$PdCl_2(dppf)$: [1,1'-bis(diphenylphosphino)ferrocene]dichloropalladium(II)
$PdCl_2(PPh_3)_2$: bis(triphenylphosphine)palladium(II) chloride
XPhos: 2-dicyclohexylphosphino-2',4',6'-triisopropylbiphenyl
SPhos: 2-dicyclohexylphosphino-2',6'-dimethoxybiphenyl
XantPhos: 4,5-bis(diphenylphosphino)-9,9-dimethylxanthene
JohnPhos: 2-(dicyclohexylphosphino)biphenyl
BINAP: 2,2'-bis(diphenylphosphino)-1,1'-binaphthyl
Cataxium A: n-butylbis(1-adamantyl)phosphine
DEAD: diethyl azodicarboxylate
DIAD: diisopropyl azodicarboxylate
DBAD: di-tert-butyl azodicarboxylate
DCAD: di-p-chlorobenzyl azodicarboxylate
CDI: N'N-carbonyldiimidazole
$Boc_2O$: di-tert-butyl dicarbonate
$K_2CO_3$: potassium carbonate
Tol: toluene
n-BuLi: n-butyl lithium
THF: tetrahydrofuran
TEMPO: 2,2,6,6-tetramethylpiperidinooxy
NaClO: sodium hypochlorite
$NaHCO_3$: sodium bicarbonate
PE: petroleum ether
EA: ethyl acetate
RuCl(p-cymene)[(S,S)-Ts-DPEN]: (S,S)—N-(p-toluenesulfonyl)-1,2-diphenyl-1,2-ethylenediamine(p-isopropyltoluene)ruthenium(II) chloride
EtOH: ethanol
Tributyl(1-ethoxyvinyl)tin(IV): tributyl(1-ethoxyvinyl)tin(IV)
TPP: triphenylphosphine
TFAA: trifluoroacetic anhydride Preparation Method The present processes may be performed using methods disclosed herein and routine modifications thereof which will be apparent given the disclosure herein and methods well known in the art. Conventional and well-known synthetic methods may be used in addition to the teachings herein. The synthesis of typical compounds described herein (e.g. the compound of formula (A) and the compound of formula (H)) may be accomplished as described in the following examples.

Typical embodiments of compounds in accordance with the present disclosure may be synthesized using the general reaction routes described below. It will be apparent given the description herein that the general schemes may be altered by substitution of the starting materials with other materials having similar structures to result in products that are correspondingly different. Given a desired product for which the substituent groups are defined, the necessary starting materials generally may be determined by inspection. Starting materials are typically obtained from commercial sources or synthesized using published methods. For synthesizing compounds which are embodiments of the present disclosure, inspection of the structure of the compound to be synthesized will provide the identity of each substituent group. The identity of the final product will generally render apparent the identity of the necessary starting materials by a simple process of inspection, given the examples herein.

The compounds disclosed herein can be prepared from readily available starting materials using, for example, the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Furthermore, the compounds disclosed herein may contain one or more chiral centers. Accordingly, if desired, such compounds can be prepared or isolated as pure stereoisomers, i.e., as individual enantiomers or diastereomers or as stereoisomer-enriched mixtures. All such stereoisomers (and enriched mixtures) are included within the scope of the present disclosure, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

The starting materials for the following reactions are generally known compounds or can be prepared by known procedures or obvious modifications thereof. For example, many of the starting materials are available from commercial suppliers such as Shanghai Tebo Chemical Technology Co., Ltd. (Shanghai, China), Saen Chemical Technology (Shanghai) Co., Ltd. (Shanghai, China), Shanghai Hopu Chemical Technology Co., Ltd. (Shanghai, China), Shanghai Jinlu Pharmaceutical Technology Co., Ltd. (Shanghai, China), Anhui Dexinjia Biomedical Co., Ltd. (Anhui, China), Tianjin Pharmacn Medical Technology Co., Ltd. (Tianjin. China). Hunan Hezhong Pharmaceutical Technology Co., Ltd. (Hunan, China). Others may be prepared by procedures or obvious modifications thereof, described in standard reference texts such as Fieser and Fieser's Reagents for Organic Synthesis (John Wiley, and Sons, 1991), Rodd's Chemistry of Carbon Compounds (Elsevier Science Publishers, 1989), Organic Reactions (John Wiley, and Sons, 1991), March's Advanced Organic Chemistry (John Wiley, and Sons, 5th Edition, 2001), and Larock's Comprehensive Organic Transformations (VCH Publishers Inc., 1989).

In each of the exemplary schemes it may be advantageous to separate reaction products from each other and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse phase and normal phase; size exclusion; ion exchange; high, medium, and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by-product, or the like. Such reagents include adsorbents or absorbents such as activated carbon, molecular sieves, ion exchange media, or the like. Alternatively, the reagents can be acids (in the case of a basic material), bases (in the case of an acidic material), binding reagents such as antibodies, binding proteins, selective chelators such as crown ethers, liquid/liquid ion extraction reagents (LIX), or the like.

Selection of appropriate methods of separation depends on the nature of the materials involved. For example, boiling point, and molecular weight in distillation and sublimation, presence or absence of polar functional groups in chromatography, stability of materials in acidic and basic media in multiphase extraction, and the like. One skilled in the art will apply techniques most likely to achieve the desired separation.

A single stereoisomer, e.g., an enantiomer, substantially free of its stereoisomer may be obtained by resolution of the racemic mixture using a method such as formation of diastereomers using optically active resolving agents (Stereochemistry of Carbon Compounds, (1962), E. L. Eliel, McGraw Hill: Lochmuller, C. H., (1975) J. Chromatogr., 113: (3) 283-302). Racemic mixtures of chiral compounds disclosed herein can be separated and isolated by any suitable method, including. (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions.

As described above, the present disclosure provides a method for preparing the compound of formula (A) in some embodiments.

Reaction route 1 represents an exemplary synthesis of the compound of formula (A), and can be performed according to the embodiments described herein. The exemplary synthesis shown in reaction route 1 is expected to be particularly advantageous.

Reaction Route 1

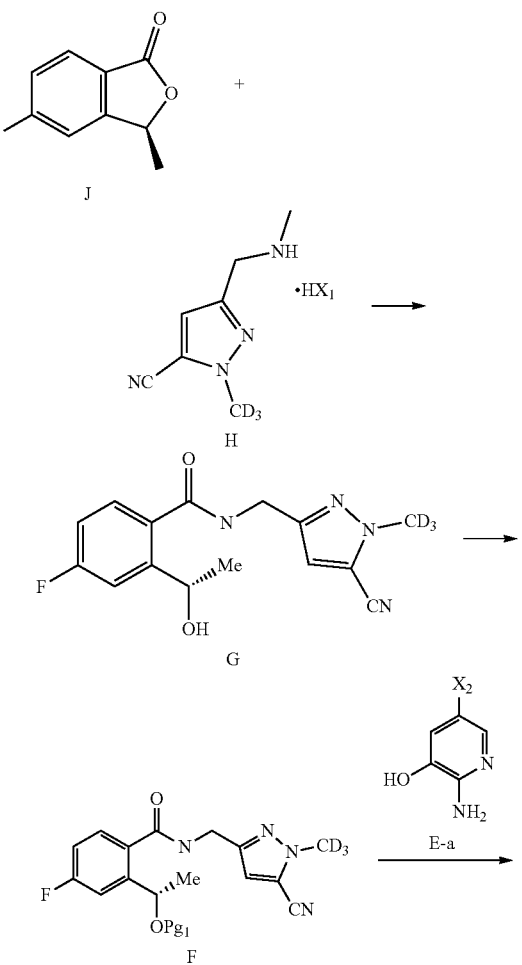

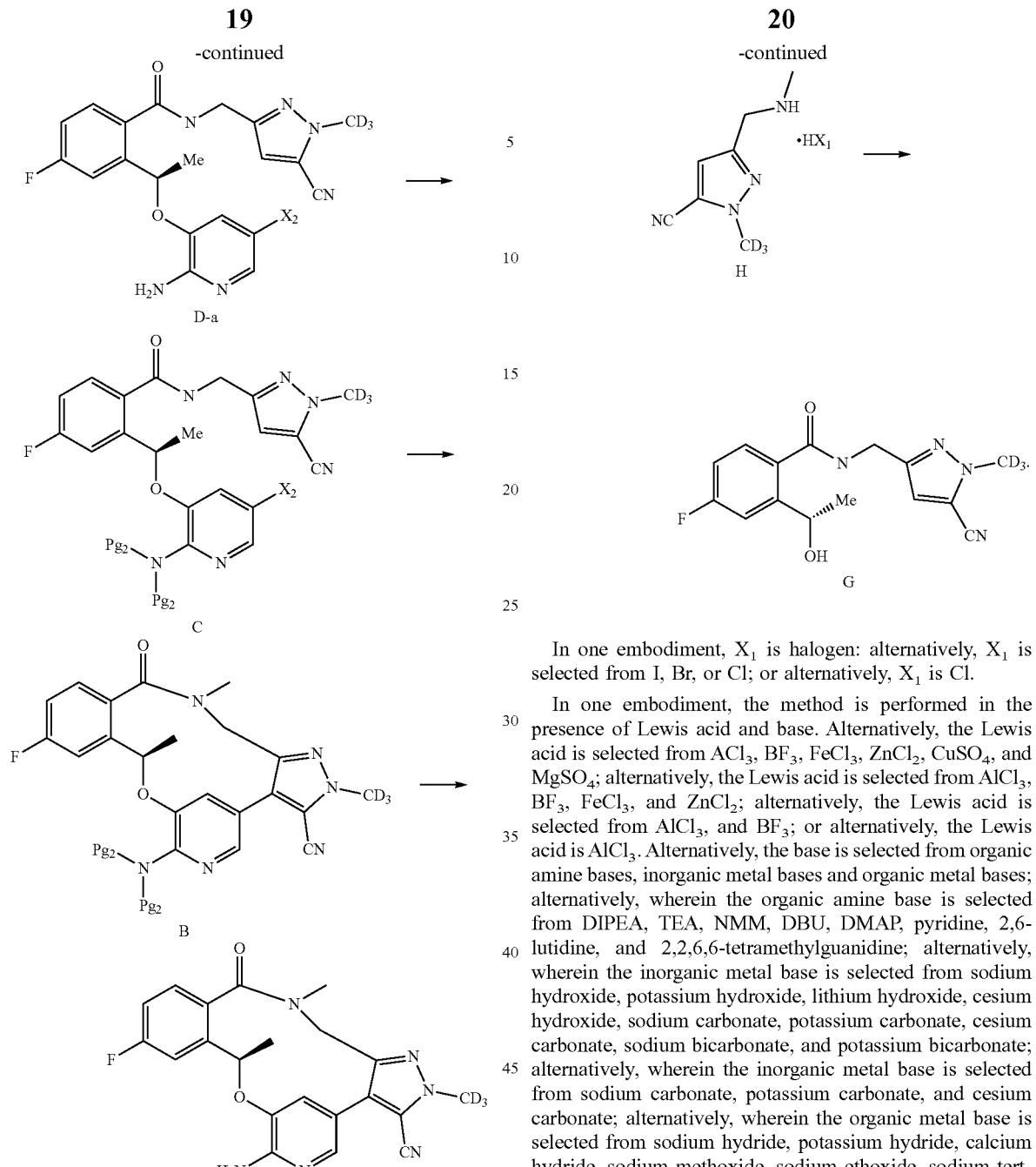

In one embodiment, X₁ is halogen; alternatively, $X_1$ is selected from I, Br, or Cl; or alternatively, $X_1$ is Cl.

In one embodiment, the method is performed in the presence of Lewis acid and base. Alternatively, the Lewis acid is selected from $ACl_3$, $BF_3$, $FeCl_3$, $ZnCl_2$, $CuSO_4$, and $MgSO_4$; alternatively, the Lewis acid is selected from $AlCl_3$, $BF_3$, $FeCl_3$, and $ZnCl_2$; alternatively, the Lewis acid is selected from $AlCl_3$, and $BF_3$; or alternatively, the Lewis acid is $AlCl_3$. Alternatively, the base is selected from organic amine bases, inorganic metal bases and organic metal bases; alternatively, wherein the organic amine base is selected from DIPEA, TEA, NMM, DBU, DMAP, pyridine, 2,6-lutidine, and 2,2,6,6-tetramethylguanidine; alternatively, wherein the inorganic metal base is selected from sodium hydroxide, potassium hydroxide, lithium hydroxide, cesium hydroxide, sodium carbonate, potassium carbonate, cesium carbonate, sodium bicarbonate, and potassium bicarbonate; alternatively, wherein the inorganic metal base is selected from sodium carbonate, potassium carbonate, and cesium carbonate; alternatively, wherein the organic metal base is selected from sodium hydride, potassium hydride, calcium hydride, sodium methoxide, sodium ethoxide, sodium tert-butoxide, potassium tert-butoxide, lithium tert-butoxide, and aluminum isopropoxide; or alternatively, wherein the base is TEA.

In some embodiments, the method is performed in the presence of a solvent, such as a non-polar aprotic solvent; alternatively, wherein the solvent is selected from DCM, DCE, and $CCl_4$; or alternatively, wherein the solvent is DCM.

In some embodiments, the method is performed at a temperature of about −20° C. to about 50° C.; alternatively, about 10° C. to about 40° C.; alternatively, about 0° C. to about 25° C.; alternatively, about 0° C. to about 10° C.; or alternatively, about 25° C.

In another embodiment, the present disclosure provides a method of acylating a compound of formula (G) to form a compound of formula (F):

In one embodiment, the present disclosure provides a method of reacting a compound of formula (J) with a compound of formula (H) to form a compound of formula (G):

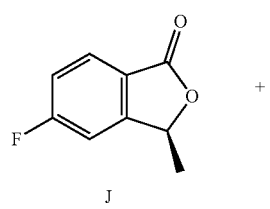

J

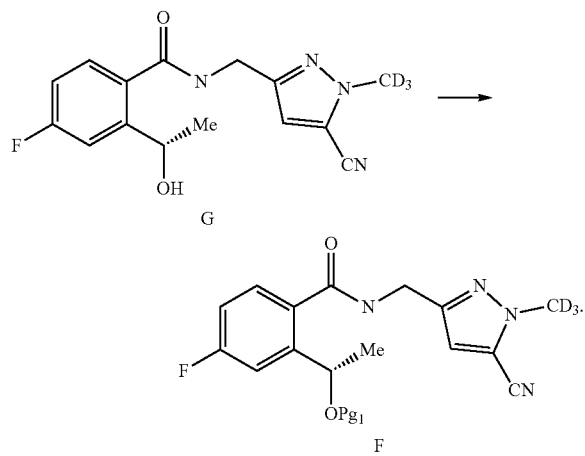

In some embodiments, $Pg_1$ is a hydroxy-protecting group such as Ms, Ns, Ts, or Tf: or alternatively, $Pg_1$ is Ms.

In some embodiments, the method is performed in the presence of acylating agents and bases: alternatively, wherein the acylating agent is selected from MsCl, NsCl, TsCl, and TfCl, alternatively, wherein the acylating agent is MsCl; alternatively, wherein the base is selected from organic amine bases, inorganic metal bases and organic metal bases; alternatively, wherein the organic amine base is selected from DIPEA, TEA, NMM, DBU, DMAP, pyridine, 2,6-lutidine, and 2,2,6,6-tetramethylguanidine; alternatively, the organic amine base is TEA: alternatively, wherein the inorganic metal base is selected from sodium hydroxide, potassium hydroxide, lithium hydroxide, cesium hydroxide, sodium carbonate, potassium carbonate, cesium carbonate, sodium bicarbonate, and potassium bicarbonate; alternatively, the inorganic metal base is selected from sodium carbonate, potassium carbonate, and cesium carbonate; or alternatively, wherein the organic metal base is selected from sodium hydride, potassium hydride, calcium hydride, sodium methoxide, sodium ethoxide, sodium tert-butoxide, potassium tert-butoxide, lithium tert-butoxide, and aluminum isopropoxide.

In some embodiments, the method is performed in the presence of a nucleophilic catalyst; alternatively, wherein the nucleophilic catalyst is DMAP.

In some embodiments, the method is performed in the presence of a solvent, such as an aprotic solvent or a mixture thereof: alternatively, wherein the solvent is selected from DCM, DCE, ethyl acetate, methyl acetate, isopropyl acetate, n-hexane, n-heptane, petroleum ether, acetone, acetonitrile, toluene, methyl tert-butyl ether, tetrahydrofuran, 2-methyltetrahydrofuran, 1,4-dioxane, ethylene glycol monomethyl ether, ethylene glycol dimethyl ether, DMF, DMA, and DMSO: alternatively, wherein the solvent is selected from DCM, methyl tert-butyl ether, and acetone: or alternatively, wherein the solvent is DCM.

In some embodiments, the method is performed at a temperature of about –20° C. to about 50° C.; alternatively, about 0° C. to about 25° C.: alternatively, about 0° C. to about 10° C.; or alternatively, about 25° C.

In another embodiment, the present disclosure provides a method of reacting a compound of formula (F) with a compound of formula (E-a) to form a compound of formula (D-a):

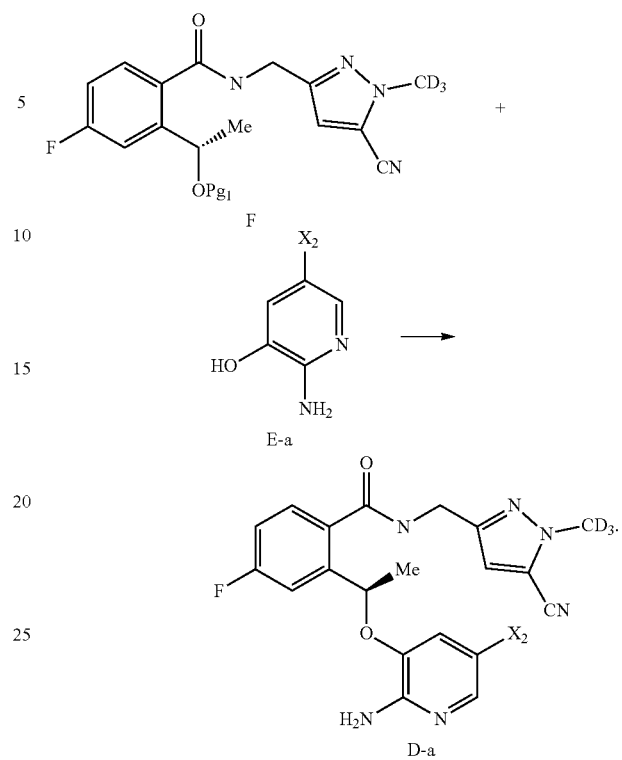

In some embodiments, $X_2$ is halogen; alternatively, $X_2$ is selected from I, Br, and Cl; or alternatively, $X_2$ is Br.

In some embodiments, the method is performed in the presence of a base: alternatively, wherein the base is selected from organic amine bases and inorganic metal bases; alternatively, wherein the organic amine base is selected from DIPEA, TEA, NMM, DBU, DMAP, pyridine, 2,6-lutidine, and 2,2,6,6-tetramethylguanidine: alternatively, the organic amine base is DIPEA or TEA; alternatively, wherein the inorganic metal base is selected from sodium hydroxide, potassium hydroxide, lithium hydroxide, cesium hydroxide, sodium phosphate, potassium phosphate, cesium phosphate, sodium hydrogen phosphate, potassium hydrogen phosphate, sodium dihydrogen phosphate, potassium dihydrogen phosphate, sodium carbonate, potassium carbonate, cesium carbonate, sodium bicarbonate, and potassium bicarbonate; alternatively, wherein the base is selected from potassium carbonate and cesium carbonate; or alternatively, wherein the base is potassium phosphate.

In some embodiments, the method is performed in the presence of a solvent, such as an aprotic solvent, a polar protic solvent or a mixture thereof; alternatively, wherein the solvent is selected from DCM, DCE, ethyl acetate, methyl acetate, isopropyl acetate, n-hexane, n-heptane, petroleum ether, acetone, acetonitrile, toluene, methyl tert-butyl ether, tetrahydrofuran, 2-methyltetrahydrofuran, 1,4-dioxane, ethylene glycol monomethyl ether, ethylene glycol dimethyl ether, DMF, DMA, DMSO, methanol, ethanol, isobutanol, tert-butanol, isopropanol, n-propanol, n-pentanol, and isopentanol; alternatively, wherein the solvent is selected from acetonitrile and DMF; or alternatively, the polar protic solvent is selected from methanol and isopropanol. Alternatively, the polar protic solvent is ethylene glycol dimethyl ether.

In some embodiments, the method is performed at a temperature of about −20° C. to reflux temperature, alternatively, about 25° C. to reflux temperature; or alternatively, about 50° C.

In some embodiments, the final product is purified by treating with an acid solution to form a salt, followed by treating with a base to form a free base. The acid solution includes a solution of HCl in an organic solvent, such as a solution of HCl in dioxane, a solution of HCl in ethyl acetate, and an alcoholic solution of HCl (such as a solution of HCl in isopropanol), etc.; alternatively, a solution of HCl in ethyl acetate is used. The base used for the treatment includes an aqueous solution of an inorganic metal base such as sodium hydroxide, potassium hydroxide, lithium hydroxide, cesium hydroxide, sodium carbonate, potassium carbonate, cesium carbonate, sodium bicarbonate, and potassium bicarbonate; or alternatively, a saturated aqueous solution of sodium bicarbonate.

In another embodiment, the present disclosure provides a method of protecting a compound of formula (D-a) to form a compound of formula (C):

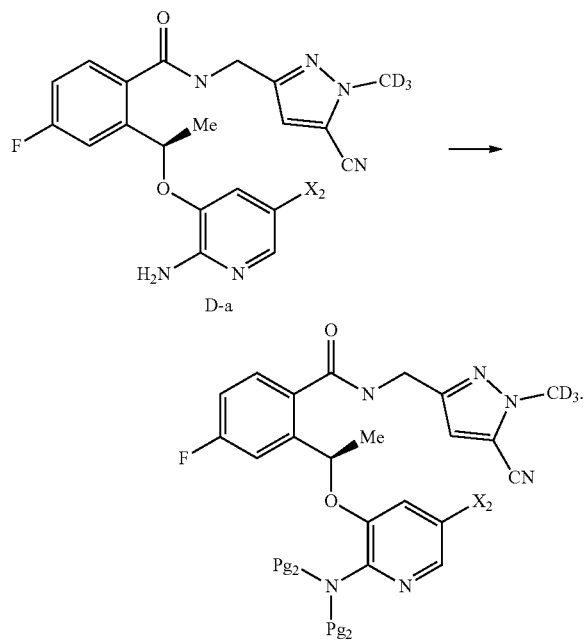

In some embodiments, $Pg_2$ is an amino-protecting group such as Cbz, Boc, Fmoc, Alloc, Teoc, methoxycarbonyl, or ethoxycarbonyl; or alternatively, $Pg_2$ is Boc.

In some embodiments, the method is performed in the presence of an amino-protecting agent and a base; alternatively, wherein the amino-protecting agent is selected from Cbz-Cl, $Boc_2O$, Fmoc-Cl, Alloc-Cl, Teoc-Cl, methyl chloroformate, and ethyl chloroformate: alternatively, wherein the amino-protecting agent is $Boc_2O$; alternatively, wherein the base is selected from organic amine bases and inorganic metal bases; alternatively, wherein the organic amine base is selected from DIPEA, TEA, NMM, DBU, DMAP, pyridine, 2,6-lutidine, and 2,2,6,6-tetramethylguanidine; alternatively, wherein the inorganic metal base is selected from sodium carbonate, potassium carbonate, cesium carbonate, sodium bicarbonate, potassium bicarbonate, sodium hydroxide, potassium hydroxide, lithium hydroxide, and cesium fluoride: alternatively, wherein the base is TEA; or alternatively, wherein the base is DIPEA.

In some embodiments, the method is performed in the presence of a nucleophilic catalyst, alternatively, wherein the nucleophilic catalyst is DMAP.

In some embodiments, the method is performed in the presence of a solvent, such as an aprotic solvent or a mixture thereof: alternatively, wherein the solvent is selected from DCM, DCE, ethyl acetate, methyl acetate, isopropyl acetate, n-hexane, n-heptane, petroleum ether, acetone, acetonitrile, toluene, methyl tert-butyl ether, tetrahydrofuran, 2-methyltetrahydrofuran, 1,4-dioxane, ethylene glycol monomethyl ether, ethylene glycol dimethyl ether, DMF, DMA, and DMSO: or alternatively, wherein the solvent is DCM.

In some embodiments, the method is performed at a temperature of about −20° C. to reflux temperature, alternatively, about 25° C. to reflux temperature, or alternatively, about 30° C.

In another embodiment, the present disclosure provides a method of cyclizing a compound of formula (C) to form a compound of formula (B):

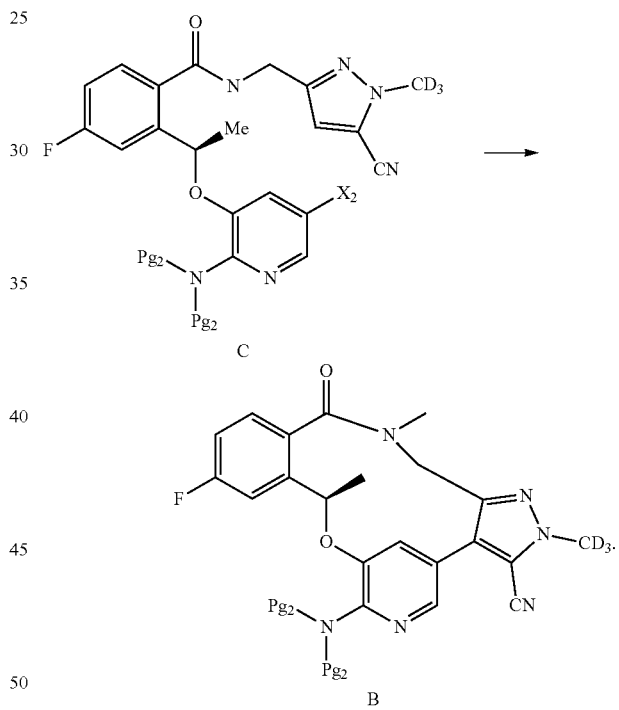

In some embodiments, the method is performed in the presence of a palladium catalyst, a phosphine reagent and a base; alternatively, wherein the palladium catalyst is selected from $Pd(OAc)_2$, $Pd(PPh_3)_4$, $Pd_2(dba)_3$, $PdCl_2$, $PdCl_2(dppf)$, and $PdCl_2(PPh_3)_2$; alternatively, wherein the palladium catalyst is $Pd(OAc)_2$; alternatively, wherein the phosphine reagent is selected from n-butylbis(1-adamantyl)phosphine, triphenylphosphine, tributylphosphine, tri-tert-butylphosphine, tricyclohexylphosphine, XPhos, SPhos, XantPhos, JohnPhos, and BINAP; alternatively, wherein the phosphine reagent is n-butylbis(1-adamantyl)phosphine; alternatively, wherein the base is selected from organic amine bases, organic metal bases and inorganic metal bases; alternatively, wherein the organic amine base is selected from DIPEA, TEA, NMM, DBU, DMAP, pyridine, 2,6- lutidine, and 2,2,6,6-tetramethylguanidine; alternatively, wherein the organic metal base is selected from sodium acetate and potassium acetate; alternatively, wherein the inorganic metal base is selected from sodium carbonate, potassium carbonate, cesium carbonate, sodium bicarbonate, potassium bicarbonate, sodium hydroxide, potassium hydroxide, lithium hydroxide, and cesium fluoride; or alternatively, wherein the base is selected from sodium acetate and potassium acetate.

In some embodiments, the method is performed in the presence of a solvent, such as an aprotic solvent, a polar protic solvent or a mixture thereof: alternatively, wherein the solvent is selected from n-propanol, isopropanol, n-butanol, sec-butanol, isobutanol, n-pentanol, sec-pentanol, isopentanol, neopentyl alcohol, tert-pentanol, ethylene glycol monomethyl ether, ethylene glycol dimethyl ether, PEG, methyl tert-butyl ether, tetrahydrofuran, 2-methyltetrahydrofuran, 1,4-dioxane, DMF, and DMSO: or alternatively, wherein the solvent is tert-pentanol.

In some embodiments, the method is performed at a temperature of about −20° C. to reflux temperature; alternatively, reflux temperature; or alternatively, about 105° C.

In another embodiment, the present disclosure provides a method of removing the protecting group $Pg_2$ from the compound of formula (B) to obtain the compound of formula (A).

In some embodiments, the method is performed in the presence of an acid; alternatively, wherein the acid is selected from trifluoroacetic acid, acetic acid, p-toluenesulfonic acid, benzenesulfonic acid, formic acid, a solution of HCl in dioxane, an aqueous solution of hydrochloric acid, and an alcoholic solution of hydrochloric acid; alternatively, wherein the acid is selected from trifluoroacetic acid, an aqueous solution of hydrochloric acid, and a solution of hydrochloric acid in isopropanol: or alternatively, wherein the acid is concentrated hydrochloric acid.

In some embodiments, the method is performed in the presence of a solvent, such as an aprotic solvent, a polar protic solvent or a mixture thereof: alternatively, wherein the solvent is selected from DCM, DCE, ethyl acetate, methyl acetate, methyl tert-butyl ether, tetrahydrofuran, 2-methyltetrahydrofuran, 1,4-dioxane, acetonitrile, methanol, ethanol, isopropanol, and water; alternatively, wherein the solvent is DCM; or alternatively, wherein the solvent is ethyl acetate.

In some embodiments, the method is performed at a temperature of about −20° C. to reflux temperature: alternatively, about 0° C. to about 25° C.; or alternatively, about 45° C.

Reaction route 2 represents an exemplary synthesis of a compound of formula (A), and can be performed according to the embodiments described herein. The specific reaction conditions and reagents used in reaction route 2 are discussed below.

Reaction Route 2

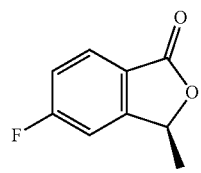

J

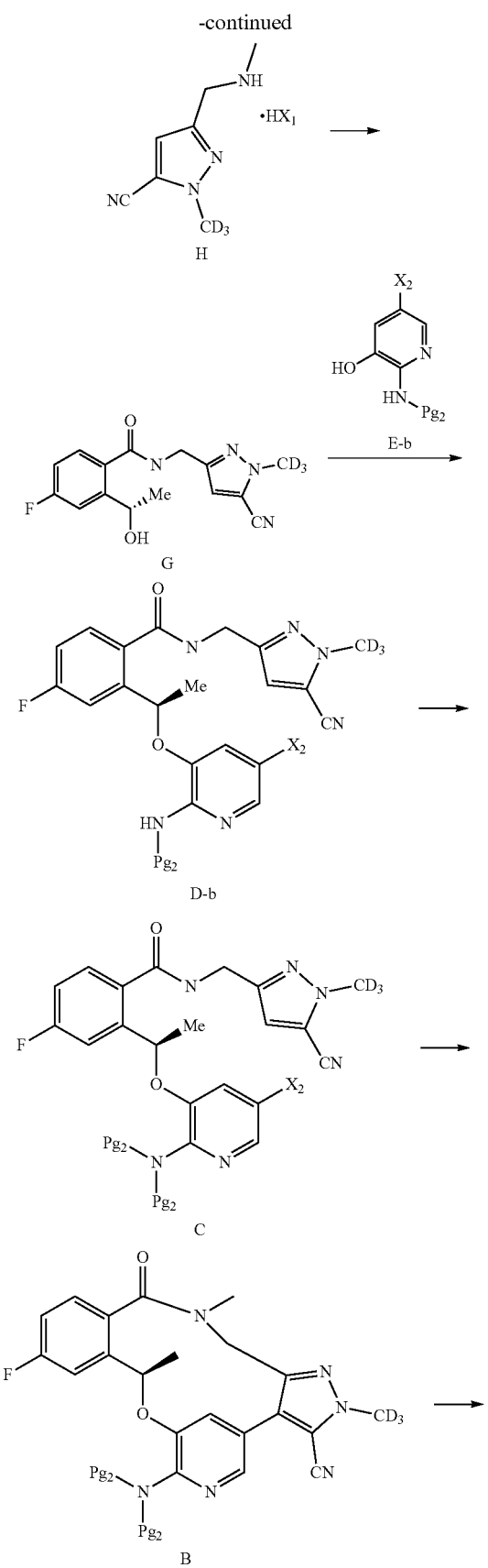

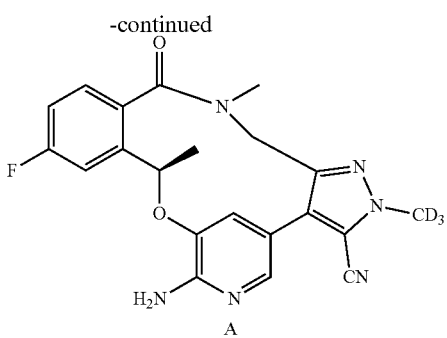

A

In reaction route 2, in addition to the same method as in reaction route 1, the present disclosure also provides a method of reacting a compound of formula (G) with a compound of formula (E-b) to form a compound of formula (D-b):

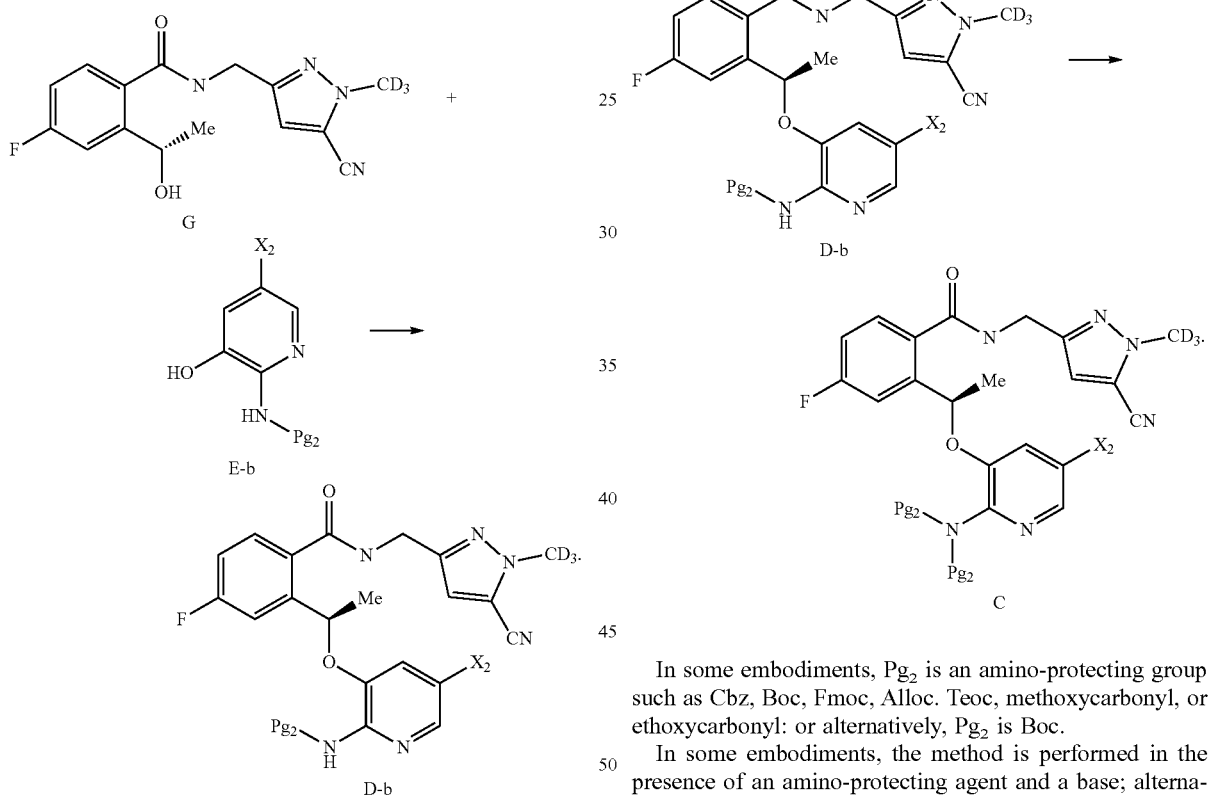

In some embodiments, $X_2$ is halogen; alternatively, $X_2$ is selected from I, Br, and Cl; or alternatively, $X_2$ is Cl.

In some embodiments, $Pg_2$ is an amino-protecting group such as Cbz, Boc, Fmoc, Alloc, Teoc, methoxycarbonyl, or ethoxycarbonyl; or alternatively, $Pg_2$ is Boc.

In some embodiments, the method is performed in the presence of an azodicarboxylate reagent and a phosphine reagent; alternatively, wherein the azodicarboxylate reagent is selected from DEAD, DIAD, DBAD, and DCAD: alternatively, wherein the azodicarboxylate reagent is DIAD; alternatively, wherein the phosphine reagent is selected from triphenylphosphine, tributylphosphine, trimethylphosphine, tri-tert-butylphosphine, tricyclohexylphosphine, n-butylbis(1-adamantyl)phosphine, XPhos, SPhos, XantPhos, John-Phos, and BINAP; or alternatively, wherein the phosphine reagent is triphenylphosphine.

In some embodiments, the method is performed in the presence of a solvent, such as a polar aprotic solvent; alternatively, wherein the solvent is selected from tetrahydrofuran, 2-methyltetrahydrofuran, DCM, toluene, methyl tert-butyl ether, ethyl acetate, acetonitrile, DCE, 1,4-dioxane, ethylene glycol monomethyl ether, ethylene glycol dimethyl ether, DMF, DMA, and DMSO: or alternatively, wherein the solvent is tetrahydrofuran.

In some embodiments, the method is performed at a temperature of about −20° C. to about reflux temperature; or alternatively, 25° C.

In another embodiment, the present disclosure provides a method of protecting a compound of formula (D-b) to form a compound of formula (C):

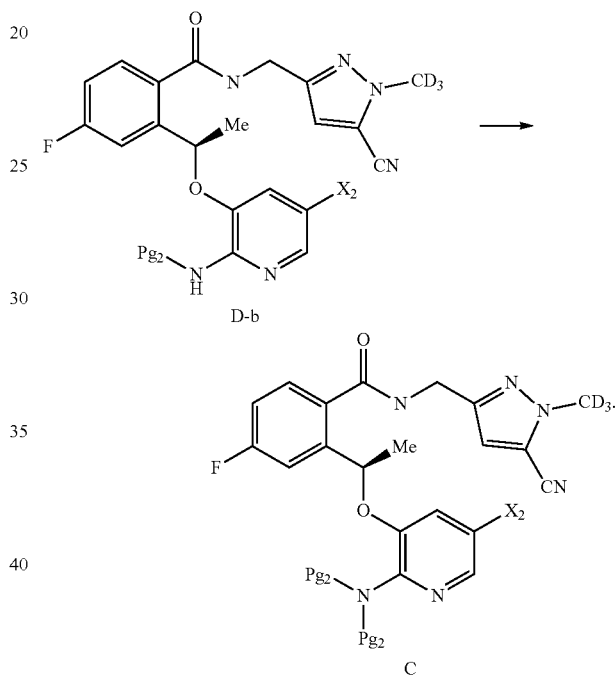

In some embodiments, $Pg_2$ is an amino-protecting group such as Cbz, Boc, Fmoc, Alloc. Teoc, methoxycarbonyl, or ethoxycarbonyl: or alternatively, $Pg_2$ is Boc.

In some embodiments, the method is performed in the presence of an amino-protecting agent and a base; alternatively, wherein the amino-protecting agent is selected from Cbz-Cl, $Boc_2O$, Fmoc-Cl, Alloc-Cl, Teoc-Cl, methyl chloroformate, and ethyl chloroformate; alternatively, wherein the amino-protecting agent is $Boc_2O$: alternatively, wherein the base is selected from organic amine bases and inorganic metal bases; alternatively, wherein the organic amine base is selected from DIPEA, TEA, NMM, DBU, DMAP, pyridine, 2,6-lutidine, and 2,2,6,6-tetramethylguanidine; alternatively, wherein the inorganic metal base is selected from sodium carbonate, potassium carbonate, cesium carbonate, sodium bicarbonate, potassium bicarbonate, sodium hydroxide, potassium hydroxide, lithium hydroxide, and cesium fluoride; or alternatively, wherein the base is TEA.

In some embodiments, the method is performed in the presence of a nucleophilic catalyst: alternatively, wherein the nucleophilic catalyst is DMAP.

In some embodiments, the method is performed in the presence of a solvent, such as an aprotic solvent or a mixture thereof; alternatively, wherein the solvent is selected from DCM, DCE, ethyl acetate, methyl acetate, isopropyl acetate, n-hexane, n-heptane, petroleum ether, acetone, acetonitrile, toluene, methyl tert-butyl ether, tetrahydrofuran, 2-methyl-tetrahydrofuran, 1,4-dioxane, ethylene glycol monomethyl ether, ethylene glycol dimethyl ether, DMF, DMA, and DMSO: or alternatively, wherein the solvent is DCM.

In some embodiments, the method is performed at a temperature of about −20° C. to reflux temperature; or alternatively, 25° C. to reflux temperature.

Reaction route 3 represents an exemplary synthesis of a compound of formula (H), and can be performed according to the embodiments described herein. The specific reaction conditions and reagents used in reaction route 3 are discussed below.

Reaction Route 3

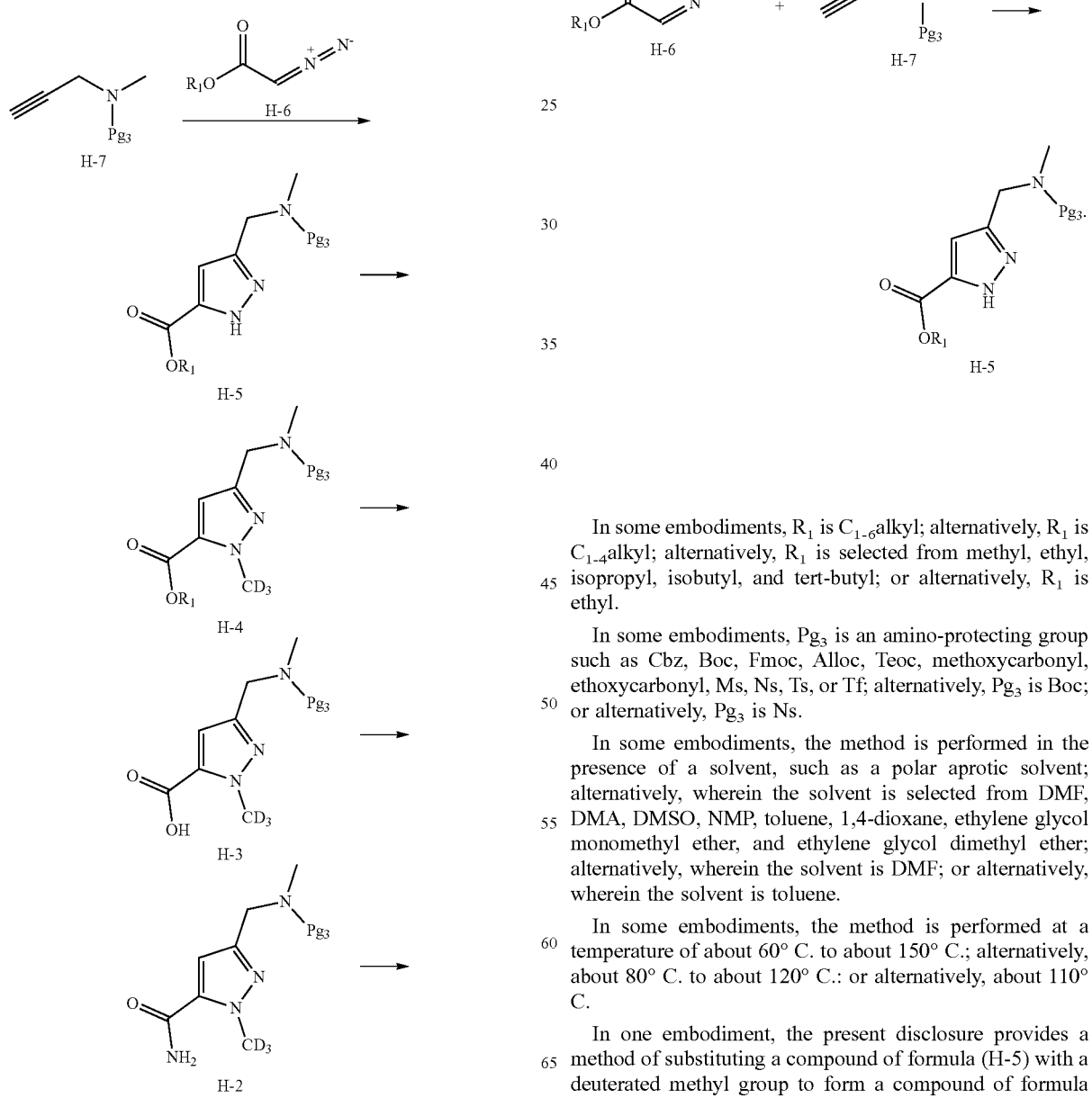

In one embodiment, the present disclosure provides a method of reacting a compound of formula (H-6) with a compound of formula (H-7) to form a compound of formula (H-5):

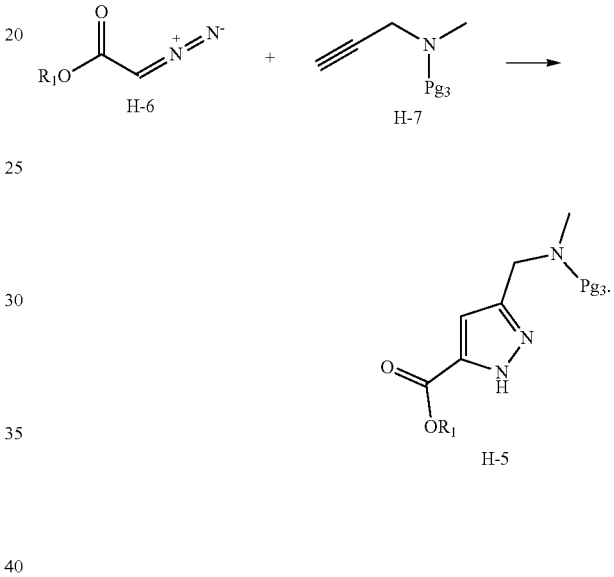

In some embodiments, $R_1$ is $C_{1-6}$alkyl; alternatively, $R_1$ is $C_{1-4}$alkyl; alternatively, $R_1$ is selected from methyl, ethyl, isopropyl, isobutyl, and tert-butyl; or alternatively, $R_1$ is ethyl.

In some embodiments, $Pg_3$ is an amino-protecting group such as Cbz, Boc, Fmoc, Alloc, Teoc, methoxycarbonyl, ethoxycarbonyl, Ms, Ns, Ts, or Tf; alternatively, $Pg_3$ is Boc; or alternatively, $Pg_3$ is Ns.

In some embodiments, the method is performed in the presence of a solvent, such as a polar aprotic solvent; alternatively, wherein the solvent is selected from DMF, DMA, DMSO, NMP, toluene, 1,4-dioxane, ethylene glycol monomethyl ether, and ethylene glycol dimethyl ether; alternatively, wherein the solvent is DMF; or alternatively, wherein the solvent is toluene.

In some embodiments, the method is performed at a temperature of about 60° C. to about 150° C.; alternatively, about 80° C. to about 120° C.: or alternatively, about 110° C.

In one embodiment, the present disclosure provides a method of substituting a compound of formula (H-5) with a deuterated methyl group to form a compound of formula (H-4):

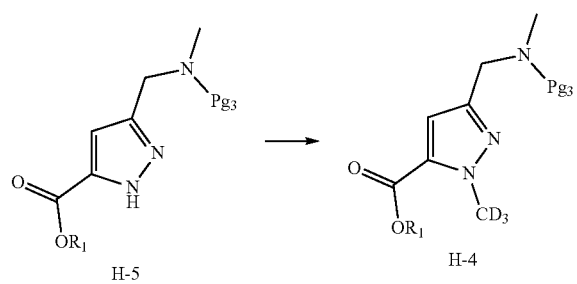

wherein R$_1$ is C$_{1-6}$ alkyl, alternatively ethyl; Pg$_3$ is an amino-protecting group such as Cbz, Boc, Fmoc, Alloc, Teoc, methoxycarbonyl, ethoxycarbonyl, Ms, Ns, Ts, or Tf; or alternatively, Pg$_3$ is Boc.

In some embodiments, the method is performed in the presence of a deuterated-methylating agent: alternatively, wherein the deuterated-methylating agent is selected from CD$_3$OD, CD$_3$I, CD$_3$OC(O)OCD$_3$, CD$_3$OS(O)$_2$OCD$_3$, and TsOCD$_3$: alternatively, wherein the deuterated-methylating agent is TsOCD$_3$: or alternatively, the deuterated-methylating agent is CD$_3$OD.

In some embodiments, the method is performed in the presence of a deuterated-methylating agent and a base: alternatively, wherein the deuterated-methylating agent is selected from CD$_3$OD, CD$_3$I, CD$_3$OC(O)OCD$_3$, CD$_3$OS(O)$_2$OCD$_3$, and TsOCD$_3$; or alternatively, the deuterated-methylating agent is TsOCD$_3$. Alternatively, the base is selected from organic amine bases, inorganic metal bases and organic metal bases; alternatively, wherein the organic amine base is selected from DIPEA, TEA, NMM, DBU, DMAP, pyridine, 2,6-lutidine, and 2,2,6,6-tetramethylguanidine; alternatively, wherein the inorganic metal base is selected from sodium hydroxide, potassium hydroxide, lithium hydroxide, cesium hydroxide, sodium phosphate, potassium phosphate, cesium phosphate, sodium hydrogen phosphate, potassium hydrogen phosphate, sodium dihydrogen phosphate, potassium dihydrogen phosphate, sodium carbonate, potassium carbonate, cesium carbonate, sodium bicarbonate, and potassium bicarbonate; alternatively, wherein the organic metal base is selected from sodium hydride, potassium hydride, calcium hydride, sodium methoxide, sodium ethoxide, sodium tert-butoxide, potassium tert-butoxide, lithium tert-butoxide, and aluminum isopropoxide; alternatively, the base is selected from sodium carbonate, potassium carbonate, and cesium carbonate; or alternatively, wherein the base is potassium phosphate.

In some embodiments, the method also uses a catalyst such as tetrabutylammonium bromide (TBAB), tetrabutylammonium chloride (TBAC), benzyltrimethylammonium chloride, 18-crown-6, 15-crown-5, or the like; alternatively, wherein the method uses tetrabutylammonium bromide (TBAB).

In some embodiments, the method is performed in the presence of an azodicarboxylate reagent and a phosphine reagent; alternatively, wherein the azodicarboxylate reagent is selected from DEAD, DIAD, DBAD, and DCAD: alternatively, wherein the azodicarboxylate reagent is DBAD: alternatively, wherein the phosphine reagent is selected from triphenylphosphine, tributylphosphine, trimethylphosphine, tri-tert-butylphosphine, tricyclohexylphosphine, n-butylbis(1-adamantyl)phosphine, XPhos, SPhos, XantPhos, JohnPhos, and BINAP; or alternatively, wherein the phosphine reagent is triphenylphosphine.

In some embodiments, the method is performed in the coexistence of a deuterated-methylating reagent, an azodicarboxylate reagent and a phosphine reagent; alternatively, wherein the deuterated-methylating reagent is selected from CD$_3$OD, CD$_3$I, CD$_3$OC(O)OCD$_3$, CD$_3$OS(O)$_2$OCD$_3$, and TsOCD$_3$; alternatively, the deuterated-methylating reagent is CD$_3$OD; alternatively, wherein the azodicarboxylate reagent is selected from DEAD, DIAD, DBAD, and DCAD; alternatively, wherein the azodicarboxylate reagent is DBAD; alternatively, wherein the phosphine reagent is selected from triphenylphosphine, tributylphosphine, trimethylphosphine, tri-tert-butylphosphine, tricyclohexylphosphine, n-butylbis(1-adamantyl)phosphine, XPhos, SPhos, XantPhos, JohnPhos, and BINAP; or alternatively, wherein the phosphine reagent is triphenylphosphine.

In some embodiments, the method is performed in a solvent, such as an aprotic solvent: alternatively, wherein the solvent is selected from DCM, DCE, tetrahydrofuran, 2-methyltetrahydrofuran, acetonitrile, toluene, 1,4-dioxane, methyl tert-butyl ether, ethylene glycol monomethyl ether, ethylene glycol dimethyl ether, DMF, DMA, NMP, and DMSO; alternatively, wherein the solvent is selected from DMF and tetrahydrofuran: or alternatively, wherein the solvent is DMF.

In some embodiments, the method is performed at a temperature of about −20° C. to about 50° C.; or alternatively, about −10° C. to about 25° C.

In one embodiment, the present disclosure provides a method of hydrolyzing a compound of formula (H-4) to form a compound of formula (H-3):

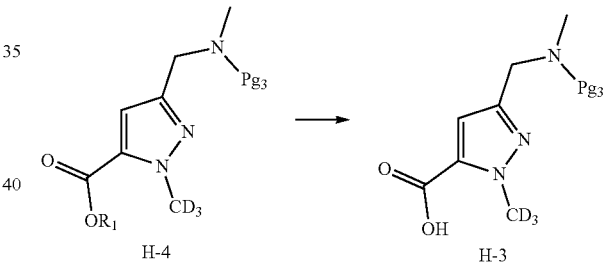

wherein R$_1$ is C$_{1-6}$ alkyl, or alternatively ethyl; Pg$_3$ is an amino-protecting group such as Cbz, Boc, Fmoc, Alloc, Teoc, methoxycarbonyl, ethoxycarbonyl, Ms, Ns, Ts, or Tf; or alternatively, Pg$_3$ is Boc.

In some embodiments, the method is performed in an aqueous or alcoholic solution of a base; alternatively, wherein the base is selected from lithium hydroxide, sodium hydroxide, potassium hydroxide, and cesium hydroxide: alternatively, wherein the base is lithium hydroxide monohydrate: alternatively, the alcohol is selected from methanol, ethanol, isopropanol, and propanol; or alternatively, wherein the alcohol is methanol.

In some embodiments, the method is performed in a solvent; alternatively, wherein the solvent is selected from tetrahydrofuran, 2-methyltetrahydrofuran, n-heptane, and DCM; alternatively, wherein the solvent is tetrahydrofuran; or alternatively, wherein the solvent is n-heptane.

In some embodiments, the method is performed at a temperature of about −20° C. to about 50° C.: or alternatively, about −10° C. to about 25° C.

In one embodiment, the present disclosure provides a method of reacting a compound of formula (H-3) with ammonia water to form a compound of formula (H-2):

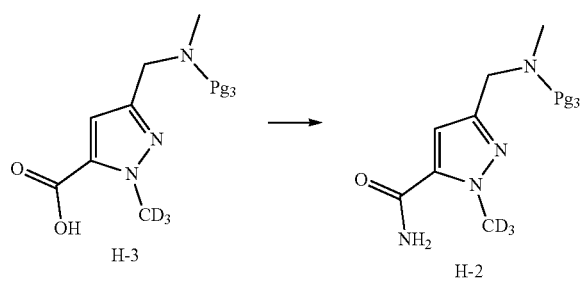

wherein Pg$_3$ is an amino-protecting group such as Cbz, Boc, Fmoc, Alloc, Teoc, methoxycarbonyl, ethoxycarbonyl, Ms, Ns, Ts, or Tf; or alternatively, Pg$_3$ is Boc.

In some embodiments, the method is performed in the presence of a condensation acylating agent; alternatively, wherein the condensation acylating agent is selected from alkyl chloroformate (for example, ethyl chloroformate, isobutyl chloroformate), oxalyl chloride, CDI, MsCl, TsCl, NsCl, and Boc$_2$O; alternatively, the condensation acylating agent is Boc$_2$O; alternatively, wherein the condensation acylating agent is oxalyl chloride or CDI: alternatively, wherein the condensation acylating agent is ethyl chloroformate; optionally, wherein a base selected from organic amine bases, inorganic metal bases and organic metal bases is used; alternatively, wherein the organic amine base is selected from DIPEA, TEA, NMM, DBU, DMAP, pyridine, 2,6-lutidine, and 2,2,6,6-tetramethylguanidine; alternatively, wherein the inorganic metal base is selected from sodium hydroxide, potassium hydroxide, lithium hydroxide, cesium hydroxide, sodium carbonate, potassium carbonate, cesium carbonate, sodium bicarbonate, and potassium bicarbonate: alternatively, wherein the organic metal base is selected from sodium hydride, potassium hydride, calcium hydride, sodium methoxide, sodium ethoxide, sodium tert-butoxide, potassium tert-butoxide, lithium tert-butoxide, and aluminum isopropoxide; or alternatively, wherein the base is TEA. Alternatively, the method is performed using CDI and ammonia gas.

In some embodiments, the method is performed in a solvent; alternatively, wherein the solvent is selected from DCM, DCE, tetrahydrofuran, acetonitrile, chloroform, DMF, DMA, and NMP: alternatively, wherein the solvent is selected from DCM and tetrahydrofuran; alternatively, wherein the solvent is tetrahydrofuran.

In some embodiments, the method is performed at a temperature of about −20° C. to about 100° C.; alternatively, about 0° C. to about 70° C.: or alternatively, about 0° C.

In one embodiment, the present disclosure provides a method of reacting a compound of formula (H-2) with a dehydrating condensing agent to form a compound of formula (H-1):

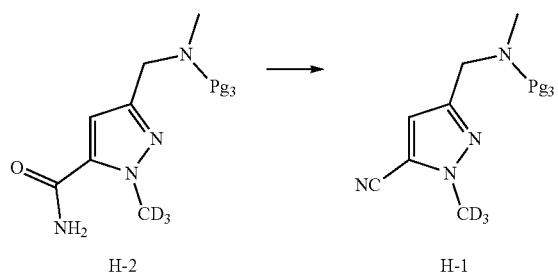

wherein Pg$_3$ is an amino-protecting group such as Cbz, Boc, Fmoc, Alloc, Teoc, methoxycarbonyl, ethoxycarbonyl, Ms, Ns, Ts, or Tf; or alternatively, Pg$_3$ is Boc.

In some embodiments, the dehydrating condensing agent in the method is selected from acetic anhydride, trifluoroacetic anhydride, oxalyl chloride, phosphorus oxychloride, and thionyl chloride; or alternatively, the dehydrating condensing agent is trifluoroacetic anhydride.

In some embodiments, the reaction conditions of the method further include an organic amine base; alternatively, wherein the organic amine base is selected from DIPEA, TEA, NMM, DBU, DMAP, pyridine, 2,6-lutidine, and 2,2,6,6-tetramethylguanidine; or yet alternatively, the organic amine base is TEA.

In some embodiments, the reaction conditions of the method further include a solvent; alternatively, wherein the solvent is selected from DCM, DCE, tetrahydrofuran, 2-methyltetrahydrofuran: or alternatively, wherein the solvent is DCM.

In some embodiments, the method is performed at a temperature of about −20° C. to about 50° C.: alternatively, about −10° C. to about 25° C.: or alternatively, about −10° C. to about 0° C.

In one embodiment, the present disclosure provides a method of reacting a compound of formula (H-1) with an acid to form a compound of formula (H):

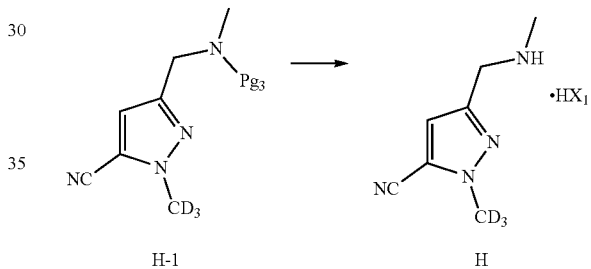

wherein Pg$_3$ is an amino-protecting group such as Cbz, Boc, Fmoc, Alloc, Teoc, methoxycarbonyl, ethoxycarbonyl, Ms, Ns, Ts, or Tf; or alternatively, Pg$_3$ is Boc.

In some embodiments, the method comprises removing the protecting group Pg$_3$ under the effect of an acid to form an amine, and then reacting with an alcoholic solution of hydrogen halide to form a salt.

In some embodiments, the acid in the method is selected from hydrochloric acid, sulfuric acid, trifluoroacetic acid, acetic acid, mercaptoacetic acid, trifluoroacetic acid, acetic acid, p-toluenesulfonic acid, benzenesulfonic acid, and formic acid; alternatively, wherein the acid is an alcoholic solution of hydrogen halide: alternatively, the alcoholic solution of hydrogen halide is selected from a solution of HCl in ethyl acetate, a solution of HCl in methanol, a solution of HCl in isopropanol, a solution of HBr in methanol, and a solution of HBr in isopropanol; alternatively, wherein the acid is a solution of HCl in isopropanol; alternatively, a solution of HCl in ethyl acetate; alternatively, wherein the acid is mercaptoacetic acid; optionally, wherein a base selected from organic amine bases, inorganic metal bases and organic metal bases is used; alternatively, wherein the organic amine base is selected from DIPEA, TEA, NMM, DBU, DMAP, pyridine, 2,6-lutidine, and 2,2,6,6-tetramethylguanidine; alternatively, wherein the inorganic metal base is selected from sodium hydroxide, potassium hydroxide, lithium hydroxide, cesium hydroxide, sodium carbonate, potassium carbonate, cesium carbonate, sodium bicarbonate, and potassium bicarbonate; alternatively, wherein the organic metal base is selected from sodium hydride, potassium hydride, calcium hydride, sodium methoxide, sodium ethoxide, sodium tert-butoxide, potassium tert-butoxide, lithium tert-butoxide, and aluminum isopropoxide; or alternatively, wherein the base is selected from sodium carbonate, potassium carbonate, and cesium carbonate.

In some embodiments, the method is performed at a temperature of about −20° C. to about 50° C.; alternatively, about −10° C. to about 25° C.; or alternatively, room temperature.

Reaction route 4 represents an exemplary synthesis of a compound of formula (H), and can be performed according to the embodiments described herein. The specific reaction conditions and reagents used in reaction route 4 are discussed below.

Reaction Route 4

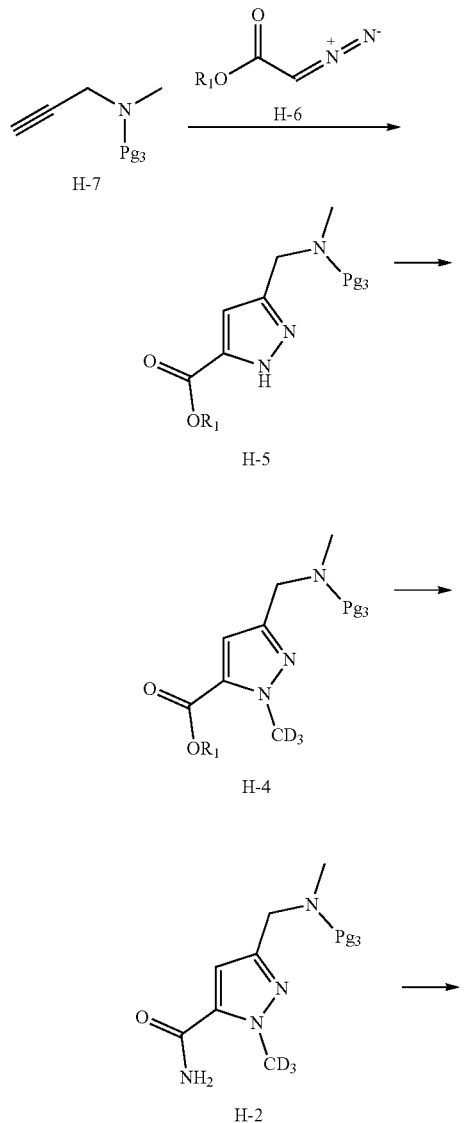

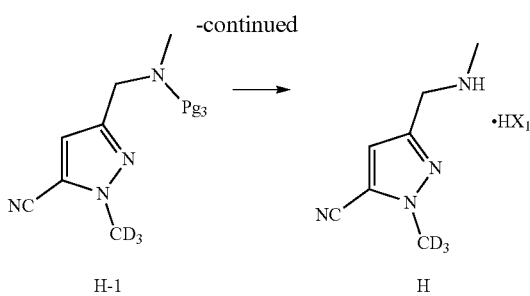

In reaction route 4, in addition to the same method as in reaction route 3, the present disclosure also provides a method of reacting a compound of formula (H-4) with ammonia water to form a compound of formula (H-2):

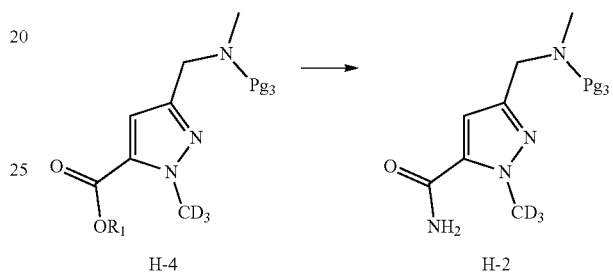

wherein $R_1$ is $C_{1-6}$ alkyl, $Pg_3$ is an amino-protecting group such as Cbz, Boc, Fmoc, Alloc, Teoc, methoxycarbonyl, ethoxycarbonyl, Ms, Ns, Ts, or Tf.

In some embodiments, the reaction conditions of the method include a solvent; alternatively, wherein the solvent is selected from methanol, ethanol, isopropanol, isobutanol, and tert-butanol: or alternatively, wherein the solvent is methanol.

In some embodiments, the method is performed under sealed conditions.

In some embodiments, the reaction conditions of the method further include a temperature of about 50° C. to about 120° C.; or alternatively, about 60° C. to about 90° C.

Reaction route 5 represents an exemplary synthesis of a compound of formula (E-b), and can be performed according to the embodiments described herein. The specific reaction conditions and reagents used in reaction route 5 are discussed below.

Reaction Route 5

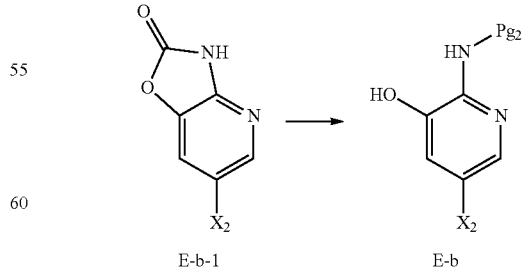

In another aspect, the present disclosure provides a method of alkoxycarbonylating a compound of formula (E-b-1) to form a compound of formula (E-b):

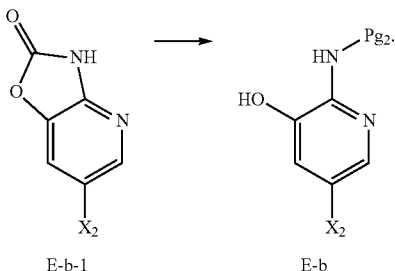

E-b-1    E-b

In some embodiments, $Pg_2$ is an amino-protecting group such as Cbz, Boc, Fmoc, Alloc, Teoc, methoxycarbonyl, or ethoxycarbonyl; or alternatively, $Pg_2$ is Boc.

In some embodiments, $X_2$ is selected from halogen; alternatively, $X_2$ is selected from Cl, Br, and I; or alternatively, $X_2$ is Br.

In some embodiments, the reaction conditions of the method include an amino-protecting agent, a nucleophilic catalyst and a base; alternatively, wherein the amino-protecting agent is selected from Cbz-Cl, $Boc_2O$, Fmoc-Cl, Alloc-Cl, Teoc-Cl, methyl chloroformate, and ethyl chloroformate: alternatively, wherein the amino-protecting agent is $Boc_2O$; alternatively, wherein the nucleophilic catalyst is DMAP: alternatively, wherein the base is selected from organic amine bases and inorganic metal bases; alternatively, wherein the organic amine base is selected from DIPEA. TEA, NMM, DBU, DMAP, pyridine, 2,6-lutidine, and 2,2,6,6-tetramethylguanidine; alternatively, wherein the inorganic metal base is selected from sodium hydroxide, potassium hydroxide, lithium hydroxide, cesium hydroxide, sodium carbonate, potassium carbonate, cesium carbonate, sodium bicarbonate, and potassium bicarbonate; alternatively, wherein the organic metal base is selected from sodium hydride, potassium hydride, calcium hydride, sodium methoxide, sodium ethoxide, sodium tert-butoxide, potassium tert-butoxide, lithium tert-butoxide, and aluminum isopropoxide; or alternatively, the base is TEA In some embodiments, the method is performed in the presence of a solvent, such as an aprotic solvent or a mixture thereof: alternatively, wherein the solvent is selected from DCM, DCE, ethyl acetate, methyl acetate, isopropyl acetate, n-hexane, n-heptane, petroleum ether, acetone, acetonitrile, toluene, methyl tert-butyl ether, tetrahydrofuran, 2-methyltetrahydrofuran, 1,4-dioxane, ethylene glycol monomethyl ether, ethylene glycol dimethyl ether, DMF, DMA, and DMSO: or alternatively, wherein the solvent is DCM.

In some embodiments, the method is performed at a temperature of –20° C. to 50° C.: or alternatively, about 0° C. to 25° C.

In another aspect, the present disclosure provides the following reaction route 6 for preparing the compound of formula (H-5):

Reaction Route 6

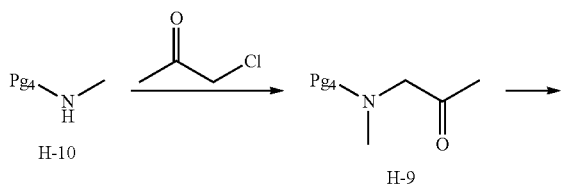

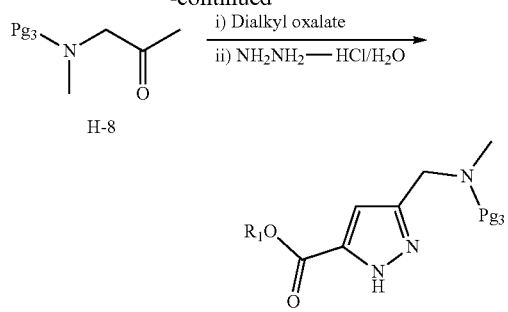

H-8

H-5

In one embodiment, the present disclosure provides a method for converting a compound of formula (H-10) into a compound of formula (H-9):

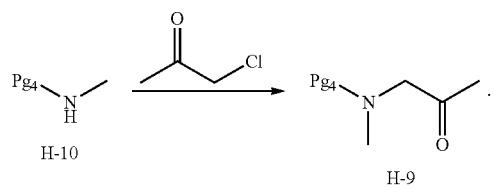

In some embodiments, $Pg_4$ is an amino-protecting group such as Bn, Cbz, Fmoc, Alloc, Teoc, methoxycarbonyl, or ethoxycarbonyl; or alternatively, $Pg_4$ is Bn.

In some embodiments, the method is performed in the presence of an organic amine base, an inorganic metal base or an organic metal base: alternatively, wherein the organic amine base is selected from DIPEA, TEA, NMM, DBU, DMAP, pyridine, 2,6-lutidine, and 2,2,6,6-tetramethylguanidine; alternatively, wherein the inorganic metal base is selected from sodium hydroxide, potassium hydroxide, lithium hydroxide, cesium hydroxide, sodium carbonate, potassium carbonate, cesium carbonate, sodium bicarbonate, and potassium bicarbonate; alternatively, wherein the organic metal base is selected from sodium hydride, potassium hydride, calcium hydride, sodium methoxide, sodium ethoxide, sodium tert-butoxide, potassium tert-butoxide, lithium tert-butoxide, and aluminum isopropoxide; or alternatively, wherein the base is DIPEA.

In some embodiments, the method is performed in a solvent; alternatively, wherein the solvent is selected from DCM, DCE, tetrahydrofuran, acetonitrile, chloroform, DMF, DMA, and NMP; or alternatively, wherein the solvent is acetonitrile.

In some embodiments, the method is performed at a temperature of about –20° C. to about 50° C.: or alternatively, about 0° C. to about room temperature.

In another embodiment, the present disclosure provides a method of converting a compound of formula (H-9) into a compound of formula (H-8):

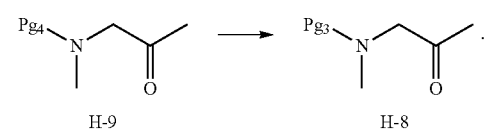

In some embodiments, $Pg_4$ is an amino-protecting group such as Bn, Cbz, Fmoc, Alloc, Teoc, methoxycarbonyl, or ethoxycarbonyl; or alternatively, $Pg_4$ is Bn.

In some embodiments, $Pg_3$ is an amino-protecting group such as Cbz, Boc, Fmoc, Alloc, Teoc, methoxycarbonyl, ethoxycarbonyl, Ms, Ns, Ts, or Tf; or alternatively, $Pg_3$ is Boc.

In some embodiments, removal of $Pg_4$ followed by protection by $Pg_3$ is performed when $Pg_4$ is different from $Pg_3$. Alternatively, when $Pg_4$ is Bn, the removal reaction is performed by reacting with hydrogen gas in the presence of a Pd catalyst selected from Pd/C, $Pd(OH)_2$, etc; the reaction conditions include a solvent: alternatively, wherein the solvent is selected from methanol, ethanol, isopropanol, isobutanol, and tert-butanol; or alternatively, wherein the solvent is ethanol.

In some embodiments, the protection by $Pg_3$ is performed in the presence of an amino-protecting agent and a base: alternatively, wherein the amino-protecting agent is selected from Cbz-Cl, $Boc_2O$, Fmoc-Cl, Alloc-Cl, Teoc-Cl, methyl chloroformate, and ethyl chloroformate; alternatively, wherein the amino-protecting agent is $Boc_2O$: alternatively, wherein the base is selected from organic amine bases and inorganic metal bases: alternatively, wherein the organic amine base is selected from DIPEA, TEA, NMM, DBU, DMAP, pyridine, 2,6-lutidine, and 2,2,6,6-tetramethylguanidine; alternatively, wherein the inorganic metal base is selected from sodium carbonate, potassium carbonate, cesium carbonate, sodium bicarbonate, potassium bicarbonate, sodium hydroxide, potassium hydroxide, lithium hydroxide, and cesium fluoride; alternatively, wherein the base is TEA; or alternatively, wherein the base is DIPEA.

In some embodiments, the protection by $Pg_3$ is performed in the presence of a nucleophilic catalyst; alternatively, wherein the nucleophilic catalyst is DMAP.

In some embodiments, the protection by $Pg_3$ is performed in the presence of a solvent, such as an aprotic solvent or a mixture thereof: alternatively, wherein the solvent is selected from DCM, DCE, ethyl acetate, methyl acetate, isopropyl acetate, n-hexane, n-heptane, petroleum ether, acetone, acetonitrile, toluene, methyl tert-butyl ether, tetrahydrofuran, 2-methyltetrahydrofuran, 1,4-dioxane, ethylene glycol monomethyl ether, ethylene glycol dimethyl ether, DMF, DMA, and DMSO: or alternatively, wherein the solvent is DCM.

In some embodiments, the method is performed at a temperature of about −20° C. to reflux temperature: alternatively, about 25° C. to reflux temperature: or alternatively, about 30° C.

In some embodiments, the removal reaction of $Pg_4$ and the protection reaction by $Pg_3$ are a one-pot reaction, that is, the conditions of the removal reaction of $Pg_4$ are used, except that a protecting reagent of $Pg_3$, such as $Boc_2O$, is added to the reaction at the same time.

In another embodiment, the present disclosure provides a method of cyclizing a compound of formula (H-8) to form a compound of formula (H-5):

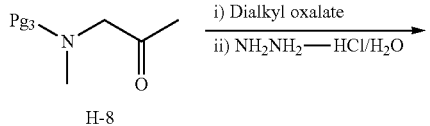

H-8 i) Dialkyl oxalate
ii) $NH_2NH_2$—$HCl/H_2O$

-continued

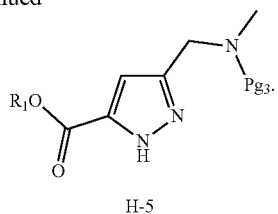

H-5

In some embodiments, $R_1$ is $C_{1-6}$alkyl; alternatively, $R_1$ is $C_{1-4}$alkyl; alternatively, $R_1$ is selected from methyl, ethyl, isopropyl, isobutyl, and tert-butyl; or alternatively. $R_1$ is ethyl.

In some embodiments, the cyclization reaction is performed in the presence of dialkyl oxalate and hydrazine hydrochloride.

In some embodiments, the method is performed in the presence of an organic amine base, an inorganic metal base or an organic metal base; alternatively, wherein the organic amine base is selected from DIPEA, TEA, NMM, DBU, DMAP, pyridine, 2,6-lutidine, and 2,2,6,6-tetramethylguanidine; alternatively, wherein the inorganic metal base is selected from sodium hydroxide, potassium hydroxide, lithium hydroxide, cesium hydroxide, sodium carbonate, potassium carbonate, cesium carbonate, sodium bicarbonate, and potassium bicarbonate; alternatively, wherein the organic metal base is selected from sodium hydride, potassium hydride, calcium hydride, sodium methoxide, sodium ethoxide, sodium tert-butoxide, potassium tert-butoxide, lithium tert-butoxide, and aluminum isopropoxide; or alternatively, wherein the base is sodium ethoxide.

In some embodiments, the reaction conditions of the method include a solvent; alternatively, wherein the solvent is selected from methanol, ethanol, isopropanol, isobutanol, and tert-butanol; or alternatively, wherein the solvent is ethanol.

In some embodiments, the method is performed at a temperature of about −20° C. to room temperature; alternatively, about 0° C. to room temperature; or alternatively, room temperature.

EXAMPLE

The compounds disclosed herein can be prepared using the methods disclosed herein and conventional variants obvious in view of this application as well as methods known in the art. In addition to the methods taught in this application, conventional well-known synthesis methods can also be used. The synthesis of the compounds described herein can be achieved as described in the examples below. If commercially available, reagents can be purchased commercially, for example, from Saen Chemical Technology (Shanghai) Co., Ltd. or other chemical suppliers. Unless otherwise stated, the starting materials for the following reactions can be obtained from commercial sources.

Example 1: Synthesis of (S)-5-fluoro-3-methyl-isobenzofuran-1(3H)-one (Compound of Formula (J))

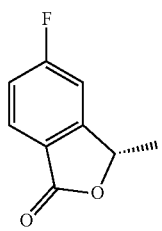

The following route was used for the synthesis.

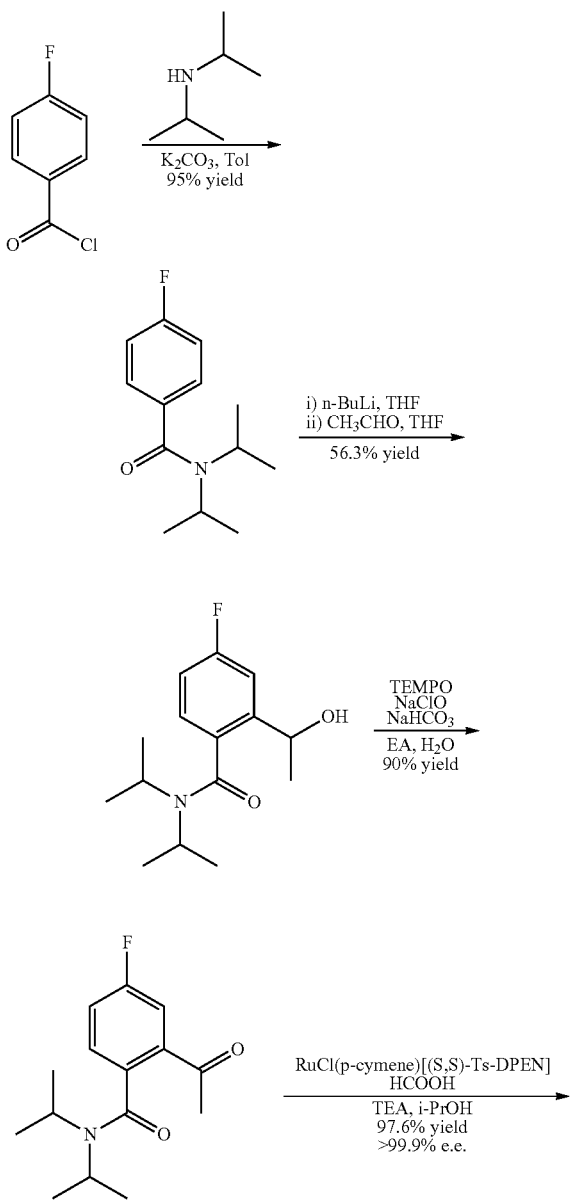

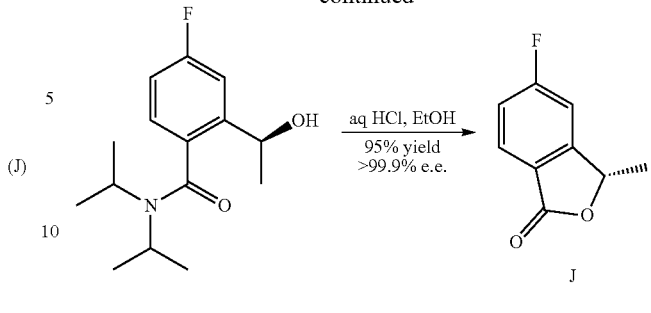

Step 1: 4-fluoro-N,N-diisopropylbenzamide

To a 3.0 L three-necked flask equipped with magnetic stirring were added potassium carbonate (165.6 g, 1.2 mol) and water (450 mL), and stirred until the solution became clear. Toluene (750 mL) and N,N-diisopropylamine (121.2 g, 1.2 mol) were added. The mixture was cooled in an ice-water bath, and p-fluorobenzoyl chloride (158.56 g, 1.0 mol) was added dropwise while maintaining the temperature not higher than 10° C. After the addition was completed, the ice bath was removed, and the mixture was reacted with stirring at room temperature for 2 h. The organic layer was separated, and the aqueous phase was extracted with ethyl acetate (300 mL×2). The organic phases were combined, washed successively with water (200 mL) and then saturated brine (200 mL), dried over anhydrous sodium sulfate, and filtered. The filtrate was concentrated to dryness under reduced pressure. To the residue was added petroleum ether (1.0 L), and the mixture was heated to reflux with stirring. Petroleum ether was then slowly added until the mixture just became clear. The heating was stopped, and the mixture was allowed to slowly cool to room temperature overnight to crystallize. The mixture was filtered, and washed with petroleum ether (100 mL). The filter cake was dried in vacuum to give 212 g of a white crystal in a yield of 95%, and a purity (HPLC) of >95%. $^1$H NMR (400 MHz, CDCl$_3$) δ (ppm): 7.34-7.30 (m, 2H), 7.11-7.05 (m, 2H), 3.69 (br s, 2H), 1.35 (br s, 12H).

Step 2: 4-fluoro-2-(1-hydroxyethyl)-N,N-diisopropylbenzamide

To a 2.0 L three-necked flask equipped with magnetic stirring was added anhydrous THF (180 mL) under nitrogen atmosphere, and cooled to −70° C. A solution of n-butyllithium in n-hexane (2.5 M, 180 mL, 0.45 mol) was added. A solution of 4-fluoro-N,N-diisopropylbenzamide (66.9 g, 0.3 mol) in anhydrous THF (420 mL) was slowly added dropwise over 1 hour, and the mixture was reacted with stirring at this temperature for 2 hours. A solution of acetaldehyde in tetrahydrofuran (5 M, 90 mL, 0.45 mol) was slowly added dropwise over 1.5 hours. After the dropwise addition was completed, the mixture was reacted with stirring at this temperature for another 2 hours. By TLC (PE:EA=3:1) and HPLC monitoring, the reaction was completed. The reaction was quenched by adding saturated aqueous ammonium chloride (200 mL). The layers were separated, and the aqueous phase was extracted with ethyl acetate (100 mL×2). The organic phases were combined, washed with saturated brine (80 mL×2), dried over anhydrous sodium sulfate, and filtered. The filtrate was concentrated to dryness under reduced pressure. To the residue were added petroleum ether (800 mL) and ethyl acetate (100 mL). The mixture was heated to reflux with stirring and just became clear. The mixture was then allowed to slowly cool overnight to crystallize. The mixture was then filtered, and washed with petroleum ether (30 mL). The filter cake was dried in vacuo to give 45 g of a white solid in a yield of 56.3% and a purity (HPLC) of >95%. $^1$H NMR (400 MHz, CDCl$_3$) δ (ppm): 7.27-7.17 (m, 1H), 7.14-7.10 (m, 1H), 7.01-6.96 (m, 1H), 4.88-4.84 (m, 1H), 3.84-3.76 (m, 1H), 3.57-3.52 (m, 1H), 1.61-1.52 (m, 9H), 1.20-1.11 (m, 6H).

Step 3: 2-acetyl-4-fluoro-N,N-diisopropylbenzamide

To a 1.0 L three-necked flask equipped with magnetic stirring were added 4-fluoro-2-(1-hydroxyethyl)-N,N-diisopropylbenzamide (53 g, 198.5 mmol) and ethyl acetate (250 mL) under nitrogen atmosphere, and stirred until the solution became clear. A solution of NaHCO$_3$ (16.8 g, 200 mmol) in water (150 mL) was added, and the mixture was cooled to 0° C. in an ice-water bath. TEMPO (1.24 g, 8 mmol) was added, and then an aqueous solution of sodium hypochlorite (14% available chlorine, 231 g, 456.6 mmol) was slowly added dropwise. After the addition was completed, the ice bath was removed, and the mixture was reacted with stirring at room temperature for 3 hours. By HPLC monitoring, the reaction was completed. The reaction was quenched by adding a saturated aqueous solution of sodium sulfite (100 mL). The mixture was stirred for 20 min. The organic layer was separated, and the aqueous phase was extracted with ethyl acetate (100 mL×2). The organic phases were combined, washed successively with water (100 mL) and then saturated brine (100 mL), dried over anhydrous sodium sulfate, and filtered. The filtrate was concentrated to dryness under reduced pressure. To the residue were added petroleum ether (500 mL) and ethyl acetate (50 mL). The mixture was crystallized to give 48 g of a white solid in a yield of 90% and a purity (HPLC) of >95%. $^1$H NMR (400 MHz, CDCl$_3$) δ (ppm): 7.49 (dd, J=9.2 Hz, J=2.4 Hz, 1H), 7.27-7.21 (m, 2H), 3.57-3.51 (m, 2H), 2.60 (s, 3H), 1.59 (d, J=6.8 Hz, 6H), 1.13 (d, J=6.8 Hz, 6H).

Step 4: (S)-4-fluoro-2-(1-hydroxyethyl)-N,N-diisopropylbenzamide

To a 1.0 L three-necked flask equipped with magnetic stirring were added 2-acetyl-4-fluoro-N,N-diisopropylbenzamide (43 g, 162 mmol) and isopropanol (400 mL), and stirred until the solution became clear. RuCl(p-cymene)[(S,S)-Ts-DPEN](0.5 g, 0.8 mmol) was added. The system was evacuated with suction and protected with nitrogen gas. Formic acid (32 g, 697 mmol) and then triethylamine (41 g, 405 mmol) were successively added dropwise under nitrogen atmosphere. The mixture was heated to 50° C.-55° C. and reacted with stirring at this temperature for 3 hours. By HPLC monitoring, the reaction was completed. The mixture was cooled to room temperature, and filtered to remove insoluble solids. The filtrate was concentrated to dryness under reduced pressure. The residue was recrystallized from petroleum ether/ethyl acetate (20/2) to give 42 g of an off-white solid in a yield of 97.6% and a purity (HPLC) of >95% (ee>99.9%). $^1$H NMR (400 MHz, CDCl$_3$) δ (ppm): 7.27-7.17 (m, 1H), 7.14-7.10 (m, 1H), 7.01-6.96 (m, 1H), 4.88-4.84 (m, 1H), 3.84-3.76 (m, 1H), 3.57-3.52 (m, 1H), 1.61-1.52 (m, 9H), 1.20-1.11 (m, 6H).

Step 5: Synthesis of (S)-5-fluoro-3-methylisobenzofuran-1(3H)-one

To a 1.0 L single-necked flask equipped with magnetic stirring were added (S)-4-fluoro-2-(1-hydroxyethyl)-N,N-diisopropylbenzamide (42 g, 157 mmol) and ethanol (210 mL), and stirred until the solution became clear. An aqueous solution of hydrochloric acid (13.5%, 126 g) was added. The mixture was heated to 50° C. under nitrogen atmosphere, and reacted with stirring at this temperature overnight. By TLC (PE:EA=5:1) and HPLC monitoring, the reaction was completed. The reaction solution was cooled to room temperature, and then evaporated under reduced pressure to remove the organic solvent. A large amount of a white solid was precipitated out. The precipitated solid was filtered, washed with water (30 mL), and dried in vacuum to give 23.2 g of a white powder in a yield of 85.4% and a purity (HPLC) of >95% (ee>99.9%). $^1$H NMR (400 MHz, CDCl$_3$) δ (ppm): 7.92-7.89 (m, 1H), 7.26-7.21 (m, 1H), 7.12 (dd, J=7.6 Hz, J=2.0 Hz, 1H), 5.54 (q, J=7.6 Hz, 1H), 1.65 (d, J=7.6 Hz, 3H).

Example 2: Alternative synthesis of (S)-5-fluoro-3-methylisobenzofuran-1(3H)-one (Compound of Formula (J))

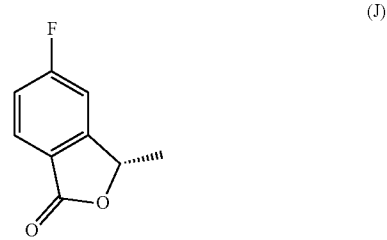

(J)

The following route was used for the synthesis:

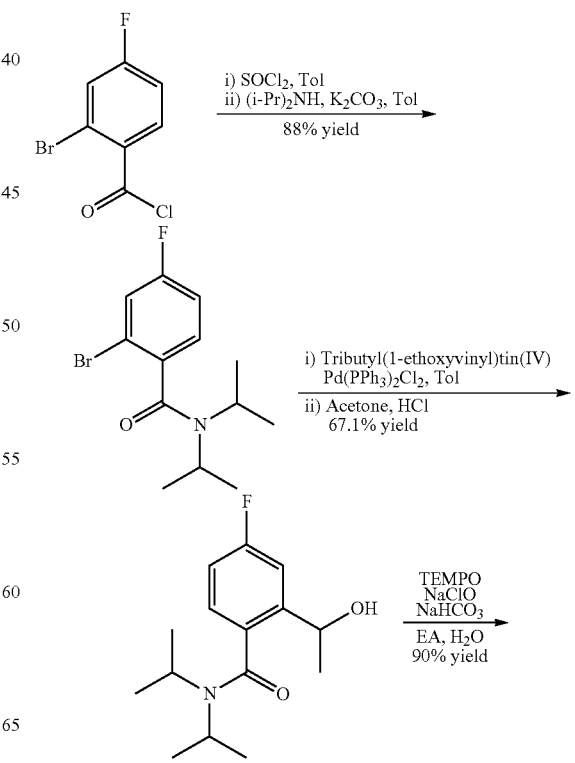

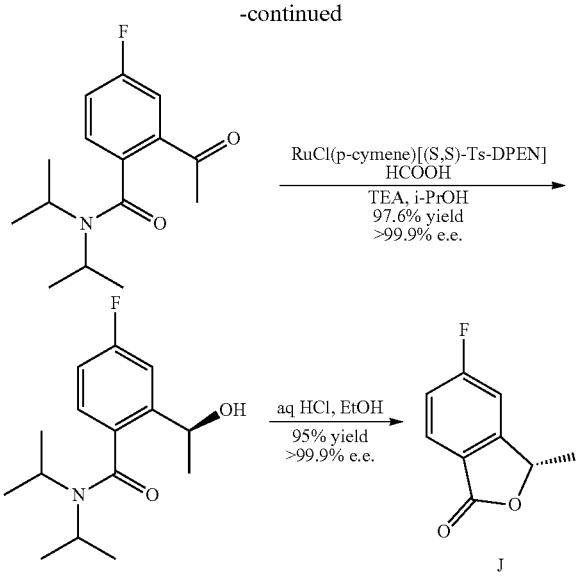

Step 1: Synthesis of 2-bromo-4-fluoro-N,N-diisopropylbenzamide

To a 1.0 L three-necked flask equipped with magnetic stirring were added 2-bromo-4-fluorobenzoic acid (70 g, 0.32 mol) and anhydrous toluene (200 mL), and stirred until the solution became clear. Thionyl chloride (152 g, 1.28 mol) was added, and the mixture was heated to reflux (exhaust gas was absorbed by NaOH solution). The reaction solution was reacted under reflux for 2 hours. The reaction solution was then evaporated under reduced pressure to remove toluene and excess thionyl chloride to give 2-bromo-4-fluorobenzoyl chloride for further use.

To another 1.0 L three-necked flask equipped with magnetic stirring were added potassium carbonate (53 g, 0.384 mol) and water (180 ml), and stirred until the solution became clear. N,N-diisopropylamine (38.8 g, 0.384 mol) and toluene (300 ml) were added. The newly prepared 2-bromo-4-fluorobenzoyl chloride was added dropwise over about 0.5 hours, and the mixture was reacted with stirring at room temperature for 2 h. The organic layer was separated, and the aqueous phase was extracted with ethyl acetate (300 mL×2). The organic phases were combined, washed successively with water (200 mL) and then saturated brine (200 mL), dried over anhydrous sodium sulfate, and filtered. The filtrate was concentrated to dryness under reduced pressure to give 88 g of a white solid in a yield of 86% and a purity (HPLC) of >95%, LC-MS (APCI): m/z=302 (M+1)$^+$.

Step 2: Synthesis of 2-acetyl-4-fluoro-N,N-diisopropylbenzamide

To a 1.0 L three-necked flask equipped with magnetic stirring were added 2-bromo-4-fluoro-N,N-diisopropylbenzamide (40.2 g, 126.4 mmol) and anhydrous toluene (400 mL), and stirred until the solution became clear. Tributyl(1-ethoxyvinyl)tin (59.4 g, 164.3 mmol) and Pd(PPh$_3$)$_2$Cl$_2$ (1.75 g, 2.5 mmol) were added, and the mixture was heated to 100° C. under nitrogen atmosphere and reacted with stirring at this temperature for 2 hours. TLC (EA:PE=1:5) showed that the reaction was completed. An aqueous solution of potassium fluoride (60 g/200 mL) was added, and the mixture was reacted with stirring for 30 minutes. The reaction solution was filtered. The filter cake was washed with ethyl acetate, and the organic phase was separated from the filtrate, and concentrated to dryness under reduced pressure. The residue was added to acetone (300 mL), and stirred until the solution became clear. 3 mol/L of hydrochloric acid (150 ml) was added dropwise. The mixture was reacted to with stirring at room temperature for 1 h. TLC (EA:PE=1:5) showed that the reaction was completed. The reaction solution was evaporated under reduced pressure to remove acetone, and adjusted to a pH of >7 with sodium bicarbonate. The mixture was extracted with ethyl acetate (300 mL×2). The organic phases were combined, washed with saturated sodium bicarbonate solution (200 ml), water (200 mL), and then saturated brine (200 mL), dried over anhydrous sodium sulfate, and filtered. The filtrate was concentrated to dryness under reduced pressure, and the residue was purified by silica gel column chromatography to give 23 g of a white solid in a yield of 67.1% and a purity (HPLC) of >95%. LC-MS (APCI): m/z=266.1 (M+1)$^+$, $^1$H NMR (400 MHz, CDCl$_3$) δ (ppm): 7.49 (dd, J=9.2 Hz, J=2.4 Hz, 1H), 7.27-7.21 (m, 2H), 3.57-3.51 (m, 2H), 2.60 (s, 3H), 1.59 (d, J=6.8 Hz, 6H), 1.13 (d, J=6.8 Hz, 6H).

Step 3: Synthesis of (S)-4-fluoro-2-(1-hydroxyethyl)-N,N-diisopropylbenzamide; and

Step 4: Synthesis of (S)-5-fluoro-3-methylisobenzofuran-1(3H)-one, which can be Synthesized According to the Method of Step 4 and Step 5 in Example 1

Example 3: Synthesis of tert-butyl (5-bromo-3-hydroxypyridin-2-yl)carbamate (Compound of Formula (E-b))

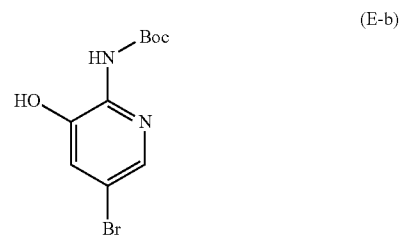 [SMILES: CC(C)(C)OC(=O)Nc1ncc(Br)cc1O]

The following route was used for the synthesis:

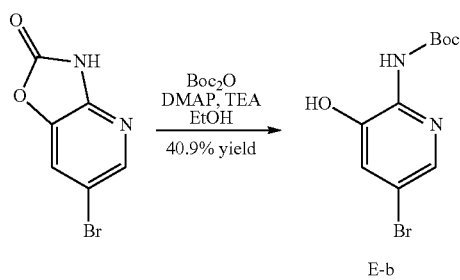 [SMILES: O=c1[nH]c2ncc(Br)cc2o1 ; "40.9% yield" ; "Boc2ODMAP, TEAEtOH" ; CC(C)(C)OC(=O)Nc1ncc(Br)cc1O]

To a 2.0 L single-necked flask equipped with magnetic stirring were added 6-bromo-oxazolo[4,5-b]pyridine-2(3H)-one (100 g, 467 mmol) and ethanol (500 mL). Triethylamine (70.8 g, 701 mmol) and DMAP (5.7 g, 46.7 mmol) were added with stirring and further stirred until the solution became clear. Boc₂O (132 g, 607 mmol) was added, and the mixture was reacted with stirring at room temperature under nitrogen atmosphere overnight. The reaction solution was evaporated under reduced pressure to remove the solvent, and the residue was purified by silica gel column chromatography to give 55 g of a white solid in a yield of 40.9%. ¹H NMR (300 MHz, DMSO-D₆) δ (ppm): 10.44 (s, 1H), 8.88 (s, 1H), 7.91 (d, J=2.1 Hz, 1H), 7.3 (d, J=2.1 Hz, 1H), 1.43 (s, 9H).

Example 4: Synthesis of 1-(methyl-d₃)-3-((methylamino)methyl)-5-cyano-1H-pyrazole (Compound of Formula (H))

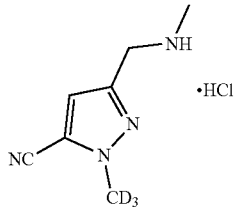

(H)

The following route was used for the synthesis:

Reaction of the Compound of Formula (H-7-a) with the Compound of Formula (H-6) to Form the Compound of Formula (H-5-b):

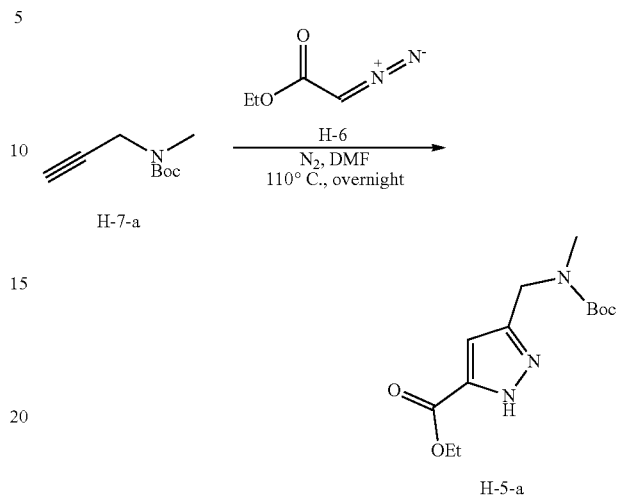

To a 500 mL single-necked flask equipped with magnetic stirring were added a compound of formula (H-7-a) (120 g, 0.71 mol) and DMF (150 mL), and stirred until the solution became homogeneous. The compound of formula (H-6)

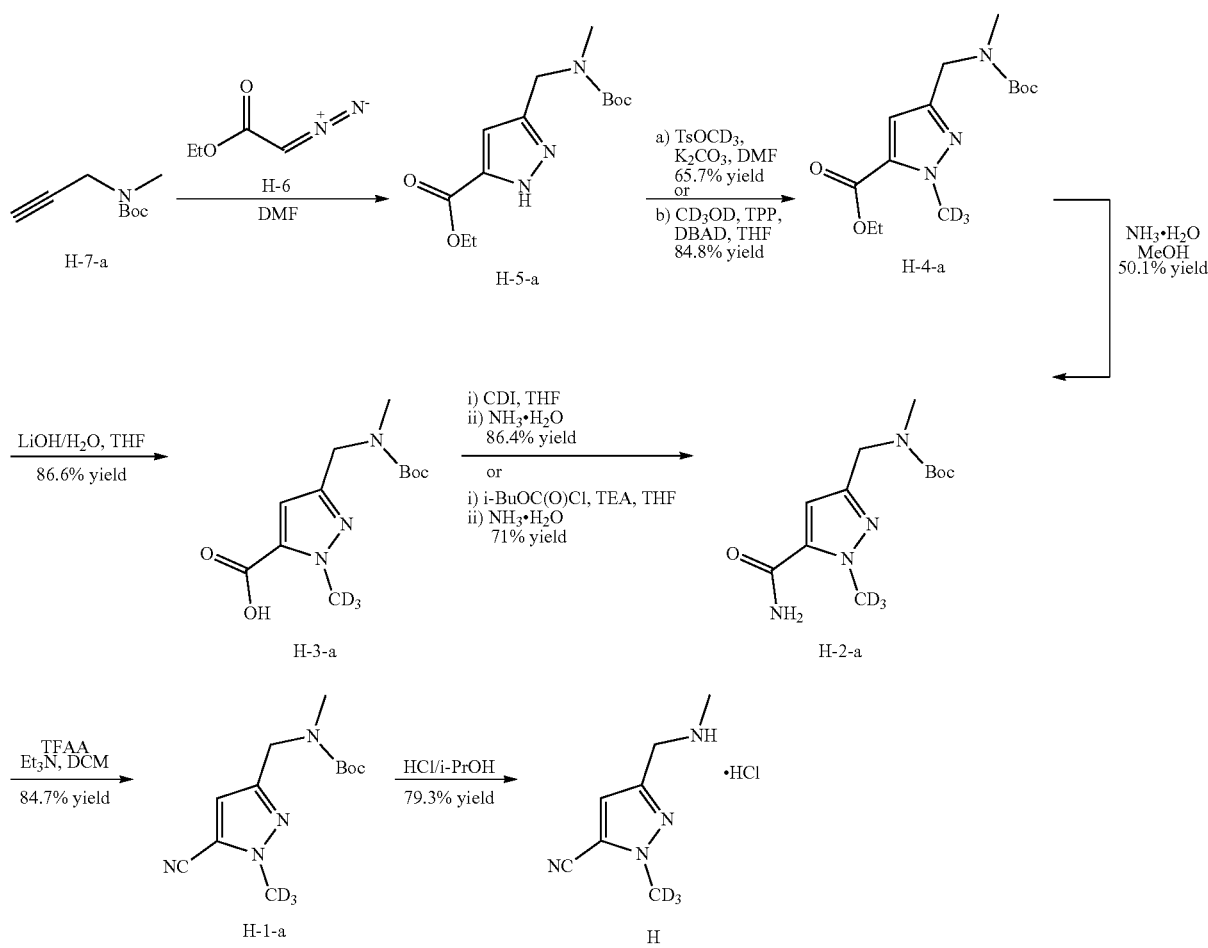

(76.9 g, 0.67 mol) was added. The mixture was heated to 110° C. under nitrogen atmosphere and reacted with stirring at this temperature overnight. By TLC (PE:EA=5:1) and HPLC monitoring, the reaction was completed. The reaction solution was cooled to room temperature, and was used directly in the next step.

Deuterated-Methylation of the Compound of Formula (H-5-a) to Form the Compound of Formula (H-4-a):

Method 1

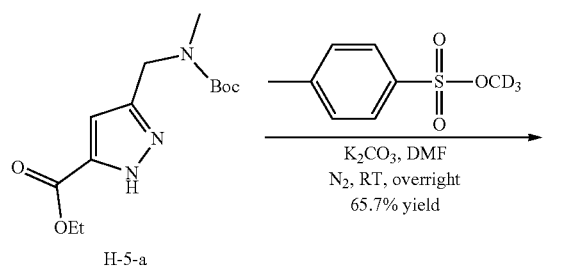

To a 3 L single-necked flask equipped with magnetic stirring was added a solution of the compound of formula (H-5-a) in DMF, and then additional DMF (1200 mL) was added. The mixture was stirred until homogeneous. Potassium carbonate (147.0 g, 1.07 mol) and then TsOCD₃ (161.0 g, 0.85 mol) were successively added, and the mixture was reacted with stirring at room temperature under nitrogen atmosphere overnight. By TLC (PE:EA=5:1) and HPLC monitoring, the reaction was completed. The reaction mixture was poured into water (4.0 L), and extracted with petroleum ether (1.0 L×3). The organic phases were combined, washed successively with water (2.0 L×3) and then saturated brine (500 mL), dried over anhydrous sodium sulfate, and filtered. The filtrate was concentrated under reduced pressure to give a brown oil, which was purified by silica gel column chromatography to give 140 g of a yellow oil in a two-step yield of 65.7% and a purity (HPLC) of >85%. ¹H NMR (400 MHz, CDCl₃) δ (ppm): 6.76 (s, 1H), 4.41 (s, 2H), 4.32 (q, J=6.8 Hz, 2H), 2.86 (s, 3H), 1.41 (s, 9H), 1.37 (t, J=6.8 Hz, 3H).

Method 2:

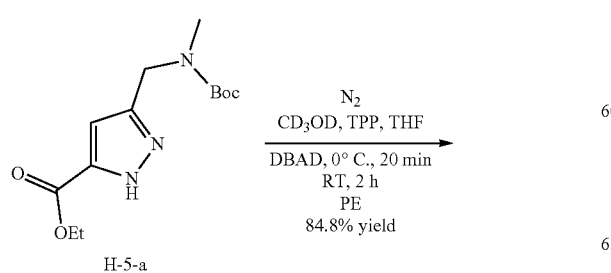

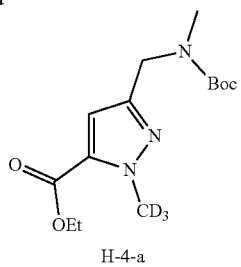

To a 500 mL three-necked flask equipped with magnetic stirring were added the compound of formula (H-5-a) (20 g, 70.7 mmol) and anhydrous THF (150 mL), and stirred until the solution became clear. Triphenylphosphine (18.5 g, 70.7 mmol) was added, and the system was evacuated with suction and purged with nitrogen gas three times. Deuterated methanol (3.84 g, 106 mmol) was added dropwise, and the mixture was cooled in an ice-water bath. A solution of di-tert-butyl azodicarboxylate (16.3 g, 70.7 mmol) in anhydrous THF (50 mL) was slowly added dropwise over 20 min. After the dropwise addition was completed, the ice bath was removed, and the reaction solution was reacted with stirring at room temperature under nitrogen atmosphere for 2 hours. TLC (PE:EA=5:1) showed that the reaction was completed. The reaction solution was evaporated under reduced pressure to remove the solvent, and the residue was added to petroleum ether (200 mL). The mixture was heated to reflux, stirred for 10 minutes, and then filtered to remove insoluble solids. The filter cake was washed with petroleum ether (10 mL), and the filtrate was concentrated to dryness. To the residue was added petroleum ether (50 mL), and the mixture was heated to reflux. Petroleum ether was slowly added dropwise to just dissolve the solid. The mixture was cooled slowly, and stirred at room temperature overnight. The mixture was filtered to remove a solid. The filter cake was washed with petroleum ether (10 mL), and the filtrate was concentrated under reduced pressure to give 18 g of a yellow oil in a yield of 84.8%.

Hydrolyzation of the Compound of Formula (H-4-a) to Form the Compound of Formula (H-3-a):

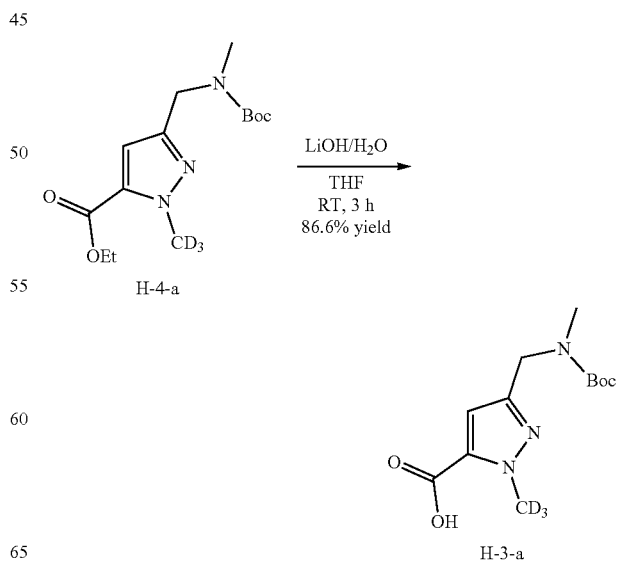

To a 3.0 L single-necked flask equipped with magnetic stirring were added the compound of formula (H-4-a) (140 g, 0.467 mol) and THF (700 mL), and stirred until the solution became homogeneous. A solution of LiOH—H$_2$O (39.2 g, 0.93 mol) in water (700 mL) was added, and the mixture was reacted with stirring at room temperature for 3 h. By TLC (PE:EA=5:1) and HPLC monitoring, the reaction was completed. The mixture was washed with petroleum ether (1000 mL), and the lower layer was separated. Solid NaHSO$_4$ was slowly added under ice-water bath to adjust the pH to about 3, and the mixture was extracted with ethyl acetate (600 mL×3). The organic phases were combined, washed with saturated brine (500 mL×2), dried over anhydrous sodium sulfate, and filtered. The filtrate was concentrated under reduced pressure to give 110 g of a white solid in a yield of 86.6% and a purity (HPLC) of >85%. $^1$H NMR (400 MHz, CDCl$_3$) δ (ppm): 6.83 (s, 1H), 4.41 (s, 2H), 2.88 (s, 3H), 1.41 (s, 9H).

Formation of an Amide Bond by a Method of Mixed Acid Anhydride to Form the Compound of Formula (H-2-a)

Method 1

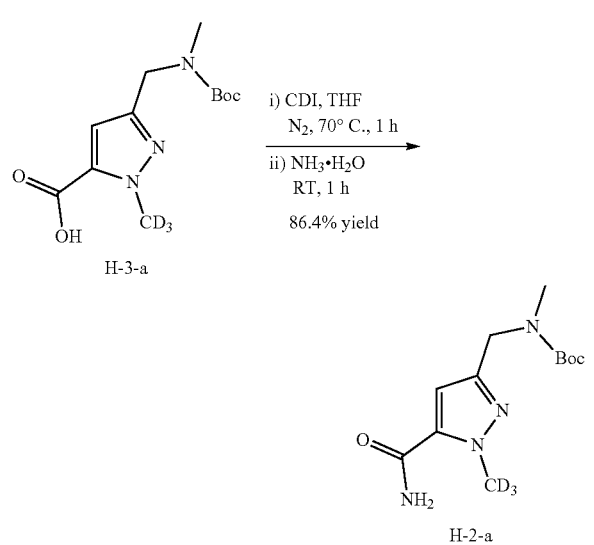

To a 2.0 L single-necked flask equipped with magnetic stirring were added the compound of formula (H-3-a) (110 g, 0.404 mol) and anhydrous THF (1100 mL), and stirred until the solution became homogeneous. CDI (131 g, 0.808 mol) was added, and the mixture was heated to 70° C. under nitrogen atmosphere and reacted with stirring at this temperature for 1 hour. The reaction solution was cooled to room temperature, and added to a constant pressure dropping funnel for further use. To another 3.0 L single-necked flask was added ammonia water (1100 mL, w/w: 28-30%), and the solution described above was added dropwise with stirring over half an hour. After the dropwise addition was completed, the mixture was reacted with stirring at room temperature for 1 h. By TLC (PE:EA=1:1) and HPLC monitoring, the reaction was completed. The reaction solution was extracted with ethyl acetate (1.0 L×3). The organic phases were combined, washed successively with a 1 M aqueous solution of hydrochloric acid (500 mL×1) and then saturated brine (500 mL×2), dried over anhydrous sodium sulfate, and filtered. The filtrate was concentrated under reduced pressure to give 95 g of an off-white solid in a yield of 86.4% and a purity (HPLC) of >85%. $^1$H NMR (400 MHz, CDCl$_3$) δ (ppm): 6.65 (s, 1H), 6.08 (br s, 1H), 5.60 (br s, 1H), 4.41 (s, 2H), 2.86 (s, 3H), 1.41 (s, 9H).

Method 2:

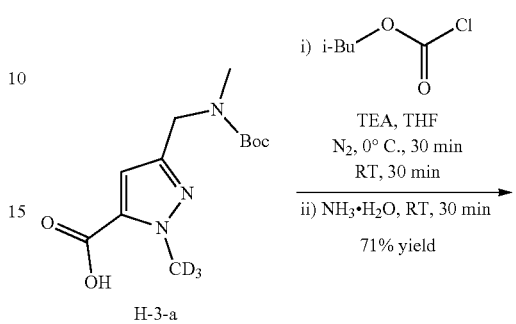

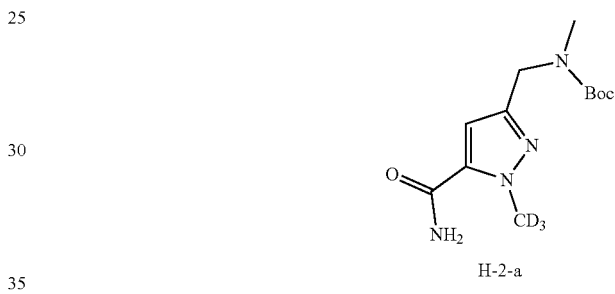

To a 250 mL three-necked flask equipped with magnetic stirring were added the compound of formula (H-3-a) (10 g, 36.8 mmol) and anhydrous THF (100 mL), and stirred until the solution became clear. Triethylamine (5.6 g, 55.1 mmol) was added, and the mixture was cooled to 0° C. in an ice-water bath. Isobutyl chloroformate (6.0 g, 44.2 mmol) was slowly added dropwise under nitrogen atmosphere over 20 min. After the dropwise addition was completed, the mixture was reacted with stirring at 0° C. for 30 min. The reaction solution was allowed to warm to room temperature, and stirred for 30 min. Ammonia water (100 mL, 28%-30%) was added, and the mixture was reacted with stirring for 30 min. TLC (DCM:MeOH=20:1) and HPLC showed that the reaction was completed. Petroleum ether (50 mL) was added to extract impurities with small polarity. The lower layer was separated, and extracted with ethyl acetate (100 mL×3). The ethyl acetate layers were combined, and adjusted to a pH of about 6 with a 2 M aqueous solution of hydrochloric acid. The organic phase was separated, and the aqueous phase was extracted with ethyl acetate (100 mL). The ethyl acetate phases were combined, washed with saturated brine (50 mL×2), dried over anhydrous sodium sulfate, and filtered. The filtrate was concentrated to dryness to give 7.1 g of an off-white solid in a yield of 71% and a purity (HPLC) of >85%.

Direct Aminolysis of the Compound of Formula (H-4-a) to Form the Compound of Formula (H-2-a)

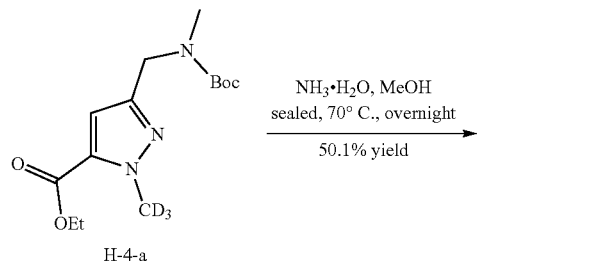

To a 300 mL sealed tube equipped with magnetic stirring were added the compound of formula (H-4-a) (20 g, 66.7 mmol) and methanol (40 mL), and stirred until the solution became clear. Ammonia water (28%-30%) (160 mL) was added, and the tube was sealed. The mixture was heated to 70° C. and reacted with stirring at this temperature overnight. The reaction solution was then allowed to cool to room temperature, and then cooled in an ice-water bath. The cap of the sealed tube was carefully unscrewed. TLC (PE:EA=1:1) showed that part of the raw materials remained unreacted, and part of the raw materials was hydrolyzed into acid. Petroleum ether (50 mL×2) was added to extract the unreacted raw materials, and the lower layer was extracted with ethyl acetate (100 mL×3). The ethyl acetate layers were combined, washed with saturated brine (40 mL×2), dried over anhydrous sodium sulfate, and filtered. The filtrate was concentrated to give 9 g of a white solid in a yield of 50.1% and a purity (HPLC) of >90%.

Dehydration of the Compound of Formula (H-2-a) to Form the Compound of Formula (H-1-a):

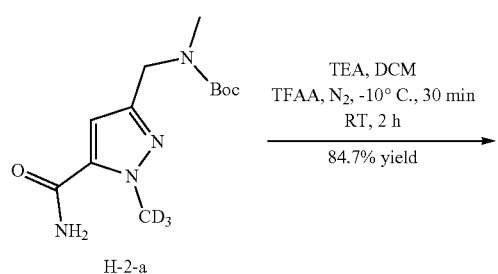

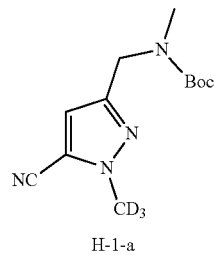

To a 3.0 L three-necked flask equipped with magnetic stirring were added the compound of formula (H-2-a) (95 g, 0.35 mol) and anhydrous DCM (1400 mL), and stirred until the solution became clear. Triethylamine (177 g, 1.75 mol) was added, and the mixture was cooled to −10° C. under nitrogen atmosphere. Trifluoroacetic anhydride (220 g, 1.05 mol) was slowly added dropwise over 30 min, and the mixture was reacted with stirring at room temperature for 2 hours. By TLC (PE:EA=1:1) and HPLC monitoring, the reaction was completed. The reaction was quenched by adding water (600 g), and the mixture was stirred for 30 min. The organic phase was separated, washed to neutral with a 1 M aqueous solution of hydrochloric acid, washed successively with an aqueous solution of $NaHCO_3$ (100 mL) and then saturated brine (200 mL), dried over anhydrous sodium sulfate, and filtered. The filtrate was concentrated under reduced pressure to give 75 g of a pale yellow oil in a yield of 84.7% and a purity (HPLC) of >85%. $^1$H NMR (300 MHz) δ (ppm): 6.66 (s, 1H), 4.37 (s, 2H), 2.83 (s, 3H), 1.43 (s, 9H).

Removal of the Protecting Group of the Compound of Formula (H-1-a) to Form the Compound of Formula (H):

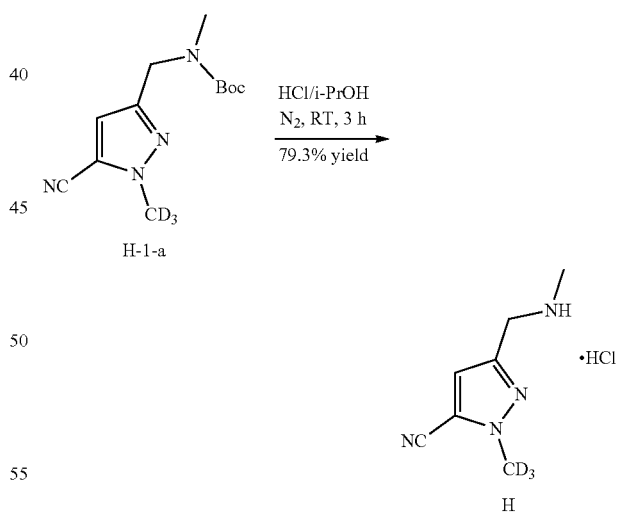

To a 3.0 L single-necked flask equipped with magnetic stirring were added the compound of formula (H-1-a) (75 g, 0.30 mol) and a 5 M isopropanol solution of hydrochloric acid (600 mL, 3.0 mol), and the mixture was reacted with stirring at room temperature under nitrogen atmosphere for 3 h. The reaction solution was diluted with ethyl acetate (1.8 L), and stirred for 30 minutes. The mixture was filtered, and washed with ethyl acetate (200 mL). The filter cake was dried with suction, and the filtrate was evaporated under reduced pressure to remove the residual solvent to give 45 g of a white powder in a yield of 79.3% and a purity (HPLC) of >97%.

Example 5: Alternative Synthesis of 1-(methyl-d$_3$)-3-((methylamino)methyl-5-cyano-1H-pyrazole (Compound of Formula (H))

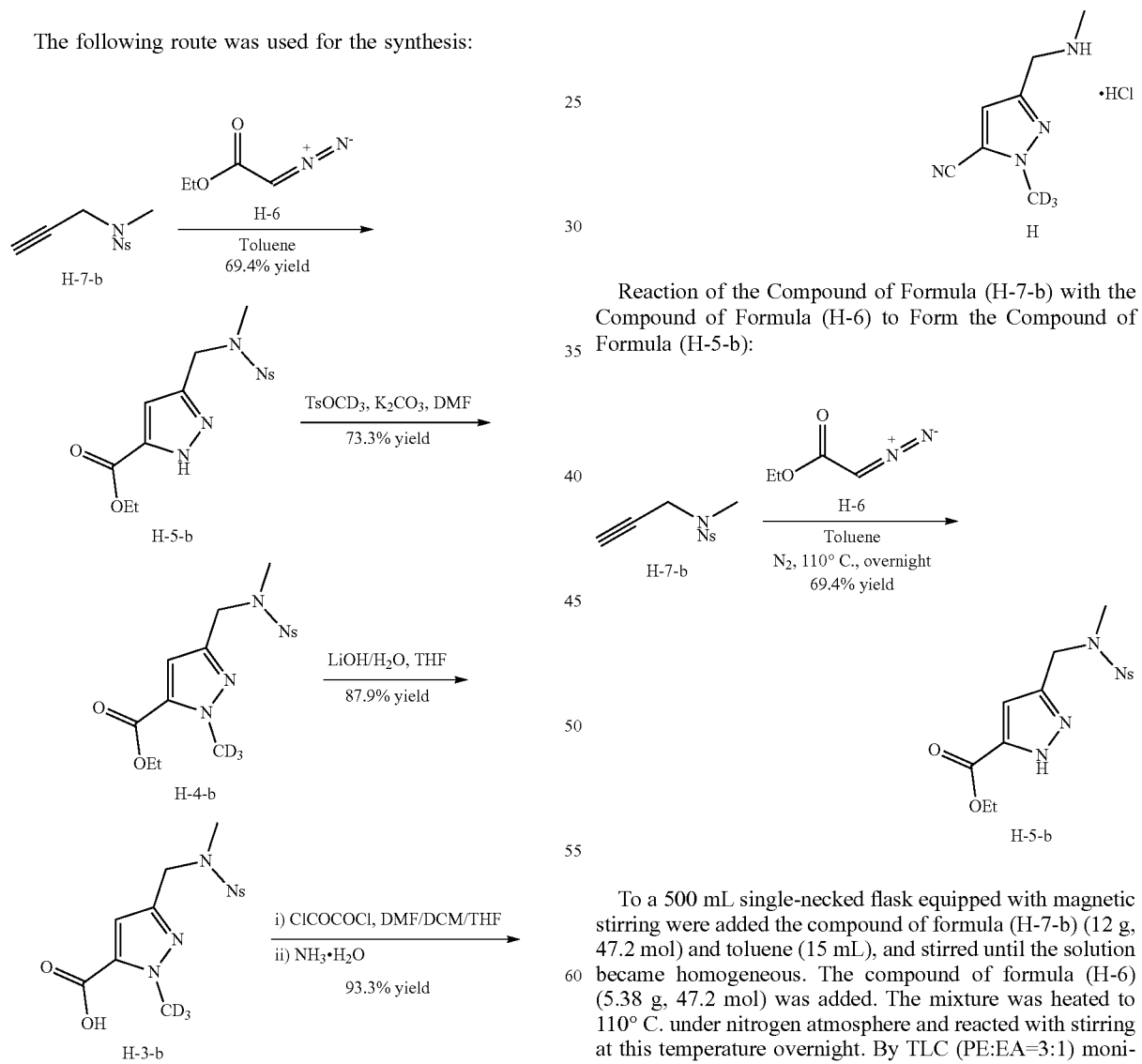

The following route was used for the synthesis:

Reaction of the Compound of Formula (H-7-b) with the Compound of Formula (H-6) to Form the Compound of Formula (H-5-b):

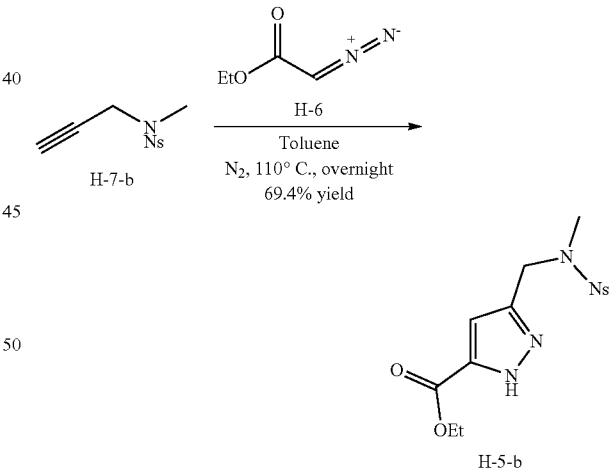

To a 500 mL single-necked flask equipped with magnetic stirring were added the compound of formula (H-7-b) (12 g, 47.2 mol) and toluene (15 mL), and stirred until the solution became homogeneous. The compound of formula (H-6) (5.38 g, 47.2 mol) was added. The mixture was heated to 110° C. under nitrogen atmosphere and reacted with stirring at this temperature overnight. By TLC (PE:EA=3:1) monitoring, the reaction was completed. The reaction solution was cooled to room temperature, and evaporated under reduced pressure to remove the solvent. The residue was purified by silica gel column chromatography to give 12 g of a white solid in a yield of 69.4% and a purity (HPLC) of >95%. $^1$H NMR (300 MHz, CDCl$_3$) δ (ppm): 8.08-8.05 (m, 1H), 7.76-7.67 (m, 3H), 6.88 (s, 1H), 4.51 (s, 2H), 4.39 (q, J=7.2 Hz, 2H), 2.87 (s, 3H), 1.40 (t, J=7.2 Hz, 3H).

Deuterated-Methylation of the Compound of Formula (H-5-b) to Form the Compound of Formula (H-4-b).

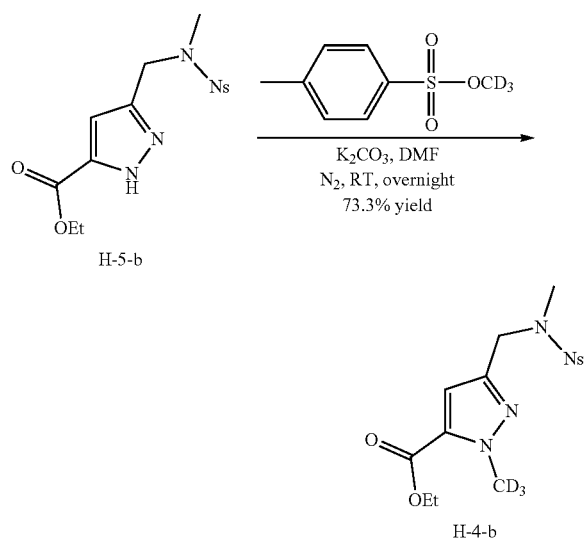

To a 250 mL single-necked flask equipped with magnetic stirring were added the compound of formula (H-5-b) (12 g, 32.6 mmol) and DMF (120 mL), and stirred until the solution became clear. Potassium carbonate (6.75 g, 48.9 mmol) and then TsOCD$_3$ (8.05 g, 42.4 mmol) were added successively, and the mixture was reacted with stirring at room temperature under nitrogen atmosphere overnight. TLC (PE:EA=3:1) showed that the reaction was completed. The reaction mixture was poured into water (300 mL), and extracted with ethyl acetate (150 mL×3). The organic phases were combined, washed successively with water (200 mL×3) and then saturated brine (100 mL), dried over anhydrous sodium sulfate, and filtered. The filtrate was concentrated under reduced pressure to give a brown oil, which was purified by silica gel column chromatography to give 9.2 g of a yellow oil in a yield of 73.3% and a purity (HPLC) of >95%. $^1$H NMR (300 MHz, CDCl$_3$) δ (ppm): 8.03-8.00 (m, 1H), 7.72-7.64 (m, 3H), 6.91 (s, 1H), 4.44 (s, 2H), 4.30 (q, J=7.2 Hz, 2H), 2.86 (s, 3H), 1.35 (t, J=7.2 Hz, 3H).

HYDROLYZATION of the compound of formula (H-4-b) to form the compound of formula (H-3-b):

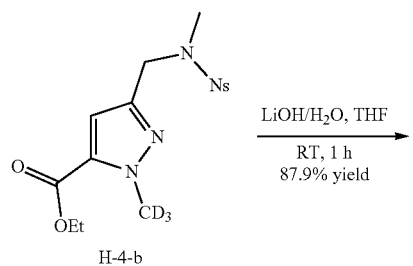

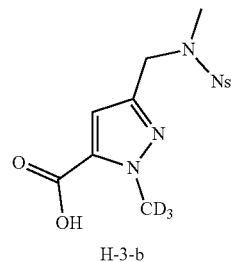

To a 250 mL single-necked flask equipped with magnetic stirring were added the compound of formula (H-4-b) (9.2 g, 23.9 mmol) and THF (45 mL), and stirred until the solution became homogeneous. A solution of LiOH—H$_2$O (2.0 g, 47.8 mol) in water (45 mL) was added, and the mixture was reacted with stirring at room temperature for 1 hour. By TLC (PE:EA=3:1) and HPLC monitoring, the reaction was completed. The reaction solution was evaporated under reduced pressure to remove the organic solvent. Additional ice water (50 mL) was added, and then solid NaHSO$_4$ was slowly added under an ice water bath to adjust pH to about 3. A large amount of a white solid precipitated out. The precipitated solid was filtered, washed with water (20 mL), and dried in vacuum at 40° C. to give 7.5 g of a white solid in a yield of 87.9% and a purity (HPLC) of >95%. $^1$H NMR (500 MHz, CDCl$_3$) δ (ppm): 8.07-8.05 (m, 1H), 7.74-7.66 (m, 3H), 6.95 (s, 1H), 4.45 (s, 2H), 2.88 (s, 3H).

Formation of an Amide Bond by a Method of Mixed Acid Anhydride to Form the Compound of Formula (H-2-b):

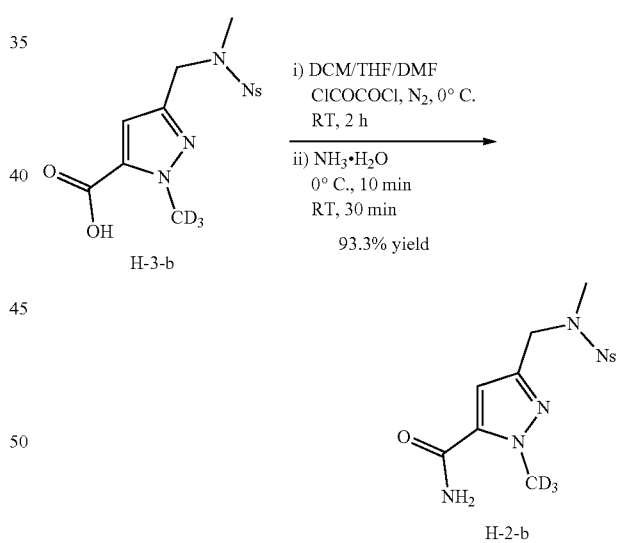

To a 250 mL three-necked flask equipped with magnetic stirring were added successively the compound of formula (H-3-b) (7.5 g, 21 mmol), anhydrous DCM (35 mL) and anhydrous THF (35 mL), and stirred until the solution became clear. Anhydrous DMF (153 mg, 2.1 mmol) was added, and the mixture was cooled to 0° C. in an ice-water bath. Oxalyl chloride (3.2 g, 25.2 mmol) was slowly added dropwise under nitrogen atmosphere. After the addition was completed, the ice bath was removed, and the mixture was reacted with stirring at room temperature for 2 hours. TLC (DCM:MeOH=20:1) showed that the reaction was completed. The reaction solution was evaporated under reduced pressure to remove the solvent and an excess amount of oxalyl chloride, and the residue was dissolved in anhydrous THF (20 mL) for further use.

To another 250 mL single-necked flask equipped with magnetic stirring was added ammonia water (28%-30%, 75 mL), and the above solution of acyl chloride in tetrahydrofuran was slowly added dropwise under an ice water bath over 10 min. After the dropwise addition was completed, the ice bath was removed, and the mixture was stirred at room temperature for 30 mm. TLC (DCM:MeOH=20:1) showed that the reaction was completed. Ethyl acetate (100 mL) was added, and the mixture was stirred for 5 minutes. The organic layer was separated, and the aqueous phase was extracted with ethyl acetate (50 mL×2). The organic phases were combined, washed with saturated brine (50 mL), dried over anhydrous sodium sulfate, and filtered. The filtrate was concentrated to dryness under reduced pressure to give 7.0 g of an off-white solid in a yield of 93.3% and a purity (HPLC) of >95%. $^1$H NMR (500 MHz, CDCl$_3$) δ (ppm): 8.04-8.02 (m, 1H), 7.75-7.66 (m, 3H), 6.67 (s, 1H), 6.16 (br s, 1H), 5.22 (br s, 1H), 4.41 (s, 2H), 2.86 (s, 3H).

Dehydration of the Compound of Formula (H-2-b) to Form the Compound of Formula (H-1-b):

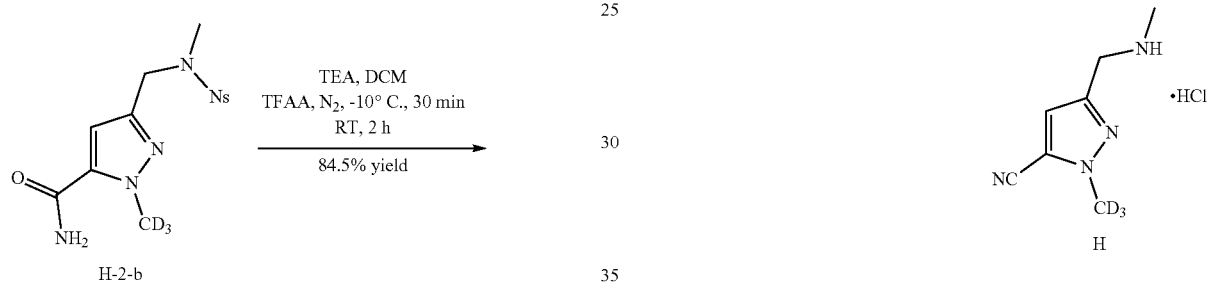

To a 250 mL three-necked flask equipped with magnetic stirring were added the compound of formula (H-2-b) (7.0 g, 19.6 mmol) and anhydrous DCM (70 mL), and stirred until the solution became clear. Triethylamine (10 g, 100 mol) was added, and the mixture was cooled to −10° C. under nitrogen atmosphere. Trifluoroacetic anhydride (12.4 g, 60 mol) was slowly added dropwise over 30 min. The mixture was reacted with stirring at room temperature for 2 hours. By TLC (PE:EA=1:1) and HPLC monitoring, the reaction was completed. The reaction was quenched by adding water (600 g). The mixture was diluted with DCM (100 mL), and stirred for 30 min. The organic phase was separated, washed to neutral with a 1 M aqueous solution of hydrochloric acid, washed successively with an aqueous solution of NaHCO$_3$ (30 mL) and then saturated brine (200 mL), dried over anhydrous sodium sulfate, and filtered. The filtrate was concentrated under reduced pressure to give 5.6 g of a pale yellow oil in a yield of 84.5% and a purity (HPLC) of >93%. $^1$H NMR (300 MHz, CDCl$_3$) δ (ppm): 8.07-8.04 (m, 1H), 7.75-7.69 (m, 3H), 6.81 (s, 1H), 4.44 (s, 2H), 2.85 (s, 3H).

Removal of the Protecting Group of the Compound of Formula (H-1-b) to Form the Compound of Formula (H):

To a 250 mL three-necked flask equipped with magnetic stirring were added the compound of formula (H-1-b) (5.6 g, 16.6 mmol) and anhydrous methanol (100 mL). The mixture was protected with nitrogen gas and placed in ice bath Mercaptoacetic acid (3.8 g, 41.4 mmol) was slowly added dropwise, and then potassium carbonate (11.4 g, 82.8 mmol) was added in portion to the reaction solution. The mixture was stirred in ice bath for 4 hours, and then warmed to room temperature and stirred for 2 hours. By TLC (PE:EA=1:1) and HPLC monitoring, the reaction was completed. The reaction was quenched by adding saturated brine (100 mL). The mixture was stirred for 5 min, and then extracted with dichloromethane (200 mL×3). The organic phases were combined, dried over anhydrous sodium sulfate, and filtered. The filtrate was concentrated under reduced pressure to give 2.6 g of a light yellow oil. The oil was dissolved in 5 mL of isopropanol, and then a 5 M isopropanol solution of hydrochloric acid (5 mL, 25 mmol) was added. The mixture was stirred at room temperature under nitrogen atmosphere for 3 h. The reaction solution was diluted by adding ethyl acetate (20 mL), stirred for 30 minutes, and then filtered. The filter cake was washed with ethyl acetate (10 mL), and dried with suction. The filtrate was evaporated under reduced pressure to remove the residual solvent to give 2.5 g of a white powder in a yield of 79.7% and a purity (HPLC) of >97%.

Example 6: Synthesis of (10R)-7-amino-12-fluoro-2-(methyl-d₃)-10,16-dimethyl-15-oxo-10,15,16,17-tetrahydro-2H-8,4-(metheno)pyrazolo[4,3-h][2,5,11]benzoxadiazacyclotetradecine-3-carbonitrile (the Compound of Formula (A))
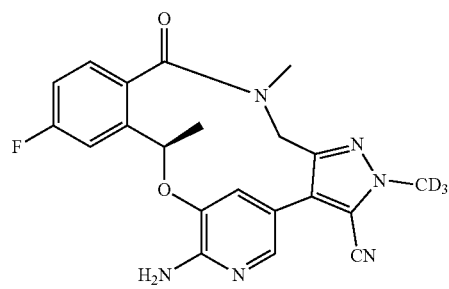
The following route was used for the synthesis:
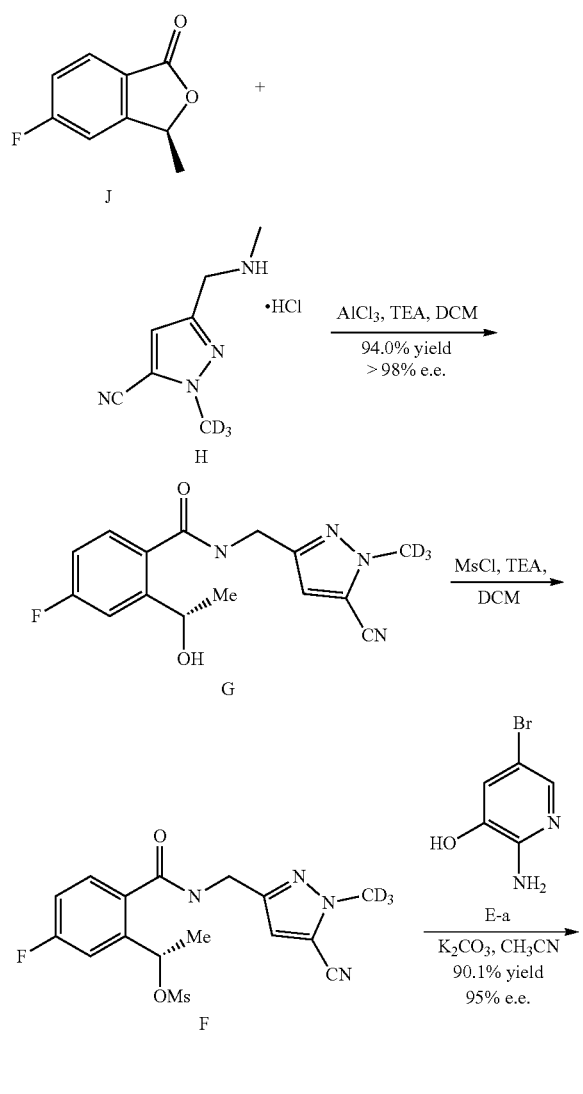
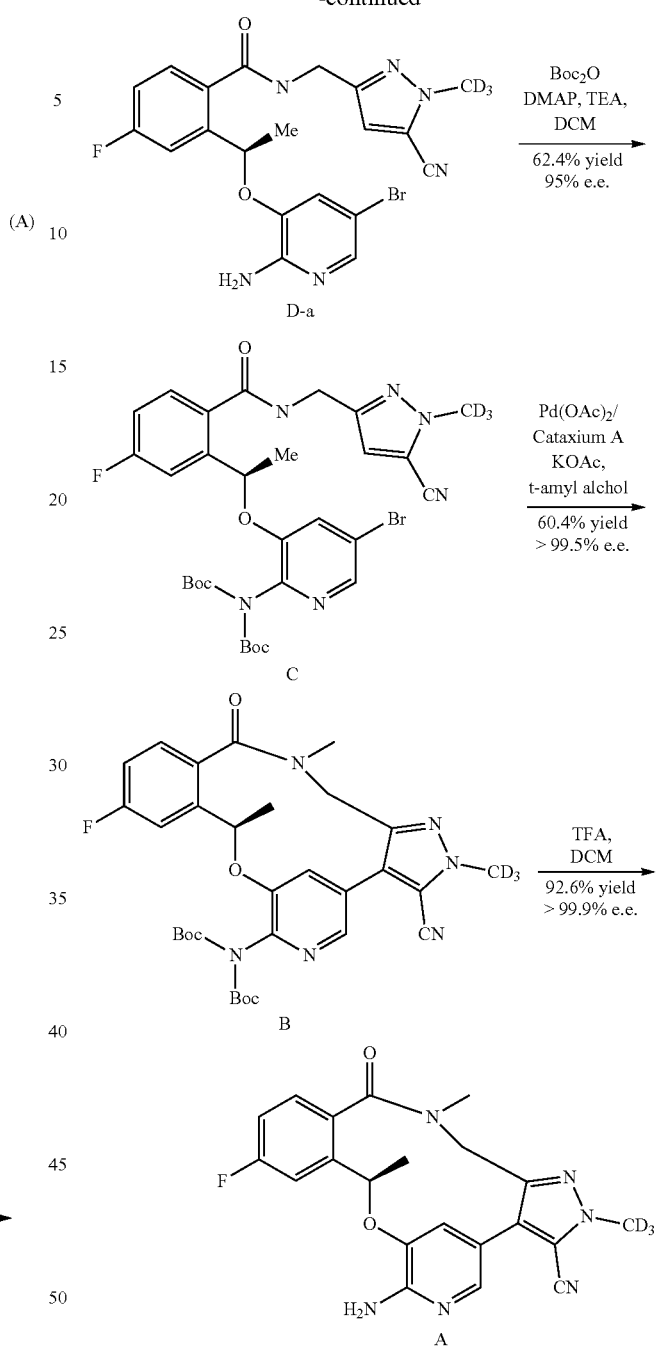
Ring-Opening of the Lactone of the Compound of Formula (J) with the Compound of Formula (H) to Form the Compound of Formula (G).

-continued

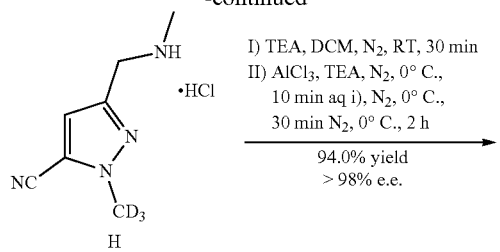

Sulfonylation of the Compound of Formula (G) to Form the Compound of Formula (F):

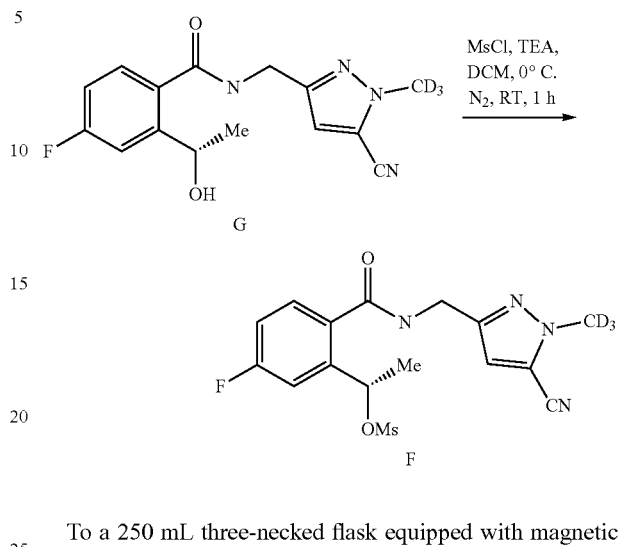

To a 250 mL three-necked flask equipped with magnetic stirring were added the compound of formula (J) (7.0 g, 42.2 mmol) and anhydrous dichloromethane (120 mL), and stirred until the solution became clear. The compound of formula (H) (8.77 g, 46.4 mmol) and then triethylamine (4.69 g, 46.4 mmol) were successively added. The mixture was stirred at room temperature under nitrogen atmosphere for 30 minutes to give a pale yellow clear solution for further use.

To another 500 mL three-necked flask equipped with magnetic stirring was added anhydrous aluminum chloride (6.17 g, 46.4 mmol), and the system was evacuated with suction and purged with nitrogen gas. Anhydrous dichloromethane (60 mL) was added under nitrogen atmosphere, and the mixture was cooled to 0° C. in an ice-water bath. Triethylamine (6.39 g, 63.3 mmol) was slowly added dropwise. After the addition was completed, the mixture was stirred at this temperature for 10 minutes. The above-mentioned solution of raw materials in dichloromethane was slowly added dropwise over 30 minutes. The mixture was reacted with stirring at this temperature for another 2 hours. By TLC (PE:EA=1:1) and HPLC monitoring, the reaction was completed. The reaction was quenched by adding water (200 mL). The organic phase was separated, and the aqueous layer was extracted with dichloromethane (100 mL×2). The organic phases were combined, washed successively with water (100 mL) and then saturated brine (100 mL), dried over anhydrous sodium sulfate, and filtered. The filtrate was concentrated to dryness under reduced pressure to give 12.66 g of a yellow oil in a yield of 94.0% and a purity (HPLC) of >90% (ee>98%). The intermediate is unstable at room temperature, and thus should be directly taken into the next step or stored in a refrigerator at −20° C. LC-MS (APCI): m/z=320.1 (M+1)$^+$. $^1$H NMR (300 MHz, CDCl$_3$) δ (ppm): 7.92-7.89 (m, 1H), 7.27-7.17 (m, 2H), 7.03-6.97 (m, 1H), 6.84 (s, 1H), 4.92 (q, J=6.3 Hz, 1H), 4.83 (s, 2H), 2.89 (s, 3H), 1.50 (d, J=6.3 Hz, 3H).

To a 250 mL three-necked flask equipped with magnetic stirring were added the compound of formula (G) (12.6 g, 39.5 mmol) and anhydrous dichloromethane (120 mL), and stirred until the solution became clear. The mixture was cooled in an ice-water bath. Triethylamine (7.98 g, 79.5 mmol) was added, and then methylsulfonyl chloride (5.85 g, 51.4 mmol) was slowly added dropwise. After the addition was completed, the ice bath was removed, and the mixture was reacted with stirring at room temperature under nitrogen atmosphere for 1 hour. TLC (DCM:MeOH=20:1) showed that the reaction was completed. The reaction was quenched by adding ice-water (100 mL). The organic phase was separated, and the aqueous layer was extracted with dichloromethane (50 mL×2). The organic phases were combined, washed successively with water (50 mL) and then saturated brine (50 mL), dried over anhydrous sodium sulfate, and filtered. The filtrate was concentrated to dryness under reduced pressure, and then dissolved in anhydrous acetonitrile (50 mL) for further use.

Alkylation of the Compound of Formula (E-a) with the Compound of Formula (F) to Form the Compound of Formula (D-a):

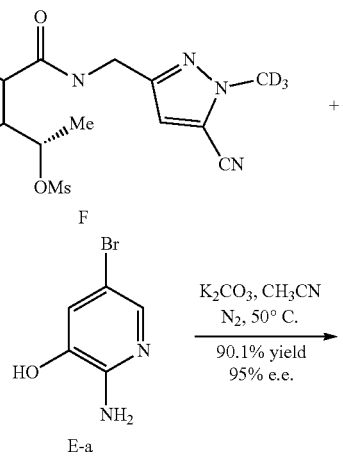

-continued

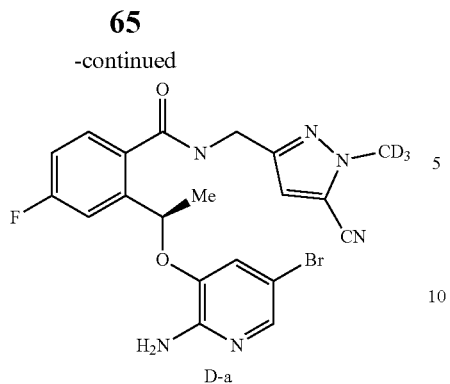

D-a

To another 250 mL three-necked flask equipped with magnetic stirring were added the compound of formula (E-a) (11.2 g, 59.3 mmol) and acetonitrile (200 mL), and cesium carbonate (25.7 g, 79.0 mmol) was added with stirring. The mixture was heated to 50° C. under nitrogen atmosphere, and stirred at this temperature for 30 min. The above-mentioned solution of the compound of formula (F) in acetonitrile was slowly added dropwise at 50° C. over 10 minutes. After the dropwise addition was completed, the mixture was reacted with stirring at this temperature for 2 hours. By TLC (DCM:MeOH=20:1) and HPLC monitoring, the reaction was completed. After cooling to room temperature, the reaction was quenched by adding water (200 mL). The reaction solution was diluted with ethyl acetate (300 mL), stirred for 5 minutes, and then filtered through Celite to remove insoluble solids. The filter cake was washed with ethyl acetate (50 mL). The organic layer was separated from the filtrate, and the aqueous phase was extracted with ethyl acetate (60 mL×2). The organic phases were combined, washed with a saturated aqueous solution of sodium carbonate (100 mL×3) and then saturated brine (60 mL), dried over anhydrous sodium sulfate, and filtered. The filtrate was concentrated to dryness under reduced pressure to give 17.5 g of a brown solid in a yield of 90.1% and a purity (HPLC) of >85% (ee>95%). LC-MS (APCI): m/z=390.1 (M+1)⁺.

Introduction of Boc Protecting Group into the Compound of Formula (D-a) to Form the Compound of Formula (C):

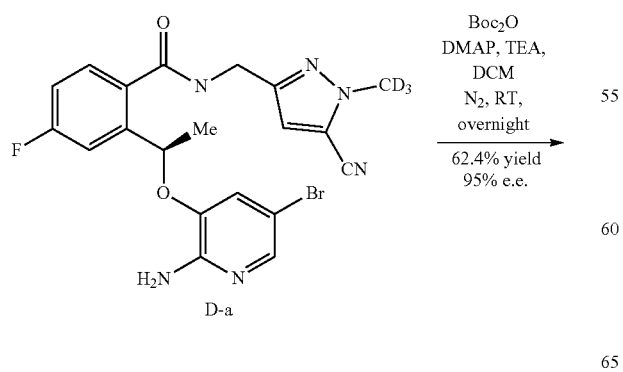

-continued

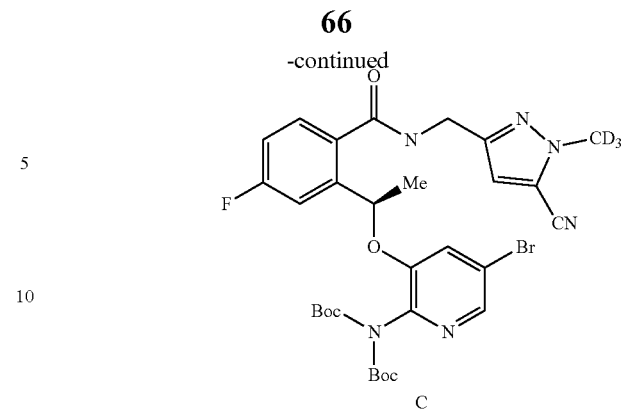

C

To a 250 mL single-necked flask equipped with magnetic stirring were added the compound of formula (D-a) (17.5 g, 35.8 mmol) and dichloromethane (200 mL), and stirred until the solution became clear. Triethylamine (14.5 g, 143.2 mmol) and then DMAP (850 mg, 7.2 mmol) were successively added. Boc₂O (23.4 g, 107.4 mmol) was slowly added dropwise, and the mixture was reacted with stirring at room temperature under nitrogen atmosphere overnight. By TLC (DCM:MeOH=20:1) and HPLC monitoring, the reaction was completed. The reaction solution was evaporated under reduced pressure to remove the solvent, and the residue was purified by silica gel column chromatography (EA/PE=0-35%) to give 15.4 g of a white solid in a yield of 62.4% and a purity (HPLC) of >95% (ee>95%). LC-MS (APCI): m/z=590.1 (M+1-100)⁺. ¹H NMR (300 MHz, CDCl₃) (δ/ppm): 8.06 (d, J=1.8 Hz, 1H), 7.53-7.48 (m, 1H), 7.24-7.20 (m, 2H), 7.04-6.98 (m, 1H), 6.81 (s, 1H), 5.66-5.59 (m, 1H), 4.89-4.69 (m, 2H), 2.97 (s, 3H), 1.58 (d, J=6.0 Hz, 3H), 1.47 (s, 18H).

Cyclization of the Compound of Formula (C) Using Palladium Catalyst to Form the Compound of Formula (B):

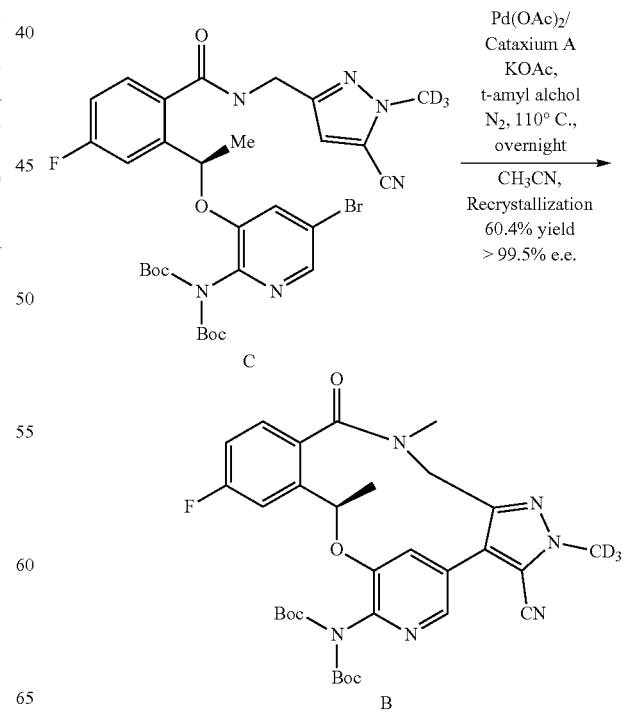

To a 500 mL single-necked flask equipped with magnetic stirring were added the compound of formula (C) (15.4 g, 22.3 mmol) and 2-methyl-2-butanol (300 mL), and stirred until the solution became clear. Potassium acetate (6.56 g, 66.9 mmol) was added. The system was evacuated with suction and purged with nitrogen gas three times. Palladium acetate (0.75 g, 3.35 mmol) and n-butylbis(1-adamantyl) phosphine (1.60 g, 4.46 mmol) were quickly added. The system was evacuated with suction and purged with nitrogen gas three times. The reaction solution was heated to 110° C. under nitrogen atmosphere, and reacted with stirring at this temperature overnight. By TLC (PE:EA=1:1) and HPLC monitoring, the reaction was completed. The reaction solution was cooled to room temperature, diluted with dichloromethane (300 mL), and filtered through Celite to remove insoluble solids. The filter cake was washed with dichloromethane (50 mL). The filtrates were combined, and concentrated to dryness under reduced pressure. To the residue was added acetonitrile (150 mL), and the mixture was heated to reflux for 1 hour. The oil bath was removed, and the mixture was allowed to slowly cool to room temperature. A large amount of a white solid precipitated out, and the precipitated solid was filtered. The filter cake was washed with acetonitrile (10 mL), and dried to give 8.2 g of a white solids in a yield of 60.4% and a purity (HPLC) of >99.5% (ee>99.9%). LC-MS (APCI): m/z=510.1 (M+1−100)⁺. ¹H NMR (300 MHz, CDCl₃) (δ/ppm): 8.22 (d, J=1.8 Hz, 1H), 7.29-7.25 (m, 1H), 7.22-7.16 (m, 2H), 7.03-6.96 (m, 1H), 5.76-5.70 (m, 1H), 4.42 (q, J=14.1 Hz, 2H), 3.15 (s, 3H), 1.76 (d, J=6.0 Hz, 3H), 1.44 (s, 18H).

Removal of the Boc from the Compound of Formula (B) Using an Acid to Form the Compound of Formula (A):

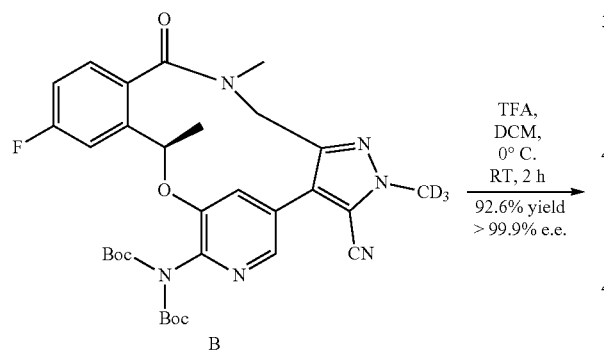

at room temperature for 2 hours. By TLC (DCM:MeOH=20:1) and HPLC monitoring, the reaction was completed. The reaction solution was evaporated under reduced pressure to remove the organic solvent. Dichloromethane (100 mL) and a saturated aqueous solution of sodium bicarbonate (60 mL) were added under cooling, and the mixture was stirred for 10 minutes. The organic phase was separated, and the aqueous layer was extracted with dichloromethane (50 mL×2). The organic phases were combined, washed successively with water (30 mL) and then saturated brine (500 mL), dried over anhydrous sodium sulfate, and filtered. The filtrate was concentrated under reduced pressure to give 5.1 g of an amorphous white solid in a yield of 92.6% and a purity (HPLC) of >99.5% (ee>99.9%). LC-MS (APCI): m/z=410.2 (M+1)⁺. ¹H NMR (300 MHz, CDCl₃) (δ) ppm 7.79 (d, J=1.8 Hz, 1H), 7.31-7.27 (m, 1H), 7.23-7.19 (m, 1H), 7.06-6.97 (m, 1H), 6.87 (d, J=1.8 Hz, 1H), 5.75-5.70 (m, 1H), 5.09 (br s, 2H), 4.40 (q, J=14.1 Hz, 2H), 3.12 (s, 3H), 1.78 (d, J=6.6 Hz, 3H).

Example 7: Alternative Reaction for Synthesis of the Compound of Formula (C)

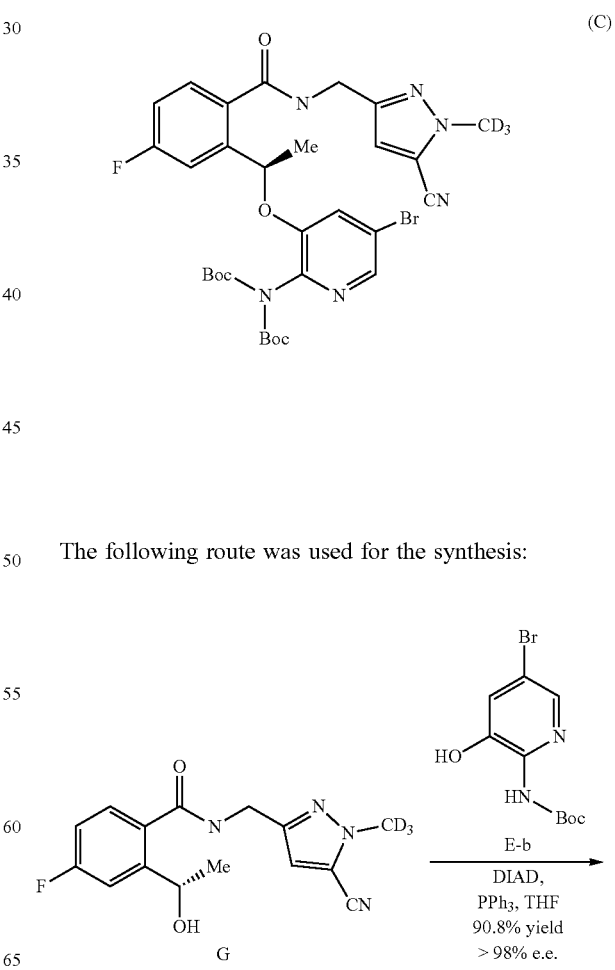

To a 250 mL single-necked flask equipped with magnetic stirring were added the compound of formula (B) (8.2 g, 13.5 mmol) and dichloromethane (100 mL), and stirred until the solution became clear. The mixture was cooled in an ice-water bath, and trifluoroacetic acid (20 mL) was slowly added dropwise. After the addition was completed, the ice bath was removed, and the mixture was reacted with stirring The following route was used for the synthesis:

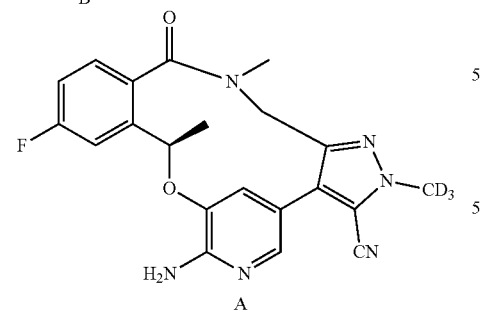

-continued

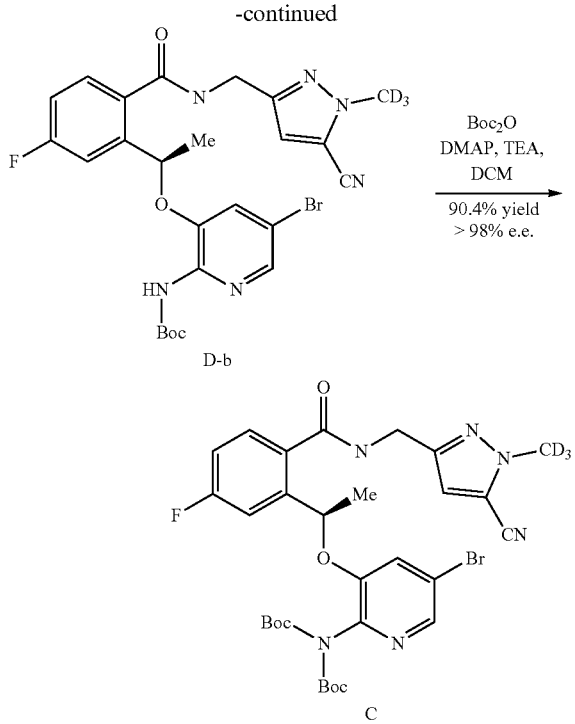

Reaction of the Compound of Formula (G) with the Compound of Formula (E-b) to Form the Compound of Formula D-b:

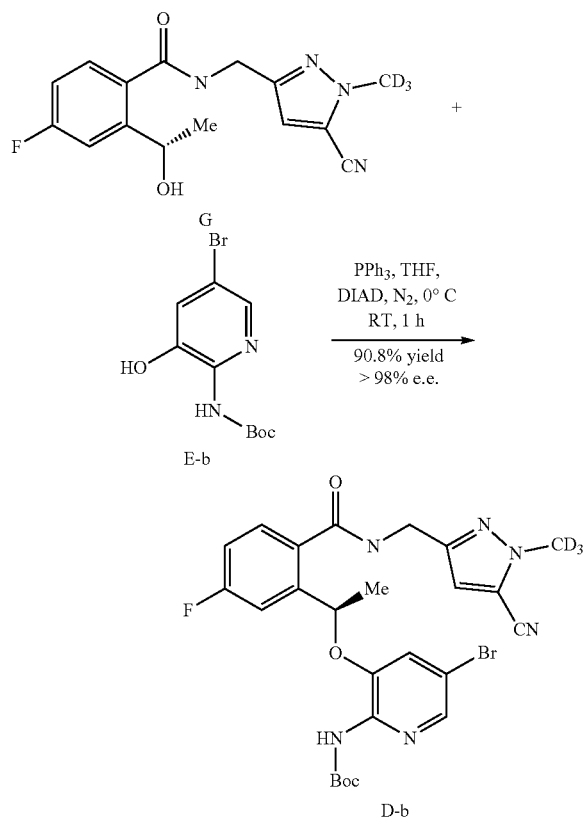

To a 500 mL three-necked flask equipped with magnetic stirring were added successively the compound of formula (E-b) (11.4 g, 39.43 mmol), the compound of formula (G) (12.6 g, 39.43 mmol) and anhydrous THF (200 mL), and stirred until the solution became clear. Triphenylphosphine (12.4 g, 47.31 mmol) was added. The system was evacuated with suction and purged with nitrogen gas three times. The mixture was cooled to 0° C. in an ice-water bath, and then diisopropyl azodicarbonate (9.6 g, 47.31 mmol) was slowly added dropwise. After the addition was completed, the mixture was reacted with stirring at room temperature for 1 hour. By TLC (PE:EA=1:1) and HPLC monitoring, the reaction was completed. The reaction solution was evaporated under reduced pressure to remove the solvent, and the residue was purified by silica gel column chromatography (PE:EA=2:1) to give 21.1 g of a white solid in a yield of 90.8%. $^1$H NMR (300 MHz, DMSO-$D_6$) δ 9.18 (s, 1H), 7.95 (d, J=1.5 Hz, 1H), 7.67-7.58 (m, 2H), 7.43-7.39 (m, 1H), 7.22-7.17 (m, 1H), 7.14 (s, 1H), 5.57-5.52 (m, 1H), 4.77-4.68 (m, 2H), 2.80 (s, 3H), 1.52 (d, J=4.5 Hz, 3H), 1.47 (s, 9H), ee>98%.

Introduction of Boc into the Compound of Formula (D-b) to Form the Compound of Formula (C):

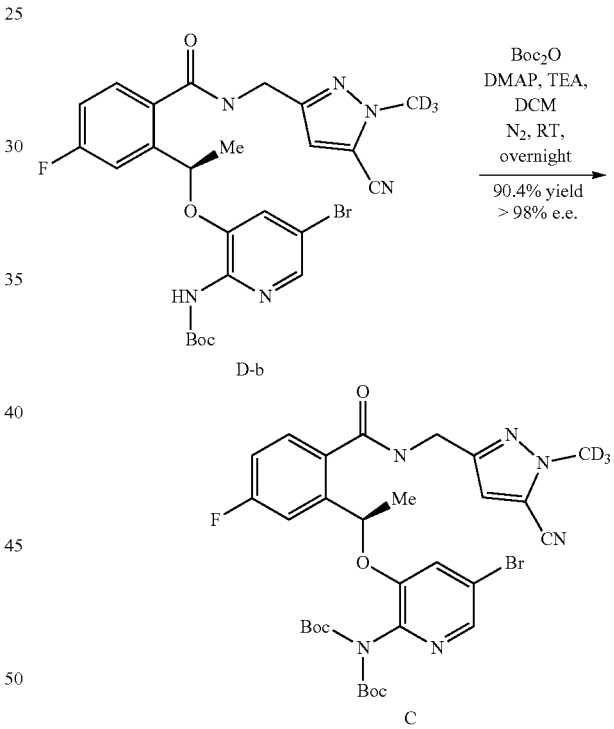

To a 250 mL single-necked flask equipped with magnetic stirring were added the compound of formula (D-b) (21.1 g, 35.8 mmol) and dichloromethane (200 mL), and stirred until the solution became clear. Triethylamine (10.8 g, 107.4 mmol) and then DMAP (802 mg, 7.16 mmol) were added successively. Boc$_2$O (11.7 g, 53.7 mmol) was slowly added dropwise, and the mixture was reacted with stirring at room temperature under nitrogen atmosphere overnight. By TLC (DCM:MeOH=20:1) and HPLC monitoring, the reaction was completed. The reaction solution was evaporated under reduced pressure to remove the solvent, and the residue was purified by silica gel column chromatography (EA:PE=0-35%) to give 22.3 g of an oil in a yield of 90.4% (ee>98%). $^1$H NMR (300 MHz, CDCl$_3$) δ 8.06 (d, J=1.8 Hz, 1H), 7.53-7.48 (m, 1H), 7.24-7.20 (m, 2H), 7.04-6.98 (m, 1H), 6.81 (s, 1H), 5.66-5.59 (m, 1H), 4.89-4.69 (m, 2H), 2.97 (s, 3H), 1.58 (d, J=6.0 Hz, 3H), 1.47 (s, 18H).

The following are examples of methods for large-scale production.

Example 8: Synthesis of (S)-5-fluoro-3-methyl-isobenzofuran-1(3H)-one (Compound of Formula (J)

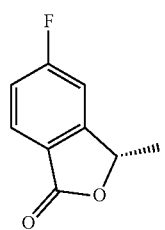

(J)

The following route was used for the synthesis.

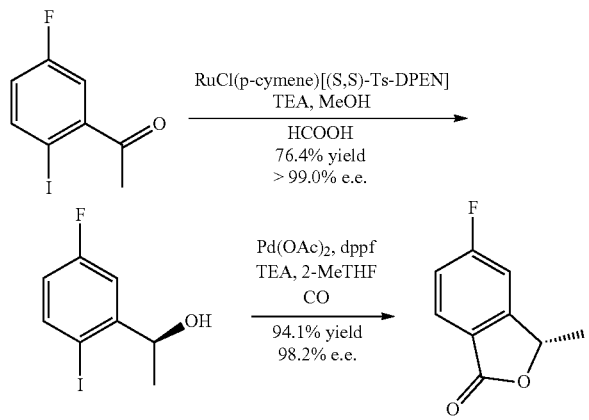

Step 1: (S)-1-(5-fluoro-2-iodophenyl)ethanol

Under the protection of nitrogen, while maintaining the temperature at 15 to 30° C., to a 200 L reaction kettle was added methanol (60 L). 3-fluoro-6-iodoacetophenone (14.0 kg, 53.0 mol) and then triethylamine (13.4 kg, 132.6 mol) were added successively with stirring, and stirred until the solution became clear. RuCl(p-cymene)[(s,s)-Ts-DPEN] (340 g, 0.53 mol) was added. The system was evacuated with suction and then purged with nitrogen gas five times. In nitrogen atmosphere, the mixture was cooled to 0° C., and then formic acid (12.0 kg, 238.6 mol) was slowly added dropwise. During the dropwise addition, the temperature was controlled not higher than 20° C. After the dropwise addition was completed, the mixture was reacted at room temperature for 2 days.

The reaction was monitored by HPLC until the reaction was completed. The reaction solution was concentrated to about 20 L under reduced pressure, and water (40 L) and methyl tert-butyl ether (30 L) were added. The mixture was stirred for 20 minutes, and then allowed to stand still. The organic phase was separated, and the aqueous phase was extracted with methyl tert-butyl ether (30 L×1). The organic phases were combined, washed with water (10 L×2) and then saturated brine (10 L), and concentrated under reduced pressure to 14 L. n-heptane (70 L) was added, and the mixture was concentrated under reduced pressure to about 50 L. The mixture was then heated to reflux and stirred until the solution became clear. The mixture was slowly cooled to 0° C., and stirred at this temperature for 4 hours. The mixture was filtered. The filter cake was washed with n-heptane (7 L), and dried in vacuum at 40° C. overnight to give 10.7 kg of an off-white solid in a yield of 76.4% (ee>99.0%). LC-MS: m/z=267.0 (M+1)$^+$, purity: 94.5%, and wavelength: 220 nm.

Step 2: Synthesis of (S)-5-fluoro-3-methylisobenzofuran-1(3H)-one

Under the protection of nitrogen, while maintaining the temperature at 15 to 30° C., to a 20 L autoclave kettle was added 2-methyltetrahydrofuran (13.5 L). (S)-1-(5-fluoro-2-iodophenyl)ethanol (3.4 kg, 12.8 mol), triethylamine (3.6 L, 25.2 mol), palladium acetate (5.67 g, 25.3 mmol), and then dppf (21.22 g, 38.0 mmol) were added successively with stirring. The system was evacuated with suction and purged with carbon monoxide five times. The pressure was raised to 5 atmospheres. The mixture was heated to 100° C. and reacted with stirring at this temperature overnight.

The reaction was monitored by HPLC until the reaction was completed. The reaction solution was cooled to room temperature. The pressure was released, and the system was purged with nitrogen gas. The reaction solution was filtered, and the filter cake was washed with ethyl acetate (5 L×3). The organic phases were combined, and washed with water (4 L×2). The organic phase was concentrated to about 7 L under reduced pressure, and n-heptane (16 L) was added. The mixture was concentrated to about 7 L under reduced pressure, heated to 65° C., and stirred at this temperature overnight. The reaction solution was cooled to 0° C., and stirred at this temperature for 4 hours. The mixture was filtered, and the filter cake was washed with n-heptane (3 L×2), and dried in vacuum at 40° C. overnight to give 2.0 kg of a brown solid in a yield of 94.1% (ee=98.2%). LC-MS: m/z=167.1 (M+1)$^+$, purity: 96.5%, and wavelength: 220 nm. $^1$H NMR (400 MHz, CDCl$_3$) δ (ppm): 7.92-7.89 (m, 1H), 7.26-7.21 (m, 1H), 7.12 (dd, J=7.6 Hz, J=2.0 Hz, 1H), 5.54 (q, J=7.6 Hz, 1H), 1.65 (d, J=7.6 Hz, 3H).

Example 9: Synthesis of p-toluenesulfonic acid (methyl-d$_3$) ester

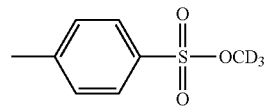

The following route was used for the synthesis.

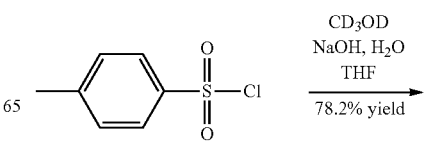

-continued

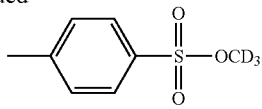

To a 50 L reaction kettle was added tetrahydrofuran (20 L), and cooled in a water bath. P-toluenesulfonyl chloride (10 kg, 50.26 mol) was added with stirring, and stirred until the solution became clear for further use.

To a 100 L reaction kettle was added purified water (20 L). and stirring was started. Solid NaOH (3.15 kg, 70.88 mol) was added under cooling, and completely dissolved. The mixture was cooled to below 10° C. CD$_3$OD (2.02 kg, 57.7 mol) was added under nitrogen atmosphere, and the mixture was further cooled to below 0° C. The above-mentioned solution of p-toluenesulfonyl chloride in tetrahydrofuran was slowly added dropwise over 2 hours not higher than 10° C. The mixture was reacted with stirring for 1 hour while maintaining a temperature of 20-30° C. By TLC (PE: EA=10:1) monitoring, the reaction was completed.

To the reaction solution was added ethyl acetate (20 L), and the mixture was stirred for 10 minutes. The organic phase was separated, and the aqueous phase was transferred back to the kettle. Ethyl acetate (10 L) was added, and the layers were separated. The organic phases were combined, washed with saturated brine (5 L×2), dried over anhydrous sodium sulfate, and filtered. The filtrate was concentrated to dryness under reduced pressure to give 7.78 kg of a white liquid in a yield of 78.16%. The white oil was allowed to stand at room temperature, and then solidified into a white solid.

Example 10: Synthesis of the Compound of Formula (H-5-a)

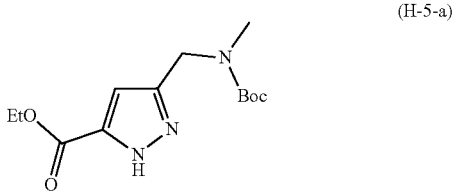 [SMILES: CCOC(=O)c1cc(CN(C)C(=O)OC(C)(C)C)n[nH]1]
(H-5-a)

The following route was used for the synthesis:

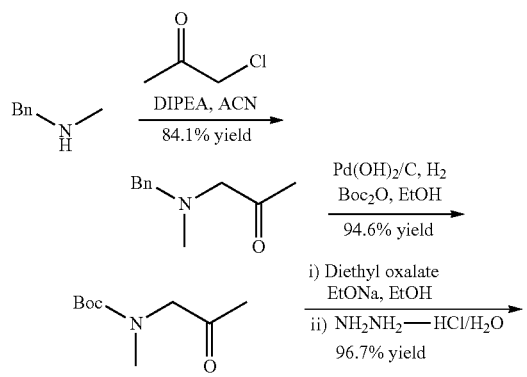

-continued

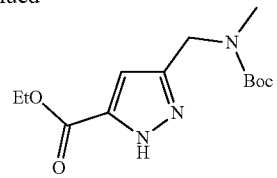
H-5-a

Step 1: Synthesis of 1-(benzyl(methyl)amino)propan-2-one

Under the protection of nitrogen, while maintaining the temperature at 20 to 30° C., to a 300 L reaction kettle was added acetonitrile (52 L) with suction. Benzylmethylamine (26 kg, 214.72 mol) and then DIPEA (28.28 kg, 218.80 mol) were added successively with stirring and cooling, and the mixture was cooled to below 10° C. Chloroacetone (21.23 kg, 230.75 mol) was slowly added dropwise over 9 hours while maintaining the temperature not higher than 20° C. After the dropwise addition was completed, the mixture was allowed to naturally warm to 20 to 30° C. and reacted with stirring overnight (16 hours).

The reaction was monitored by LC-MS until the reaction was completed. The reaction solution was concentrated to about 25 L under reduced pressure. Methyl tert-butyl ether (75 L) was added, and the mixture was slurried with stirring for 3 hours. The slurry was filtered through silica gel, and washed with methyl tert-butyl ether (25 L×2). The organic phases were combined, and concentrated to dryness under reduced pressure to give 32.00 kg of a brown oil in a yield of 84.1%.

Step 2: Synthesis of 1-(tert-butoxycarbonyl(methyl)amino)propan-2-one

Under the protection of nitrogen, while maintaining the temperature at 15 to 25° C. to a 200 L autoclave kettle was added ethanol (90 L). 1-(benzyl(methyl)amino)propan-2-one (30.0 kg, 169.26 mol). Boc$_2$O (38.79 kg, 177.72 mol) and then wet palladium hydroxide/carbon (20 wt %, 4 kg) were added successively with stirring. The system was purged with hydrogen gas three times. The pressure was raised to 30 Mpa. The reaction solution was reacted with stirring overnight (16 hours) while maintaining the temperature at 40° C.

The reaction was monitored by LC-MS until the reaction was completed. The pressure was released, and the hydrogen gas was replaced with nitrogen gas. The reaction solution was filtered with suction, and washed with ethanol (20 L×2). The organic phases were combined, and concentrated to dryness under reduced pressure to give 30.2 kg of a yellow oil in a yield of 94.6%. The recovered palladium hydroxide/carbon can be reused 3 times.

Step 3: Synthesis of the Compound of Formula (H-5-a)

Under the protection of nitrogen, while maintaining the temperature at 15 to 25° C. to a 500 L reaction kettle was added ethanol (90 L). Solid sodium ethoxide (10.92 kg, 160.2 mol) was added with stirring and cooling, and the mixture was cooled to 0° C. A mixed solution of 1-(tert-butoxycarbonyl(methyl)amino)propan-2-one (30.0 kg, 160.2 mol) and diethyl oxalate (28.1 kg, 192.2 mol) was slowly added dropwise over 2 hours. After the dropwise addition was completed, the reaction solution was allowed to warm naturally to room temperature and reacted with stirring overnight (16 hours).

By HPLC monitoring, the reaction was completed. The reaction solution was cooled to 0° C. A solution of hydrazine hydrochloride (10.9 kg, 160.2 mol) in water (15 L) was slowly added dropwise over 1 hour. The mixture was reacted with stirring at room temperature for 3 hours.

By HPLC monitoring, the reaction was completed. Dichloromethane (120 L) and water (150 L) were added. The organic phase was separated, washed with water (150 L) and then saturated brine (40 L), dried over anhydrous sodium sulfate, and filtered. The filtrate was concentrated to dryness under reduced pressure to give 45.3 kg of a black oil in a yield of 98.7%. LC-MS: m/z=184.1 $(M-100+1)^+$, purity: 91.8%, and wavelength: 220 nm.

Example 11: Synthesis of 1-(methyl-$d_3$)-3-((methyl-amino)methyl)-5-cyano-1H-pyrazole (Compound of Formula (H))

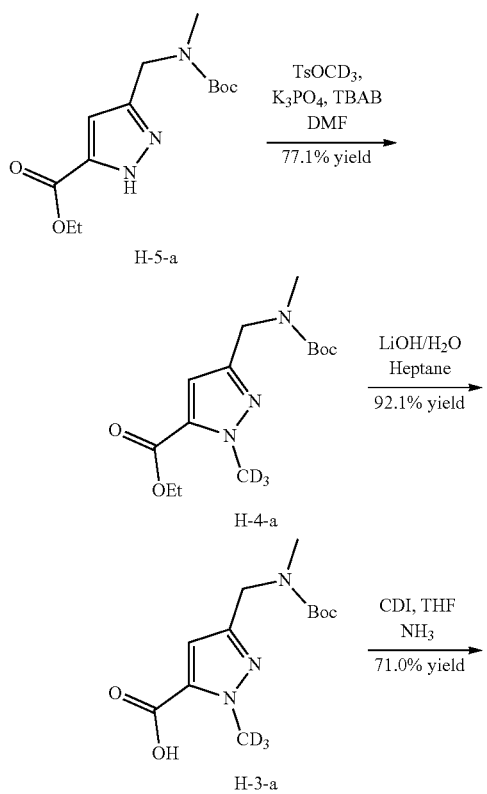

The following route was used for the synthesis:

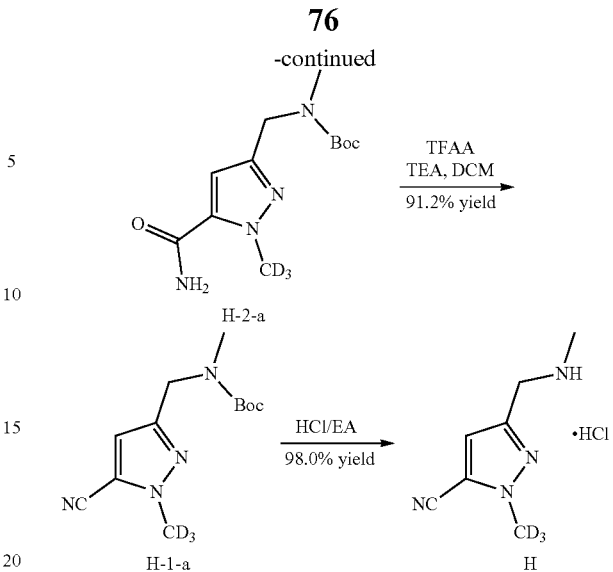

Step 1: Deuterated-Methylation of the Compound of Formula (H-5-a) to Form the Compound of Formula (H-4-a)

Under the protection of nitrogen, while maintaining the temperature at 15 to 30° C., to a 300 L reaction kettle was added water (54 L). Potassium phosphate (43.3 kg, 190.6 mol) was added with stirring and cooling, and the mixture was cooled to 0° C. A solution of the compound of formula (H-5-a) (45 kg, 158.8 mol) in DMF (54 L) was slowly added dropwise over 10 min. TBAB (2.74 kg, 7.94 mol) was then added, and a solution of $TsOCD_3$ (32.1 kg, 158.8 mol) in DMF (26 L) was slowly added dropwise over half an hour while maintaining the temperature at 10° C. After the dropwise addition was completed, the reaction solution was reacted with stirring at room temperature for 4 hours.

The reaction was monitored by HPLC until the reaction was completed. Water (135 L) and n-heptane (45 L) were added, and the mixture was stirred for 20 min. The upper n-heptane layer was separated, and the lower aqueous phase was extracted with n-heptane (45 L×2). The n-heptane phases were combined, washed with water (100 L×2) and then saturated brine (50 L), dried over anhydrous sodium sulfate, and filtered. The filtrate was concentrated to dryness under reduced pressure to give 36.7 kg of a black oil in a yield of 77.1%. LC-MS: m/z=201.1 $(M-100+1)^+$, purity: 78.89%, and wavelength: 220 nm. Another isomer was contained with a content of 21.1%.

Step 2: Hydrolyzation of the Compound of Formula (H-4-a) to Form the Compound of Formula (H-3-a)

Under the protection of nitrogen, while maintaining the temperature at 15 to 30° C., to a 300 L reaction kettle was added water (70 L). Lithium hydroxide monohydrate (7.65 kg, 182.2 mol) was added with stirring and cooling. A solution of the compound of formula (H-4-a) (36.5 kg, 121.5 mol) in n-heptane (70 L) was added while maintaining the temperature not higher than 20° C. After the addition was completed, the mixture was reacted with stirring at room temperature overnight.

The reaction was monitored by HPLC until the reaction was completed. The lower aqueous layer was separated, and a 3 M solution of hydrochloric acid was slowly added dropwise to adjust pH to about 3. The mixture was extracted with dichloromethane (37 L×3). The organic phases were combined, dried over anhydrous sodium sulfate, and filtered. The filtrate was concentrated to about 50 L under reduced pressure. n-heptane (150 L) was added, and the mixture was further concentrated to about 140 L under reduced pressure. A large amount of solids precipitated out. The mixture was filtered, and washed with n-heptane to give 30.4 kg of an off-white solid in a yield of 92.1%. LC-MS: m/z=217.2 (M−55+1)$^+$, purity: 75.7%, and wavelength: 220 nm. Another isomer was contained with a content of 13.5%.

Step 3: Formation of an Amide Bond by the Method of Mixed Acid Anhydride to Form the Compound of Formula (H-2-a)

Under the protection of nitrogen, while maintaining the temperature at 15 to 30° C., to a 300 L reaction kettle was added tetrahydrofuran (120 L). The compound of formula (H-3-a) (30 kg, 110.2 mol) and CDI (35.7 kg, 220.4 mol) were added with stirring and cooling, and the mixture was cooled to 0° C. To the system was introduced ammonia gas (15.0 kg, 881.6 mol), and then the system was sealed and reacted with stirring overnight.

The reaction was monitored by HPLC until the reaction was completed. A 3 M solution of hydrochloric acid was slowly added dropwise to adjust pH to about 8. The mixture was evaporated under reduced pressure to remove the solvent until the residue reached a volume of about 50 L. Dichloromethane (100 L) and 0.5 M hydrochloric acid (100 L) were added. The mixture was stirred for 20 min, and then allowed to stand still for layering. The dichloromethane layer was separated, washed again with 0.5 M hydrochloric acid (100 mL×2), dried over anhydrous sodium sulfate, and filtered. The filtrate was concentrated to about 40 L. Water (120 L) was added, and the mixture was distilled under reduced pressure at 45° C. until no droplets flowed out. The mixture was heated to reflux and stirred until the solution became clear. The mixture was allowed to naturally cool to room temperature with stirring, and then further stirred for 2 hours. A large amount of solids precipitated out. The mixture was filtered, and the filter cake was washed with water (10 L), and dried by baking to give 21.2 kg of a white solid in a yield of 71%. LC-MS: m/z=216.2 (M−55+1)$^+$, purity: 99.2%, and wavelength: 220 nm. $^1$H NMR (400 MHz, CDCl$_3$) δ (ppm): 6.65 (s, 1H), 6.08 (br s, 1H), 5.60 (br s, 1H), 4.41 (s, 2H), 2.86 (s, 3H), 1.41 (s, 9H).

Step 4: Dehydration of the Compound of Formula (H-2-a) to Form the Compound of Formula (H-1-a)

Under the protection of nitrogen, while maintaining the temperature at 15 to 30° C., to a 300 L reaction kettle was added anhydrous dichloromethane (120 L). The compound of formula (H-2-a) (21.0 kg, 77.5 mol) and triethylamine (31.4 kg, 31.0 mol) were added with stirring, and stirred until the solution became clear. The mixture was then cooled to −10° C. TFAA (32.6 kg, 155.0 mol) was slowly added dropwise over 3 hours while maintaining the temperature not higher than 0° C. The reaction solution was reacted with stirring at 0° C. overnight (16 hours).

The reaction was monitored by HPLC until the reaction was completed. The reaction was quenched by adding water (60 L), and the mixture was stirred for half an hour. The organic phase was separated, washed to neutral with 0.5 M hydrochloric acid, washed with saturated brine (20 L), dried over anhydrous sodium sulfate, and filtered. The filtrate was concentrated to dryness under reduced pressure to give 17.8 kg of a brown oil in a yield of 91.2%. LC-MS: m/z=154.2 (M−100+1)$^+$, purity: 97.9%, and wavelength: 220 nm. $^1$H NMR (300 MHz, CDCl$_3$) δ (ppm): 6.66 (s, 1H), 4.37 (s, 2H), 2.83 (s, 3H), 1.43 (s, 9H).

Step 5: Removal of the Protecting Group of the Compound of Formula (H-1-a) to Form the Compound of Formula (H)

The reaction flask containing the concentrated compound of formula (H-1-a) (17.8 kg, 70.4 mol) was filled with nitrogen gas, and then cooled to 0° C. A 4 M solution of hydrogen chloride in ethyl acetate (43.4 L, 175.9 mol) was added. The mixture was allowed to naturally warm to room temperature, and reacted with stirring overnight.

The reaction was monitored by HPLC until the reaction was completed. The reaction solution was cooled to 0° C. Methyl tert-butyl ether (20 L) was added, and the mixture was stirred for 30 min. The mixture was filtered. The filter cake was washed with methyl tert-butyl ether (10 L), and dried in vacuum at 40° C. overnight to give 13.1 kg of a white powder in a yield of 98%. LC-MS: m/z=154.2 (M+1)$^1$, purity: 97.5%, and wavelength: 220 nm.

Example 12: Synthesis of (10R)-7-amino-12-fluoro-2-(methyl-d$_3$)-10,16-dimethyl-15-oxo-10,15,16,17-tetrahydro-2H-8,4-(metheno)pyrazolo[4,3-h][2,5,11]benzoxadiazacyclotetradecine-3-carbonitrile (the Compound of Formula (A))

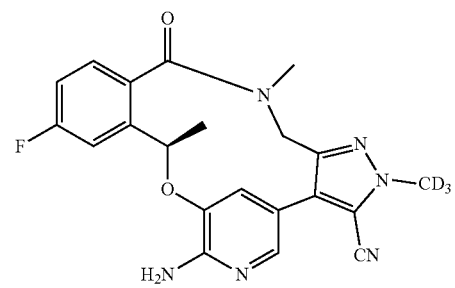

(A)

The following route was used for the synthesis:

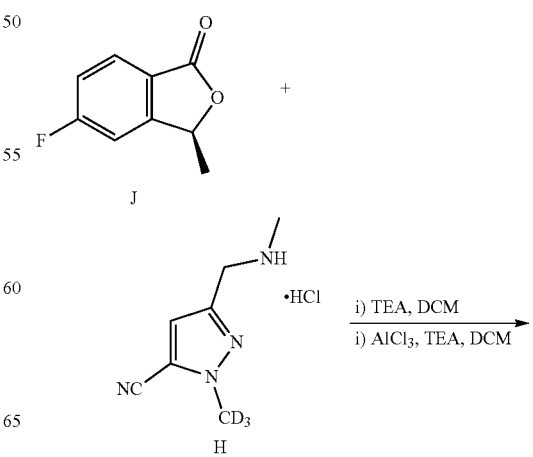

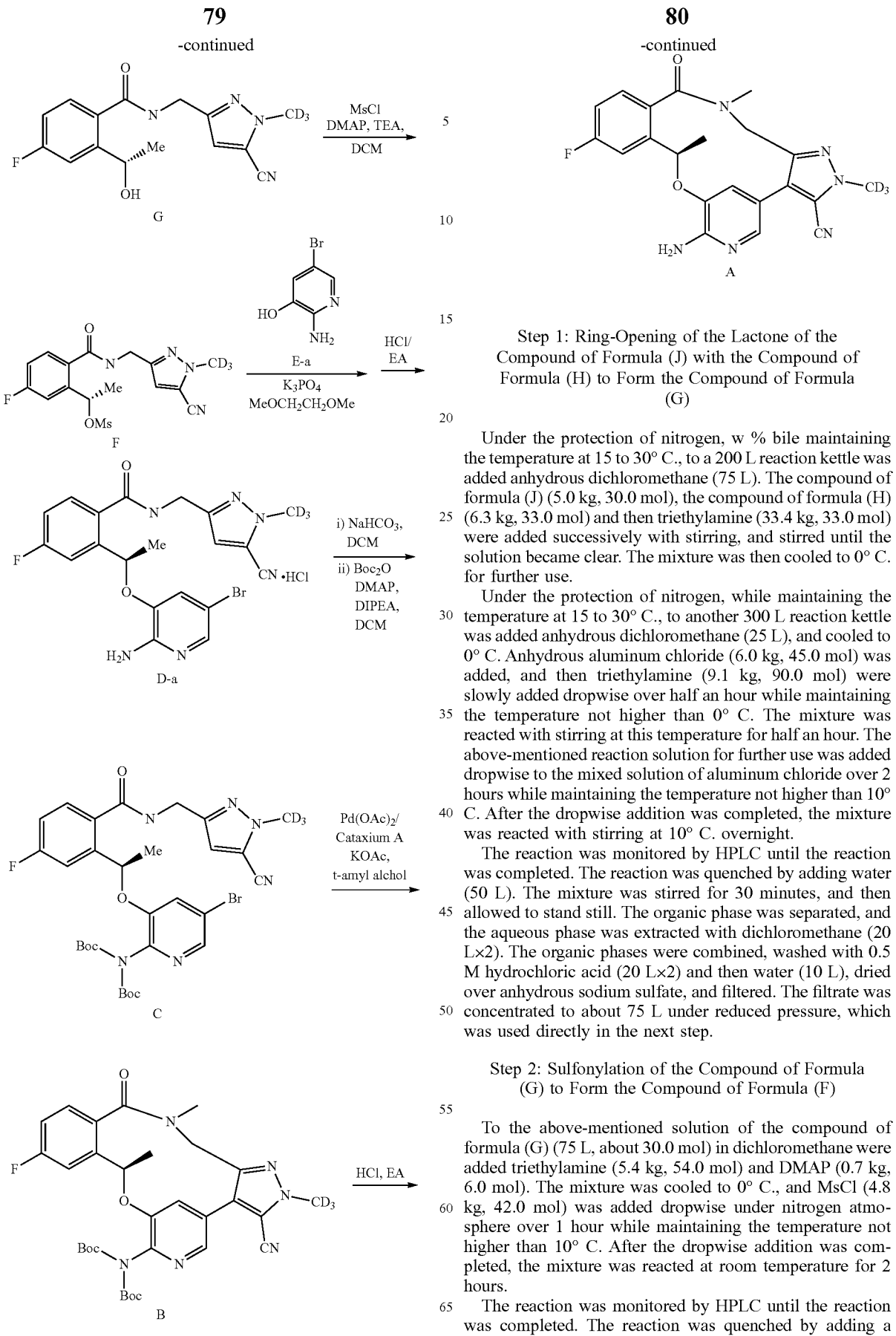

Step 1: Ring-Opening of the Lactone of the Compound of Formula (J) with the Compound of Formula (H) to Form the Compound of Formula (G)

Under the protection of nitrogen, w % bile maintaining the temperature at 15 to 30° C., to a 200 L reaction kettle was added anhydrous dichloromethane (75 L). The compound of formula (J) (5.0 kg, 30.0 mol), the compound of formula (H) (6.3 kg, 33.0 mol) and then triethylamine (33.4 kg, 33.0 mol) were added successively with stirring, and stirred until the solution became clear. The mixture was then cooled to 0° C. for further use.

Under the protection of nitrogen, while maintaining the temperature at 15 to 30° C., to another 300 L reaction kettle was added anhydrous dichloromethane (25 L), and cooled to 0° C. Anhydrous aluminum chloride (6.0 kg, 45.0 mol) was added, and then triethylamine (9.1 kg, 90.0 mol) were slowly added dropwise over half an hour while maintaining the temperature not higher than 0° C. The mixture was reacted with stirring at this temperature for half an hour. The above-mentioned reaction solution for further use was added dropwise to the mixed solution of aluminum chloride over 2 hours while maintaining the temperature not higher than 10° C. After the dropwise addition was completed, the mixture was reacted with stirring at 10° C. overnight.

The reaction was monitored by HPLC until the reaction was completed. The reaction was quenched by adding water (50 L). The mixture was stirred for 30 minutes, and then allowed to stand still. The organic phase was separated, and the aqueous phase was extracted with dichloromethane (20 L×2). The organic phases were combined, washed with 0.5 M hydrochloric acid (20 L×2) and then water (10 L), dried over anhydrous sodium sulfate, and filtered. The filtrate was concentrated to about 75 L under reduced pressure, which was used directly in the next step.

Step 2: Sulfonylation of the Compound of Formula (G) to Form the Compound of Formula (F)

To the above-mentioned solution of the compound of formula (G) (75 L, about 30.0 mol) in dichloromethane were added triethylamine (5.4 kg, 54.0 mol) and DMAP (0.7 kg, 6.0 mol). The mixture was cooled to 0° C., and MsCl (4.8 kg, 42.0 mol) was added dropwise under nitrogen atmosphere over 1 hour while maintaining the temperature not higher than 10° C. After the dropwise addition was completed, the mixture was reacted at room temperature for 2 hours.

The reaction was monitored by HPLC until the reaction was completed. The reaction was quenched by adding a saturated solution of sodium bicarbonate (25 L) while maintaining the temperature not higher than 20° C. The mixture was stirred for half an hour, and then allowed to stand still. The organic phase was separated, washed with saturated brine (10 L), dried over anhydrous sodium sulfate, and filtered. The filtrate was concentrated to about 8 L under reduced pressure. Glycol dimethyl ether (20 L) was added, and the mixture was concentrated to about 15 L under reduced pressure, which was used directly in the next step.

Step 3: Alkylation of the Compound of Formula (E-a) with the Compound of Formula (F) to Form the Compound of Formula (D-a)

Under the protection of nitrogen, while maintaining the temperature at 15 to 30° C., to a 200 L reaction kettle was added glycol dimethyl ether (70 L). The compound of formula (E-a) (6.7 kg, 36.0 mol) was added with stirring, and stirred until the solution became clear. Potassium phosphate (9.5 kg, 45.0 mol) was added. The mixture was heated to 50° C., and stirred at this temperature for 1 hour. The above-mentioned solution of the compound of formula (F) in glycol dimethyl ether (about 30.0 mol, 20 L) was slowly added dropwise to the phenol suspension over 2 hours. After the dropwise addition was completed, the mixture was reacted with stirring at 50° C. overnight. The reaction was monitored by HPLC until the reaction was completed. The reaction solution was concentrated to about 10 L under reduced pressure, and then methyl tert-butyl ether (10 L) and water (15 L) were added. The mixture was stirred for 20 min, and then allowed to stand still. The lower aqueous phase was separated, and extracted with methyl tert-butyl ether (5 L×2). The organic phases were combined, and washed with water (10 L×3). Water (20 L) was added to the organic phase, and 6 M hydrochloric acid (7.5 L, 45 mol) was added dropwise under cooling. The mixture was stirred for 20 min, and then allowed to stand still. The lower aqueous phase was separated, and washed with methyl tert-butyl ether (5 L). The organic phase was discarded.

To the aqueous phase was added methyl tert-butyl ether (20 L), and a 30% solution of sodium hydroxide (6.0 L, 45 mol) was added dropwise under cooling. The mixture was stirred for 20 mm, and then allowed to stand still. The aqueous phase was separated, and extracted with methyl tert-butyl ether (5 L). The organic phases were combined, and dried over anhydrous sodium sulfate. The aqueous phase was discarded.

To the dried organic phase was added dropwise a 4 M solution of hydrogen chloride in ethyl acetate (11.3 L, 45 mol) under cooling. After the dropwise addition was completed, the mixture was stirred at 0° C. for 1 hour, and then filtered. The filter cake was washed with methyl tert-butyl ether (2 L), and dried in vacuum at 40° C. overnight to give 7.1 kg of a light yellow solid. The total yield of the three steps was 45.1%. LC-MS: m/z=490.0 (M+1)$^+$, purity: 89.1%, and wavelength: 220 nm.

Step 4: Introduction of the Boc Protecting Group into the Compound of Formula (D-a) to Form the Compound of Formula (C)

Under the protection of nitrogen, while maintaining the temperature at 15 to 30° C., to a 200 L reaction kettle was added dichloromethane (70.0 L). The compound of formula (D-a) (7.0 kg, 13.3 mol) was added with stirring. A saturated aqueous solution of sodium bicarbonate (35.0 L) was slowly added under cooling while maintaining the temperature below 30° C. The mixture was stirred for half an hour, and then allowed to stand still. The organic phase was separated, and washed with saturated brine (10 L). The organic phase was dried over anhydrous sodium sulfate, and filtered.

To another 200 L reaction kettle was added the solution of the free base in dichloromethane, and stirring was started. DMAP (0.32 kg, 2.66 mol) and then DIPEA (3.43 kg, 26.6 mol) were added successively under nitrogen atmosphere. A solution of Boc$_2$O (11.6 kg, 53.2 mol) in dichloromethane (20 L) was added dropwise under cooling over 2 hours while maintaining the temperature below 30° C. After the dropwise addition was completed, the mixture was reacted with stirring at room temperature overnight (16 hours).

The reaction was monitored by HPLC until the reaction was completed. 1 M hydrochloric acid (35.0 mol, 35.0 L) was slowly added under cooling. The mixture was stirred for 1 hour, and then allowed to stand still. The organic phase was separated, washed with saturated brine (30 L), dried over anhydrous sodium sulfate, and filtered. The filtrate was concentrated to about 8 L under reduced pressure. Tert-pentanol (20 L) was added, and the mixture was concentrated to about 15 L under reduced pressure while maintaining the temperature not higher than 70° C. in a water bath, which was used directly in the next step. LC-MS: m/z=690.2 (M+1)$^+$, purity: 86.2%, and wavelength: 220 nm.

Step 5: Cyclization of the Compound of Formula (C) Using Palladium Catalyst to Form the Compound of Formula (B)

The reaction kettle was evacuated with suction to ≤−0.08 MPa, and then filled with nitrogen gas to normal pressure. The replacement was repeated three times. The solution of the compound of formula (C) (about 13.3 mol) in tert-pentanol (about 15 L) was transferred to a 1000 L reaction kettle. Tert-pentanol (300 L), potassium acetate (3.91 kg, 39.9 mol), and then palladium acetate (120 g, 0.53 mol) were added successively to the reaction kettle. The reaction kettle was evacuated with suction to ≤−0.08 MPa, and then filled with nitrogen gas to normal pressure. The replacement was repeated three times. n-butylbis(1-adamantyl)phosphine (477 g, 1.33 mol) was added to the reaction kettle, and nitrogen gas was bubbled into the reaction kettle below the liquid level for at least 1 hour. The mixture was heated to 105+5° C. under nitrogen atmosphere, and reacted at this temperature overnight (16 hours).

The reaction was monitored by HPLC until the reaction was completed. The reaction solution was cooled to room temperature, and sodium bicarbonate (1.67 kg, 20.0 mol) was added. The mixture was stirred for 10 min, and then concentrated to about 30 L under reduced pressure while maintaining the temperature not higher than 70° C. The mixture was cooled, and then dichloromethane (70 L) was added. The mixture was stirred at room temperature for 2 hours. The reaction solution was then filtered through Celite, and washed with dichloromethane (10 L×2). The organic phases were combined, and concentrated to about 10 L under reduced pressure while maintaining the temperature not higher than 70° C. Acetonitrile (35 L) was added, and the mixture was heated to 80° C., and stirred at this temperature for 4 hours. The reaction solution was then gradually cooled down to 0° C. over 2 to 4 hours, and stirred at this temperature for 4 hours. The reaction solution was filtered. The filter cake was washed with acetonitrile (3 L×2), and then collected.

To another 100 L reaction kettle was added the filter cake, followed by acetonitrile (35 L). The mixture was heated to 80° C. with stirring, and then stirred at this temperature for 4 hours. The reaction solution was gradiently cooled down to 0° C. over 2 to 4 hours, and stirred at this temperature for 4 hours. The reaction solution was filtered, and the filter cake was washed with acetonitrile (5 L).

To a 300 L reaction kettle was added the filter cake, followed by ethyl acetate (150 L). The mixture was stirred until clear, and metal scavenger MS001 (3.0 kg) was added. The mixture was heated to 75° C., gradually cooled down to 55° C., and then stirred at this temperature for 8 hours. The reaction solution was then gradiently cooled down to 25° C. over 2 to 4 hours. The mixture was filtered through Celite, and the filter cake was washed with ethyl acetate (5 L×2).

The filtrates were combined, and transferred back to the reaction kettle through a 0.2 μm microporous filter element. The stirring was started. The solution was concentrated to about 7 L under reduced pressure while maintaining the temperature of the jacket 550° C. The temperature in the reaction kettle was adjusted to 55° C., and methyl tert-butyl ether (14.0 L) was slowly added. The mixture was stirred at this temperature for at least 4 hours. The mixture was gradiently cooled to 0° C. over 3 to 5 hours, and then stirred at this temperature for 2 hours. The mixture was filtered, and the filter cake was washed with methyl tert-butyl ether (7.0 L×2). The filter cake was collected, and dried in vacuum at 45° C. to give 3.48 kg in a yield of 43.1% and a purity (HPLC) of >95.0% (ee>99.5%). LC-MS: m/z=510.1 (M−100+1)$^+$. $^1$H NMR (300 MHz, CDCl$_3$) (δ/ppm): 8.22 (d, J=1.8 Hz, 1H), 7.29-7.25 (m, 1H), 7.22-7.16 (m, 2H), 7.03-6.96 (m, 1H), 5.76-5.70 (m, 1H), 4.42 (q, J=14.1 Hz, 2H), 3.15 (s, 3H), 1.76 (d, J=6.0 Hz, 3H), 1.44 (s, 18H).

Step 6. Removal of the Boc from the Compound of Formula (B) Using an Acid to Form the Compound of Formula (A)

A 100 L reaction kettle was evacuated with suction to ≤−0.08 MPa, and then filled with nitrogen gas to normal pressure. The replacement was repeated three times. Ethyl acetate (15 L) was added, and the stirring was started. The compound of formula (B) (3.2 kg, 5.25 mol) was added, and stirred until the solution became clear. Concentrated hydrochloric acid (3.5 L, 42.0 mol) was slowly added while maintaining the temperature below 25° C. After the addition was completed, the mixture was reacted with stirring at room temperature for 4 hours, and then heated to 45° C. and reacted with stirring at this temperature for 8 hours.

The reaction was monitored by HPLC until the reaction was completed. The reaction solution was cooled to room temperature, and ethyl acetate (15 L) was added. The aqueous phase was adjusted to pH of 7-8 by slowly adding a solution of potassium bicarbonate (about 84 mol, 8.4 kg) in water (about 40 L) while maintaining the temperature below 25° C., during which a large amount of gas released. After the addition was completed, the mixture was stirred at room temperature for half an hour, and then allowed to stand still. The upper organic phase was separated, washed with water (10 L×2), dried over anhydrous sodium sulfate, and filtered with a pad of Celite. The filter cake was washed with ethyl acetate (5 L×2). The organic phases were combined, and transferred back to the kettle. Metal scavenger MS001 (480 g) and the second-generation mercapto silica gel (3-mercaptopropyl ethyl sulfide silica) (320 g) were added. The mixture was heated to 65° C. under nitrogen atmosphere, and stirred for 8 hours. The mixture was cooled to room temperature, and filtered through a pad of Celite. The filter cake was washed with ethyl acetate (5 L×3). The filtrates were combined, and concentrated to dryness under reduced pressure while maintaining the temperature not higher than 70° C. to give 1.97 kg of a glassy solid in a yield of 91.6% and a purity (HPLC) of >99.5% (ee>99.5%). LC-MS(APCI): m/z=410.2 (M+1)$^+$.

$^1$H NMR (400 MHz, DMSO-d$_6$) (δ/ppm) 7.62-7.58 (m, 2H), 7.48-7.45 (m, 1H), 7.20-7.16 (m, 1H), 6.81 (s, 1H), 6.21 (s, 2H), 5.63-5.59 (m, 1H), 4.43 (d, J=12.0 Hz, 1H), 4.19 (d, J=12.0 Hz, 1H), 2.99 (s, 3H), 1.68 (d, J=8.0 Hz, 3H).

$^{13}$C NMR (101 MHz, DMSO-d$_6$) (δ/ppm) 168.235, 164.574, 162.119, 151.402, 144.237, 138.625, 137.154, 133.159, 129.044, 127.656, 118.995, 115.625, 114.393, 114.173, 113.182, 111.779, 111.552, 71.262, 46.955, 31.397, 22.440.

$^2$H NMR (400 MHz, DMSO-d$_6$) (δ/ppm) 3.97 (s, 3D).

$^{19}$F NMR (400 MHz, DMSO-d$_6$) (δ/ppm) −110.08 (s, 1F).

The above is detailed description of the present disclosure in conjunction with specific embodiments, and it cannot be assumed that the specific implementation of the present disclosure is limited to these descriptions. For ordinary person skilled in the technical field to which the present disclosure pertains, without deviating from the concept of the present disclosure, various simple deductions or substitutions may be made, which should be regarded as falling within the protection scope of the present disclosure.

What is claimed is:

1. A method for preparing a compound of formula (A):

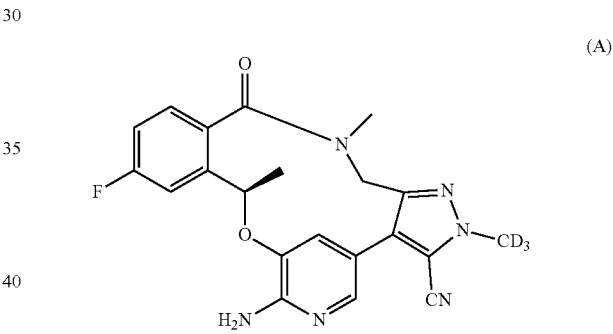

comprising the step of:
reacting a compound of formula (F) with a compound of formula (E-a) to form a compound of formula (D-a):

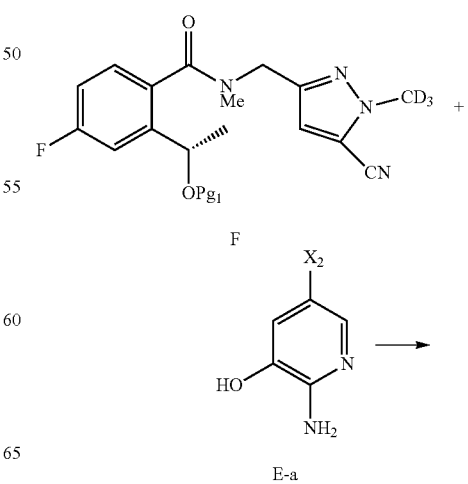

-continued

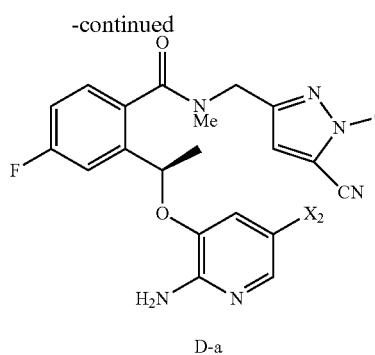

D-a wherein $X_2$ is halogen, and $Pg_1$ is a hydroxy-protecting group;

alternatively, reacting a compound of formula (G) with a compound of formula (E-b) to form a compound of formula (D-b):

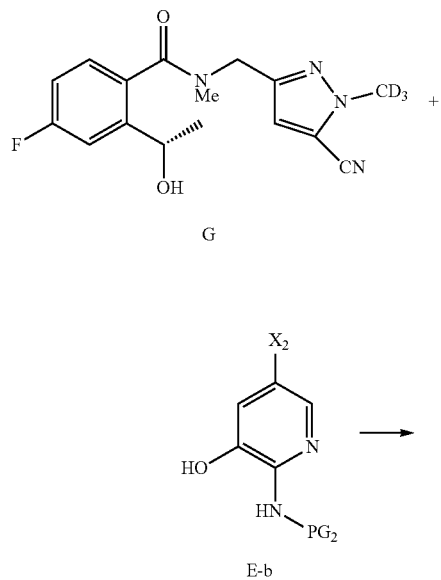

G

E-b

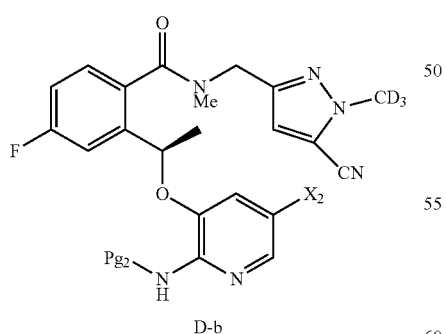

D-b wherein $X_2$ is halogen, and $Pg_2$ is an amino-protecting group.

2. The method of claim 1, further comprising a step of:
reacting a compound of formula (J) with a compound of formula (H) to form the compound of formula (G):

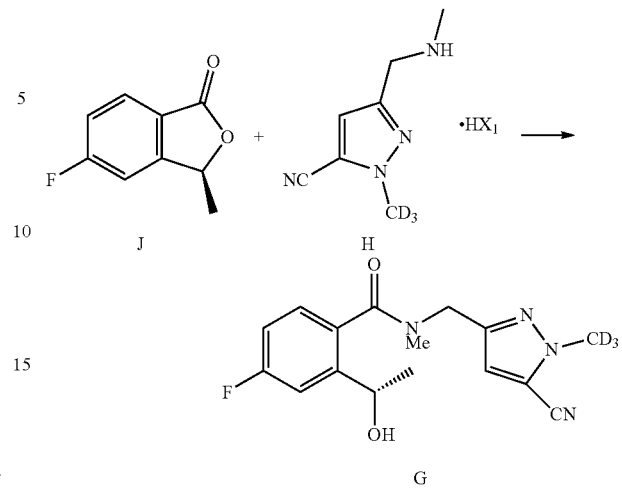

J    H

G wherein $X_1$ is halogen.

3. The method of claim 1, further comprising a step of:
acylating the compound of formula (G) to form the compound of formula (F):

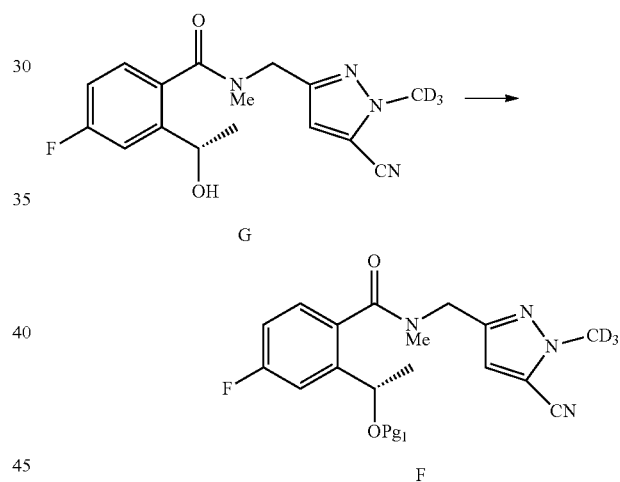

G

F wherein $Pg_1$ is a hydroxy-protecting group.

4. The method of claim 1, further comprising a step of:
protecting the compound of formula (D-a) to form a compound of formula (C):

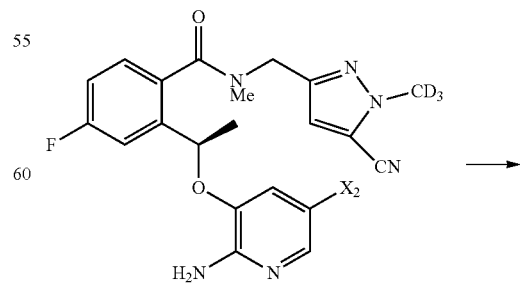

D-a

-continued

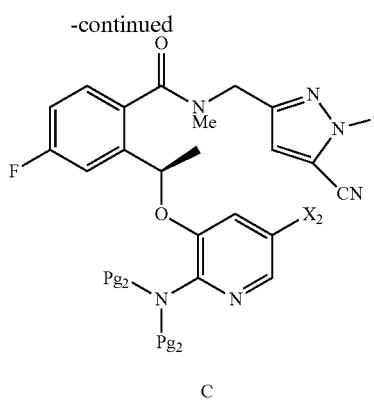

C wherein X₂ is halogen, and Pg₂ is an amino-protecting group;
alternatively, protecting the compound of formula (D-b) to form a compound of formula (C):

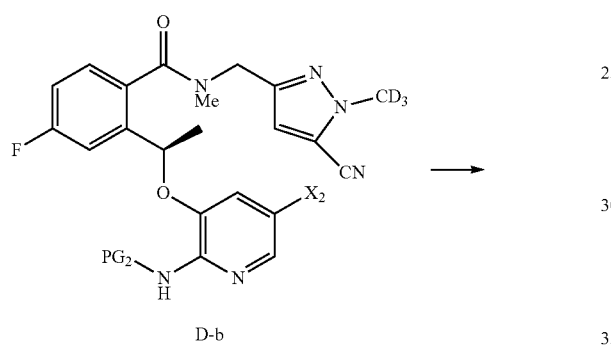

wherein X₂ is halogen, and Pg₂ is an amino-protecting group.

5. The method of claim 4, further comprising a step of:
cyclizing the compound of formula (C) to form a compound of formula (B):

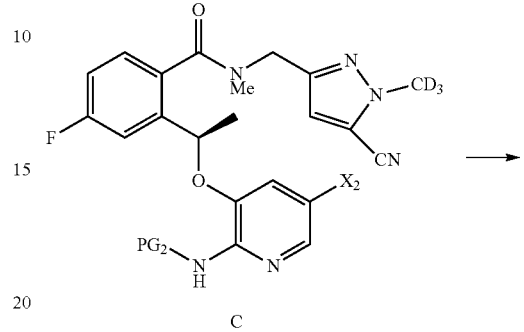

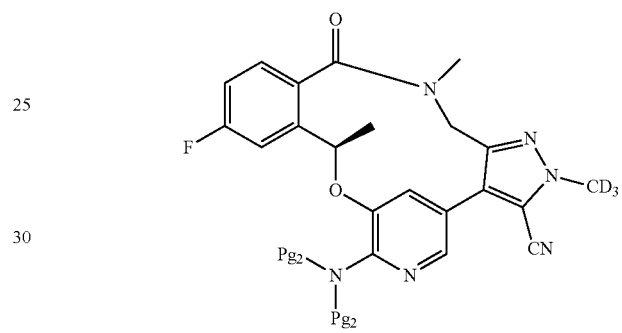

wherein X₂ is halogen, and Pg₂ is an amino-protecting group.

6. The method of claim 5, further comprising a step of:
removing the protecting groups Pg₂ of the compound of formula (B) to obtain the compound of formula (A).

7. The method of claim 1, wherein the hydroxy-protecting group is selected from the group consisting of Ms, Ns, Ts, and Tf.

8. The method of claim 1, wherein the amino-protecting group is selected from the group consisting of Cbz, Boc, Fmoc, Alloc, Teoc, methoxycarbonyl, and ethoxycarbonyl.

* * * * *